United States Patent
Kato et al.

(10) Patent No.: US 8,899,752 B2
(45) Date of Patent: Dec. 2, 2014

(54) VISUAL FATIGUE LEVEL MEASURING DEVICE, VISUAL FATIGUE LEVEL MEASURING METHOD, VISUAL FATIGUE LEVEL MEASURING SYSTEM, AND THREE-DIMENSIONAL GLASSES

(71) Applicant: Panasonic Corporation, Osaka (JP)

(72) Inventors: Yumiko Kato, Osaka (JP); Tsuyoshi Inoue, Nara (JP); Jun Ozawa, Nara (JP)

(73) Assignee: Panasonic Corporation, Osaka (JP)

( * ) Notice: Subject to any disclaimer, the term of this patent is extended or adjusted under 35 U.S.C. 154(b) by 132 days.

(21) Appl. No.: 13/654,784

(22) Filed: Oct. 18, 2012

(65) Prior Publication Data
US 2013/0044291 A1     Feb. 21, 2013

Related U.S. Application Data

(63) Continuation of application No. PCT/JP2012/002120, filed on Mar. 27, 2012.

(30) Foreign Application Priority Data

May 20, 2011   (JP) .................................. 2011-114205

(51) Int. Cl.
| A61B 3/113 | (2006.01) |
| A61B 3/08 | (2006.01) |
| A61B 3/00 | (2006.01) |

(52) U.S. Cl.
CPC .................. *A61B 3/0025* (2013.01); *A61B 3/08* (2013.01); *A61B 3/113* (2013.01)
USPC .......................................... 351/209; 351/201

(58) Field of Classification Search
USPC .......................................... 351/201, 202, 209
See application file for complete search history.

(56) References Cited

U.S. PATENT DOCUMENTS

| 5,357,293 | A | * | 10/1994 | Uomori et al. ................ 351/209 |
| 2011/0063421 | A1 | * | 3/2011 | Kubota ............................ 348/52 |
| 2011/0304818 | A1 | * | 12/2011 | Reichow et al. .............. 351/201 |

FOREIGN PATENT DOCUMENTS

| JP | 9-18894 | 1/1997 |
| JP | 9-218375 | 8/1997 |
| JP | 2000-259854 | 9/2000 |
| JP | 4121880 | 7/2008 |
| WO | 2012/157177 | 11/2012 |

OTHER PUBLICATIONS

"Techniques for Accessibility Evaluation And Repair Tools", W3C Working Draft, Apr. 26, 2000.

* cited by examiner

*Primary Examiner* — Jordan Schwartz
(74) *Attorney, Agent, or Firm* — Wenderoth, Lind & Ponack, LLP

(57) ABSTRACT

A visual fatigue level measuring device includes: a video presenting unit which presents 3D video; a test period determining unit which determines two or more time periods each of which is for a test for measuring a level of visual fatigue; an eye movement obtaining unit which obtains data indicating eye movements of left and right eyes of a player with respect to the presented video; an eye movement extracting unit which extracts, from the obtained eye movement data, eye movement data in each of the two or more time periods determined by the test period determining unit; an eye movement comparing unit which compares eye movements in the two or more time periods based on the extracted data; and a fatigue level determining unit which determines the level of visual fatigue of the player based on the comparison result.

15 Claims, 52 Drawing Sheets

FIG. 4

| Elapsed time | Left/Right | Image |
|---|---|---|
| ⋮ | ⋮ | ⋮ |
| 00:13:15. 024 | Left | |
| 00:13:05. 032 | Right | |
| 00:13:05. 040 | Left | |
| 00:13:05. 048 | Right | |
| 00:13:05. 056 | Left | |
| ⋮ | ⋮ | ⋮ |

| Elapsed time | Target ID | Central coordinates of right screen target | Central coordinates of left screen target | Boundary coordinates of right screen target | Boundary coordinates of left screen target |
|---|---|---|---|---|---|
| .... | .... | .... | .... | .... | .... |
| 00:13:04.024 | 0009 | (280, 210) | (290, 210) | (280, 190), (330, 200), (340, 512), (260, 512) | (270, 190), (320, 200), (330, 512), (250, 512) |
| 00:13:04.040 | 0009 | (280, 210) | (290, 210) | (280, 190), (330, 200), (340, 512), (260, 512) | (270, 190), (320, 200), (330, 512), (250, 512) |
| 00:13:04.056 | 0009 | (275, 210) | (295, 210) | (270, 190), (300, 200), (320, 512), (240, 512) | (260, 190), (310, 200), (320, 512), (240, 512) |
| 00:13:04.072 | 0009 | (270, 210) | (300, 210) | (250, 170), (310, 200), (320, 512), (240, 512) | (240, 170), (320, 200), (330, 512), (250, 512) |
| 00:13:04.088 | 0009<br>0010 | (270, 210)<br>(570, 470) | (300, 210)<br>(560, 470) | (250, 170), (310, 200), (320, 512), (240, 512)<br>(560, 490), (580, 480), (580, 512), (550, 512) | (240, 170), (320, 200), (330, 512), (250, 512)<br>(550, 490), (570, 480), (570, 512), (540, 512) |
| 00:13:04.104 | 0009<br>0010 | (260, 190)<br>(540, 420) | (310, 190)<br>(550, 420) | (270, 150), (320, 170), (330, 512), (250, 512)<br>(520, 400), (560, 390), (570, 512), (510, 512) | (280, 150), (330, 170), (340, 512), (260, 512)<br>(530, 400), (570, 390), (580, 512), (520, 512) |
| 00:13:04.120 | 0009<br>0010 | (120, 170)<br>(500, 400) | (180, 170)<br>(530, 400) | (100, 190), (140, 190), (160, 512), (100, 512)<br>(480, 380), (520, 410), (540, 512), (470, 512) | (160, 190), (200, 190), (220, 512), (160, 512)<br>(510, 380), (550, 410), (570, 512), (500, 512) |
| 00:13:04.136 | 0010 | (500, 400) | (530, 400) | (480, 380), (520, 410), (540, 512), (470, 512) | (510, 380), (550, 410), (570, 512), (500, 512) |
| 00:13:04.152 | 0010 | (500, 400) | (530, 400) | (480, 380), (520, 410), (540, 512), (470, 512) | (510, 380), (550, 410), (570, 512), (500, 512) |
| .... | .... | .... | .... | .... | .... |

| Elapsed time | Control | Coordinates of right screen aim | Coordinates of left screen aim |
|---|---|---|---|
| ⋮ | ⋮ | ⋮ | ⋮ |
| 00:13:04.056 | Move aim | (280, 210) | (290, 210) |
| 00:13:04.066 | Move aim | (275, 210) | (295, 210) |
| 00:13:04.076 | Move aim | (270, 210) | (300, 210) |
| 00:13:04.086 | Shoot | (270, 210) | (300, 210) |
| 00:13:04.096 | Shoot | (270, 210) | (300, 210) |
| 00:13:04.126 | Move aim | (260, 200) | (290, 200) |
| 00:13:04.136 | Shoot | (260, 200) | (290, 200) |
| 00:13:04.156 | Move aim | (280, 220) | (280, 220) |
| 00:13:04.166 | Shoot | (280, 220) | (280, 220) |
| ⋮ | ⋮ | ⋮ | ⋮ |

| Elapsed time | Coordinates of center of right eye pupil | Coordinates of center of left eye pupil |
|---|---|---|
| ⋮ | ⋮ | ⋮ |
| 00:13:04. 056 | (130, 240) | (480, 240) |
| 00:13:04. 089 | (135, 242) | (482, 241) |
| 00:13:04. 132 | (139, 239) | (484, 237) |
| 00:13:04. 165 | (147, 240) | (488, 239) |
| ⋮ | ⋮ | ⋮ |

FIG. 24

|  | | Comparison result of eye movement | | |
|---|---|---|---|---|
|  | | No difference in both eyes | Change in one eye | Change in both eyes |
| Movement speed of visual target | Slow | No fatigue | Fatigued | Fatigued |
| | Medium | No fatigue | Fatigue symptoms | Fatigued |
| | Fast | No fatigue | Fatigue symptoms | Fatigued |

FIG. 39

| Elapsed time | Left and right difference of horizontal axis | Left and right difference of vertical axis |
|---|---|---|
| 00:13:04.056 | 350 | 0 |
| 00:13:04.089 | 353 | -1 |
| 00:13:04.132 | 345 | -2 |
| ⋮ | ⋮ | ⋮ |

332a

VISUAL FATIGUE LEVEL MEASURING DEVICE, VISUAL FATIGUE LEVEL MEASURING METHOD, VISUAL FATIGUE LEVEL MEASURING SYSTEM, AND THREE-DIMENSIONAL GLASSES

CROSS REFERENCE TO RELATED APPLICATIONS

This is a continuation application of PCT Patent Application No. PCT/JP2012/002120 filed on Mar. 27, 2012, designating the United States of America, which is based on and claims priority of Japanese Patent Application No. 2011-114205 filed on May 20, 2011. The entire disclosures of the above-identified applications, including the specifications, drawings and claims are incorporated herein by reference in their entirety.

FIELD

One or more exemplary embodiments disclosed herein relate generally to visual fatigue level measuring devices and visual fatigue level measuring methods which measure the state of visual fatigue (the level of visual fatigue) of players who view three-dimensional (3D) video such as games.

BACKGROUND 3D video is spreading not only as movies but also as television content or video for games along with the popularization of home-use televisions and computer displays which allow 3D display. 3D video provides viewers with illusion of depth by providing parallax between images presented to the right eyes and the left eyes. Such 3D video allows the viewers to perceive depth stereoscopically and to enjoy more realistic and powerful video. In particular, 3D video games allow players to enjoy a deeper experience. However, it is said that 3D video causes heavier visual fatigue (eye strain) than conventional two-dimensional video. One cause that has been discussed is that the visual line moves to a position in the depth direction virtually displayed in the 3D video. Although the distance from the angle formed by both eyes to the virtual position is perceived, focus of the eyes is adjusted to the screen position at which the video is presented, because the focus is adjusted to the video. As a result, the angle of the eyes contradicts the focus adjustment. Furthermore, it is believed that extreme movement in the depth direction or sudden depth changes due to scene changes in video causes excessive eye movements, resulting in causing fatigue that is different from fatigue caused by 2D video.

Hence, in order to avoid causing extreme fatigue after viewing 3D video, there is a method, as in Patent Literature 1, for measuring fatigue by presenting test video in the middle of viewing and measuring eye movements performed when the visual line follows the point of gaze that moves on the screen.

Furthermore, there is also a method, as in Patent Literature 2, for measuring fatigue of viewers using the information from the video that is being viewed.

CITATION LIST

Patent Literature

[PTL 1]
Japanese Unexamined Patent Application Publication No. 9-218375
[PTL 2]
Japanese Patent No. 4121880

SUMMARY

Technical Problem

However, in the technique disclosed in PTL 1, viewing 3D video such as games has to be interrupted to measure the level of visual fatigue of the viewers.

The technique disclosed in PTL 2 does not account for individual differences of visual functions due to age or the like; and thus, it is not possible to accurately measure fatigue of the viewers.

One non-limiting and exemplary embodiment provides a visual fatigue level measuring device and the like which is capable of accurately measuring the level of visual fatigue of viewers without interrupting viewing of 3D video such as games and regardless of individual differences of visual functions due to age or the like.

Solution to Problem

In one general aspect, the techniques disclosed here feature a visual fatigue level measuring device which measures a level of visual fatigue of a user who is viewing three-dimensional (3D) video. The visual fatigue level measuring device includes: a video presenting unit which presents, to the user, left-eye video and right-eye video that are included in the 3D video; a control input unit which receives a control by the user with respect to the presented 3D video; a gaze target identifying unit which, when the control input unit receives a predetermined control, (i) obtains, from a storing unit, target region information including information for identifying a visual target in the 3D video and information indicating time at which the visual target is presented by the video presenting unit, and (ii) determines that the user was gazing at the visual target in the 3D video presented by the video presenting unit at a time at which the control input unit received the predetermined control, by referring to the obtained target region information; a test period determining unit which (i) obtains, from the storing unit, target depth information indicating a depth of the visual target in the 3D video, and (ii) determines two or more time periods based on a depth change of the visual target identified by the gaze target identifying unit, by referring to the obtained target depth information, each of the two or more time periods being a time period for a test for measuring the level of visual fatigue; an eye movement obtaining unit which obtains data indicating eye movements of left and right eyes of the user with respect to the 3D video presented by the video presenting unit; an eye movement accumulating unit which accumulates the obtained data indicating the eye movements; an eye movement extracting unit which extracts, from the data accumulated in the eye movement accumulating unit, data indicating the eye movements in each of the two or more time periods determined by the test period determining unit; an eye movement comparing unit which compares the eye movements in the two or more time periods based on the data extracted by the eye movement extracting unit; and a fatigue level determining unit determines the level of visual fatigue of the user based on a result of the comparison by the eye movement comparing unit.

These general and specific aspects may be implemented not only as such a visual fatigue level measuring device, but also as a visual fatigue level measuring method, a program causing a computer to execute the method, a computer-readable recording medium, such as a CD-ROM, on which the program is recorded, a semiconductor integrated circuit, a visual fatigue level measuring system, or 3D glasses.

Additional benefits and advantages of the disclosed embodiments will be apparent from the Specification and Drawings. The benefits and/or advantages may be individually obtained by the various embodiments and features of the Specification and Drawings, which need not all be provided in order to obtain one or more of such benefits and/or advantages.

Advantageous Effects

A visual fatigue level measuring device and the like according to one or more exemplary embodiments or features disclosed herein allows accurate measurement of the level of visual fatigue caused by 3D video viewing, without interrupting viewing of 3D video such as games and regardless of individual differences of visual functions due to, for example, age of viewers.

Hence, the present disclosure has a significant practical value in the present age when 3D video such as televisions and games is becoming popular.

BRIEF DESCRIPTION OF DRAWINGS

These and other advantages and features will become apparent from the following description thereof taken in conjunction with the accompanying Drawings, by way of non-limiting examples of embodiments disclosed herein.

FIG. 4 shows an example of video information accumulated in a video information accumulating unit shown in FIG. 3.

FIG. 7 shows an example of target region information stored in a target region information storing unit shown in FIG. 3.

FIG. 8 shows an example of control history accumulated in a control history accumulating unit shown in FIG. 3.

FIG. 9 shows an example of eye movement data accumulated in an eye movement accumulating unit shown in FIG. 3.

FIG. 24 is a diagram for explaining an example of a method for determining the level of fatigue according to Embodiment 1.

FIG. 39 shows an example of left and right difference data accumulated in a left and right difference accumulating unit shown in FIG. 37.

DESCRIPTION OF EMBODIMENTS

Details of Problems in Background

Figure 1:
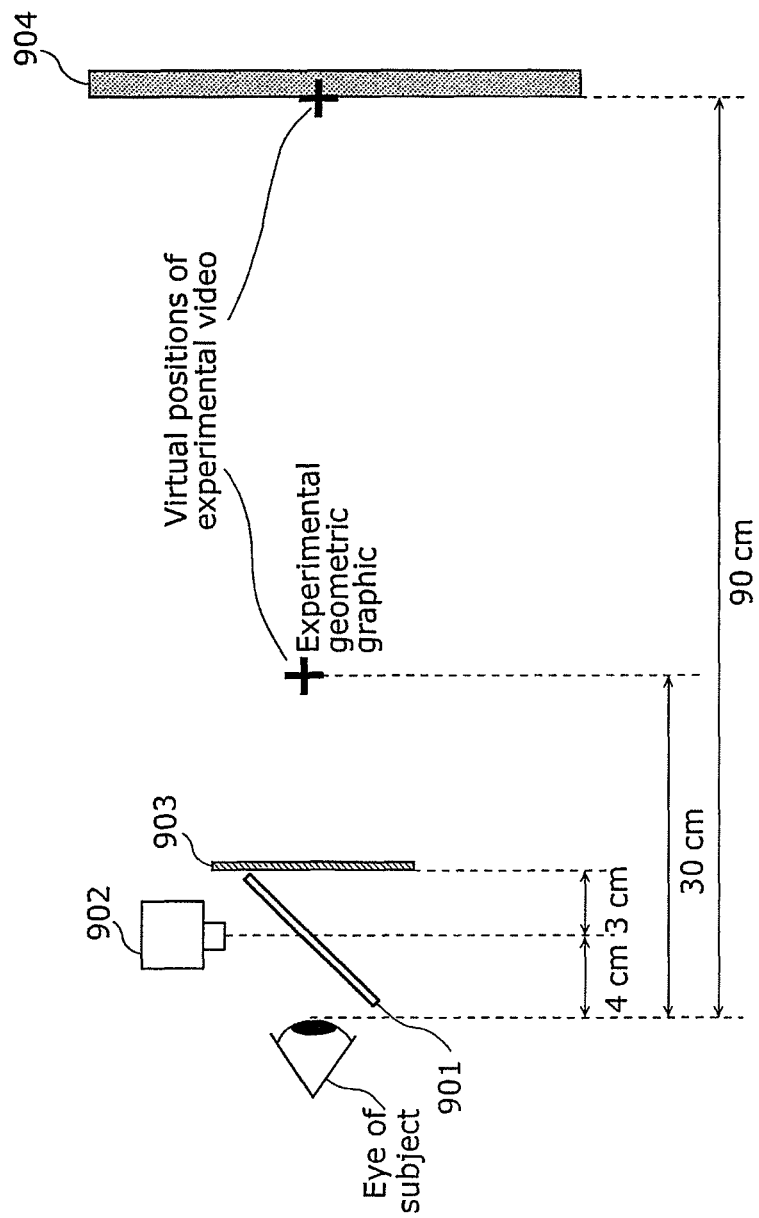
FIG. 1 is a diagram for explaining an experiment for examining relationship between visual fatigue due to 3D video viewing and eye movements.

In relation to the techniques disclosed in PTL1 and PTL2 described in the Background section, the inventors have found the following problems.

PTL 1 discloses a method for measuring fatigue to prevent extreme fatigue from occurring after viewing 3D video. In the method, fatigue is measured by presenting test video in the middle of viewing, and by measuring eye movements performed when the visual line follows the point of gaze on the screen. However, conducting tests by watching test video that is irrelevant to the viewing content in the middle of viewing ruins enjoyment of video viewing and games. Furthermore, viewers may avoid test modes because of inconvenience of interrupting video viewing or games, resulting in losing chances for testing fatigue caused due to 3D video viewing.

In view of this, PTL2 discloses a method for measuring fatigue of viewers by using the viewing content and the information from the video that is being viewed. PTL 2 discloses a method for measuring the level of fatigue by calculating, based on virtual positions of visual targets presented by 3D video that is the viewing content, the positions of the eyes for viewing the virtual positions and the states of lens accommodation, and obtaining the degree of displacement between the eyes of the viewers and the states of the eyes for viewing the video.

However, it is generally believed that lens accommodation is discrepant from the angle of convergence of the eyes when viewing 3D video. It is believed that lenses are not accommodated to the virtual positions of visual targets, but rather to the display screen position on which the actual video is being presented to bring into focus. Furthermore, the ability of lens accommodation differs significantly depending on age. It is difficult to extract changes in accommodation due to fatigue from elderly people who have poor accommodation. Furthermore, it is known that the ability of stereoscopic viewing and the range of stereoscopic vision differ significantly depending on each person.

Thus, determining fatigue based on the displacement between the gaze point obtained from the visual line and the virtual position of the video as in PTL 2 may result in a false determination that a person who has a narrow range of stereoscopic vision is fatigued even if he or she is not. As a result, the technique disclosed in PTL 2 does not account for individual differences of visual functions due to age or the like; and thus, it is not possible to accurately measure fatigue of viewers.

(Aspects for Solving the Problems)

In light of the foregoing information, the inventors have invented visual fatigue level measuring devices and the like which are capable of accurately measuring the level of visual fatigue of viewers without interrupting viewing of 3D video such as games and regardless of individual differences of visual functions due to age or the like.

According to an exemplary embodiment disclosed herein, a visual fatigue level measuring device measures the level of visual fatigue of a user who is viewing 3D video. The visual fatigue level measuring device includes: a video presenting unit which presents, to the user, left-eye video and right-eye video that are included in the 3D video; a control input unit which receives a control by the user with respect to the presented 3D video; a gaze target identifying unit which, when the control input unit receives a predetermined control, (i) obtains, from a storing unit, target region information including information for identifying a visual target in the 3D video and information indicating time at which the visual target is presented by the video presenting unit, and (ii) determines that the user was gazing at the visual target in the 3D video presented by the video presenting unit at a time at which the control input unit received the predetermined control, by referring to the obtained target region information; a test period determining unit which (i) obtains, from the storing unit, target depth information indicating a depth of the visual target in the 3D video, and (ii) determines two or more time periods based on a depth change of the visual target identified by the gaze target identifying unit, by referring to the obtained target depth information, each of the two or more time periods being a time period for a test for measuring the level of visual fatigue; an eye movement obtaining unit which obtains data indicating eye movements of left and right eyes of the user with respect to the 3D video presented by the video presenting unit; an eye movement accumulating unit which accumulates the obtained data indicating the eye movements; an eye movement extracting unit which extracts, from the data accumulated in the eye movement accumulating unit, data indicating the eye movements in each of the two or more time periods determined by the test period determining unit; an eye movement comparing unit which compares the eye movements in the two or more time periods based on the data extracted by the eye movement extracting unit; and a fatigue level determining unit which determines the level of visual fatigue of the user based on a result of the comparison by the eye movement comparing unit.

With this, the level of visual fatigue is measured based on the eye movements performed while 3D video is being viewed, allowing the level of visual fatigue to be measured without interrupting viewing of 3D video such as games. Furthermore, the level of visual fatigue is measured according to comparative assessment where eye movements in two or more test periods are compared, allowing accurate measurement of the level of visual fatigue which does not easily depend on individual differences of visual functions due to age or the like.

More specifically, the level of visual fatigue is measured based on the eye movements performed while 3D video is being viewed, and also according to comparative assessment where eye movements in two or more test periods are compared; and thus, the level of fatigue of users can be measured by observing relative changes in the eye movements performed in stereoscopic viewing while 3D video such as games is being viewed. As a result, it is possible to accurately measure fatigue of the users without performing calibration which is irrelevant to viewing of 3D video such as games or without interrupting viewing 3D video such as games.

Here, it may be that when the control input unit receives the predetermined control, the gaze target identifying unit selects one of the visual targets presented by the video presenting unit, and determines that the user was gazing at the selected one of the visual targets. In this way, it is possible to appropriately select a visual target at which a user was gazing from among a plurality of visual targets. This allows accurate relative comparison of eye movements performed while 3D video is being viewed, leading to high-accuracy measurement of the level of fatigue utilizing game content.

Furthermore, it may be that the video presenting unit presents, to the user, left-eye video and right-eye video that are included in a game in which the user aims at the visual target and shoots the visual target, the control input unit receives a control performed by the user to aim at the visual target for shooting, and the gaze target identifying unit identifies the visual target at which the user is gazing based on the control received by the control input unit. In this way, the visual target at which the user is gazing is identified based on user control for aiming at the visual target for shooting. This allows more accurate measurement of the level of visual fatigue using the visual target at which the user is gazing.

Furthermore, it may be that the test period determining unit determines, as the time period for the test for measuring the level of visual fatigue, two or more different time periods which have a same depth change among depth changes of the visual target identified by the gaze target identifying unit. In this way, two or more different time periods having the same depth change are determined as test time periods for measuring the level of visual fatigue; and thus, it is possible to prevent measurement errors due to differences in video.

Furthermore, it is preferable that the fatigue level determining unit determines that the level of visual fatigue is higher as a difference in the eye movements between the two or more time periods increases. In this way, the level of fatigue is determined to be higher as the difference in the eye movements in the two time periods increases; and thus, it is possible to accurately determine the level of visual fatigue according to comparative assessment with respect to different time periods of the same user.

Furthermore, it may be that the gaze target identifying unit determines that the user was gazing at the visual targets concurrently presented by the video presenting unit, and the test period determining unit identifies, as a part of the time period for the test, a time period during which a visual target having a large amount of depth change among the visual targets identified by the gaze target identifying unit is being presented. In this way, the time period, during which a visual target having a large amount of depth change is presented among the visual targets identified by the gaze target identifying unit, is identified as a part of a test time period. This facilitates detection of the difference in the eye movements in two time periods, leading to accurate measurement of the level of visual fatigue.

Furthermore, it may be that the gaze target identifying unit determines that the user was gazing at the visual targets concurrently presented by the video presenting unit, and the test period determining unit identifies, as the time period for the test, a time period during which a visual target having a high speed depth change or a large amount of depth change among the visual targets is being presented. In this way, the time period, during which a visual target having a high speed depth change or a large amount of depth change is presented, is identified as a test time period. This allows the level of fatigue to be measured in a state where fatigue is more likely to appear, leading to high-accuracy measurement even from the state where the level of fatigue is low.

Furthermore, it may be that the eye movement comparing unit compares components of the eye movements which follow a depth movement of the visual target, among eye movement components. In this way, the components of the eye movements which follow the depth movement of the visual target are compared. This particularly allows high-accuracy measurement of fatigue caused due to stereoscopic viewing.

Furthermore, it may be that the eye movement comparing unit compares differences each between a position of a center of a pupil of the left eye and a position of a center of a pupil of the right eye. In this way, eye movements are compared based on the differences between the center position of the left eye pupil and the center position of the right eye pupil; and thus, it is possible to accurately measure the level of visual fatigue using both eyes.

Furthermore, it may be that the gaze target identifying unit generates information indicating a testable period that is a time period during which the user was gazing at the visual target, the visual fatigue level measuring device further includes: a testable period accumulating unit which accumulates information indicating the testable period generated by the gaze target identifying unit; and a target video information generating unit which generates video including the visual target, based on the information indicating the testable period accumulated in the testable period accumulating unit, and the video presenting unit further presents the video generated by the target video information generating unit. In this way, video including a visual target is generated based on information which indicates a testable period accumulated in the testable period accumulating unit and the generated video is presented; and thus, it is possible to naturally insert test video to 3D video such as games while the 3D video is being viewed. This prevents the user from losing chances for tests and accumulating fatigue.

Furthermore, it may be that the target video information generating unit generates video including a visual target which has a depth change equivalent to a depth change of a visual target in the testable period indicated by the information accumulated in the testable period accumulating unit. In this way, video is generated which includes a visual target having a depth change equivalent to the depth change of the visual target in the testable period indicated by the information accumulated in the testable period accumulating unit; and thus, it is possible to generate test video which has the same or similar conditions for stereoscopic viewing, allowing high-accuracy measurement of the level of fatigue.

Furthermore, it may be that the target video information generating unit generates video having a contrast equivalent to a contract between the visual target and background video in the testable period indicated by the information accumulated in the testable period accumulating unit. In this way, video is generated which has a contrast equivalent to the contrast between the visual target and background video in the testable period indicated by the information accumulated in the testable period accumulating unit; and thus, it is possible to generate test video which has the same or similar conditions for facilitating stereoscopic viewing, allowing high-accuracy measurement of the level of fatigue.

Furthermore, it may be that the target video information generating unit generates background video having a line segment which indicates a horizontal plane and which is in an amount equivalent to an amount of a line segment which indicates a horizontal plane in background video and which is contiguous to the visual target in the testable period indicated by the information accumulated in the testable period accumulating unit. In this way, background video is generated which has a line segment indicating a horizontal plane which is in an amount equivalent to the amount of a line segment which indicates a horizontal plane in background video and which is contiguous to the visual target in the testable period indicated by the information accumulated in the testable period accumulating unit; and thus, it is possible to generate test video which have the same or similar conditions for facilitating stereoscopic viewing, allowing high-accuracy measurement of the level of fatigue.

The present disclosure may also be implemented as three-dimensional (3D) glasses for viewing 3D video including an image to be presented to a left eye of a user and an image to be presented to a right eye of the user. The 3D glasses include: an eye movement obtaining unit which measures eye movements of the user; and a fatigue level determining unit which receives information of the eye movements of the user from the eye movement obtaining unit and determines a level of visual fatigue of the user based on the information of the eye movements of the user.

Furthermore, the present disclosure may also be implemented as a visual fatigue level measuring system which includes: an image displaying device which displays three-dimensional (3D) video; and 3D glasses for viewing the 3D video. The 3D glasses include: an eye movement obtaining unit which measures eye movements of a user; and an eye movement information transmitting unit which transmits information of the eye movements measured by the eye movement obtaining unit to the image displaying device including a video presenting unit which presents the 3D video. The image displaying device includes: an image accumulating unit which accumulates an image to be presented to a left eye of the user and an image to be presented to a right eye of the user; a video presenting unit which presents the images accumulated in the image accumulating unit; and a fatigue level determining unit which determines a level of visual fatigue of the user based on the information of the eye movements of the user transmitted from the 3D glasses.

Furthermore, the present disclosure may also be implemented as three-dimensional (3D) glasses for viewing 3D video including an image to be presented to a left eye of a user and an image to be presented to a right eye of the user. The 3D glasses includes: a synchronization signal receiving unit which synchronously receives a signal for switching between the image to be presented to the left eye and the image to be presented to the right eye; a shutter control unit which switches between blocking of video by a right-eye shutter and a left-eye shutter, based on the synchronization signal; an eye movement obtaining unit which measures eye movements of the user of the 3D glasses; and an eye movement information transmitting unit which transmits, to an image displaying device including a video presenting unit which presents the 3D video, information of the eye movements measured by the eye movement obtaining unit.

Hereinafter, certain exemplary embodiments are described in greater detail with reference to the accompanying Drawings. Each of the exemplary embodiments described below shows a general or specific example. The numerical values, shapes, materials, structural elements, the arrangement and connection of the structural elements, steps, the processing order of the steps etc. shown in the following exemplary embodiments are mere examples, and therefore do not limit the scope of the appended Claims and their equivalents. Therefore, among the structural elements in the following exemplary embodiments, structural elements not recited in any one of the independent claims are described as arbitrary structural elements.

(Knowledge Obtained by the Inventors)

Prior to specifically describing the exemplary embodiments, a description is given of relationship, between visual fatigue and eye movements peculiar to stereoscopic viewing, found by the inventors.

The inventors have found through experiments that visual fatigue can be measured by recording eye movements performed when visual fatigue is caused by significant changes in the depth direction of the virtual positions of visual targets.

FIG. 1 is a diagram for explaining an experiment for examining relationship between visual fatigue caused due to 3D video viewing and eye movements. In this experiment, images of the eyes of a subject who was viewing experimental 3D video displayed on a display 904 were obtained by an infrared camera 902 using a half mirror 901 without interrupting video viewing, and the centers of the pupils were obtained from the images for obtaining the positions of the centers of the pupils in the horizontal direction. FIG. 1 schematically shows the arrangement of the half mirror 901, the infrared camera 902, a stereoscopic liquid crystal shutter 903, and the display 904 that were used for the experiment. The infrared camera 902 for capturing images of the eyes of the subject was placed above the eyes of the subject at a position approximately 4 cm away from the eyes. The half mirror 901 for reflecting the images of the eyes of the subject was placed in front of the eyes of the subject and below the infrared camera 902. The stereoscopic liquid crystal shutter 903 was placed at a position approximately 7 cm away from the eyes of the subject.

The distance between the eyes of the subject and the display 904 was 90 cm. The subject was an adult having no ophthalmologic disease other than short-sightedness, and used contact lenses for short-sightedness when necessary in the experiments. In the experimental 3D video, simple geometric graphics ("+" shown in FIG. 1) were displayed alternately every 3 to 5 seconds at the virtual positions shown in FIG. 1. The virtual positions were set at a position 90 cm away from the eyes of the subject, that is, on the display 904, and at a position 30 cm away from the eyes of the subject. The changes in the depth direction (that is, depth changes of 60 cm) are conditions which impose significantly heavy load compared to ordinary 3D movies or video content for games.

Figure 2A:
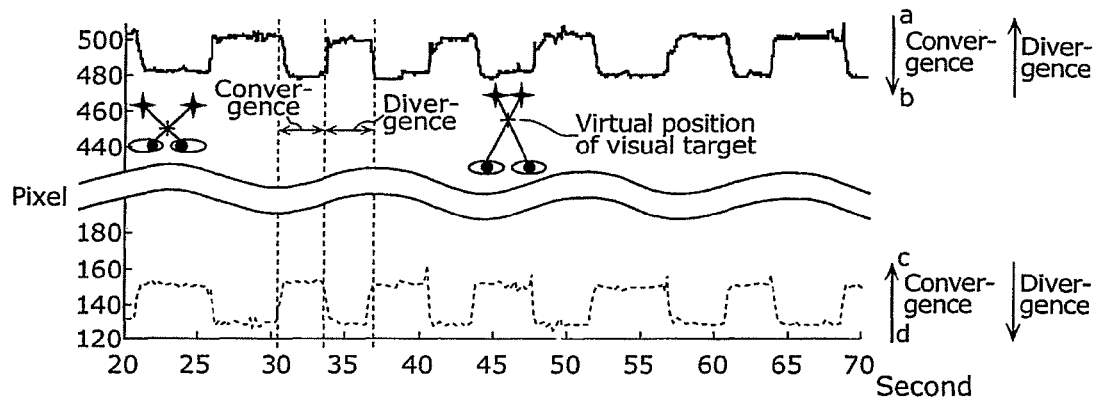
FIG. 2A shows a result of the experiment shown in FIG. 1.
Figure 2B:
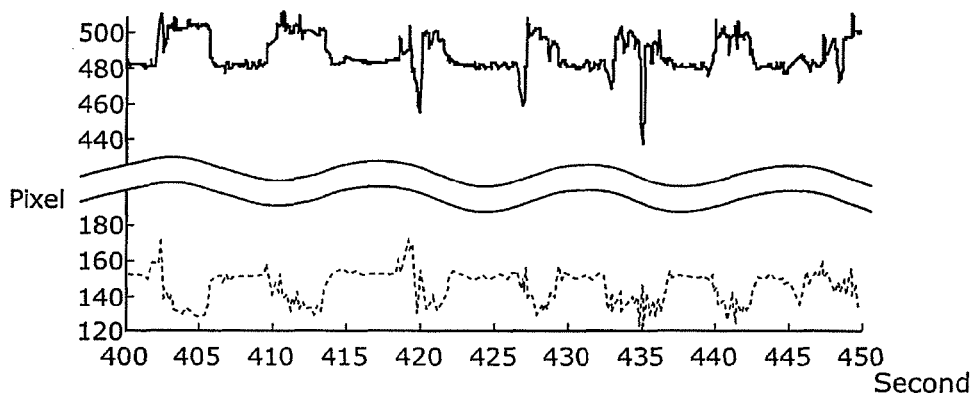
FIG. 2B shows another result of the experiment shown in FIG. 1.
Figure 2C:
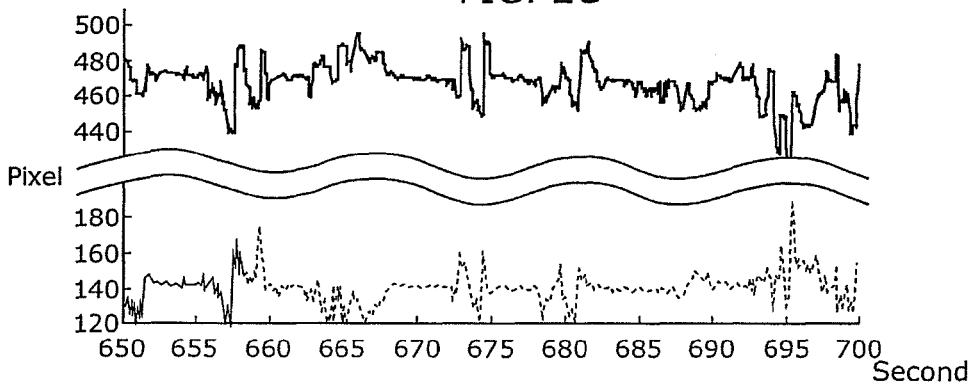
FIG. 2C shows another result of the experiment shown in FIG. 1.
Figure 2D:
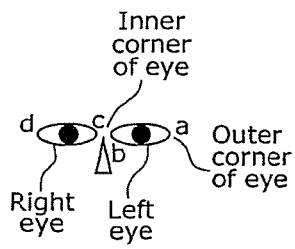
FIG. 2D shows positional relationship between the eyes and nose for showing directions of eye movement.

FIG. 2A to FIG. 2C are graphs showing examples of results obtained from the experiment shown in FIG. 1. Here, the graphs show the horizontal positions of the centers of the pupils of a female subject in her 40 s in the middle of her viewing the experimental 3D video. FIG. 2A shows the positions of the centers of the pupils in the state where the subject is not fatigued from 20 to 50 seconds immediately after the subject started the viewing. FIG. 2B shows the positions of the centers of the pupils for 50 seconds in the state where the subject started to feel fatigue after the elapse of 400 seconds from the start of the viewing. FIG. 2C shows the positions of the centers of the pupils for 50 seconds in the state where stereoscopic viewing is difficult due to fatigue after the elapse of 650 seconds from the start of the viewing. FIG. 2D is a schematic diagram illustrating the positional relationship between the eyes and the nose for showing directions of eye movements. The eye shown at the left side is the right eye of the subject, and the eye shown at the right side is the left eye of the subject. In FIG. 2D, point a indicates the outer corner of the left eye, point b indicates the inner corner of the left eye, point c indicates the inner corner of the right eye, and point d indicates the outer corner of the right eye. In FIG. 2A to FIG. 2C, solid lines indicate the positions of the left eye of the subject. The positive slope indicates the left side of the subject, that is, the outer corner side of the left eye (point a in FIG. 2D), and the negative slope indicates the inner corner side of the left eye (point b in FIG. 2D). The dashed lines indicate the positions of the right eye of the subject. The positive slope indicates the left side of the subject, that is, the inner corner side of the right eye (point c in FIG. 2D), and the negative slope indicates the outer corner side of the right eye (point d in FIG. 2D). At the left in FIG. 2A, relationship between the eyes and a visual target at the time of convergence is schematically shown. At the middle in FIG. 2A, relationship between the eyes and a visual target at the time of divergence is schematically shown. When the depth of the virtual position of the visual target is small, that is, when the visual target looks close for the subject, the eyes of the subject converge, and the centers of the pupils move toward the inner corners of the eyes. In the graphs of FIG. 2A to FIG. 2C, the graphs (dashed lines) of the right eye and the graphs (solid lines) of the left eye come close to each other. When the depth of the virtual position of the visual target is large, that is, when the virtual target looks far for the subject, the eyes of the subject diverge, and the positions of the pupils come close to the front of the eyes. When the positions of the pupils are at the front of the eyes, the eyes are looking at infinity without the visual lines of the right and left eyes crossing each other. FIG. 2A shows that each time the visual target moves a certain depth, the eyes accurately move to a certain position (the eyes follow the depth movement) while the subject is not fatigued immediately after the start of the viewing. As is clear from FIG. 2B showing the graph having slightly collapsed rectangles, at the stages where the subject feels visual fatigue after continuous viewing, the eyes cannot accurately follow the visual target which moves a certain depth. The eyes sometimes do not stay in fixed positions, or do not move to the positions corresponding to the depth. Furthermore, as is clear from FIG. 2C showing the graph having further collapsed rectangles, when the subject is not capable of stereoscopically viewing the visual target at the close position where depth is small due to visual fatigue, convergence movement to the depth of 30 cm is not performed. In this way, by temporally comparing eye movements performed while video is being viewed, it is possible to observe the level of visual fatigue of viewers who are viewing 3D video.

Embodiment 1

Figure 3:
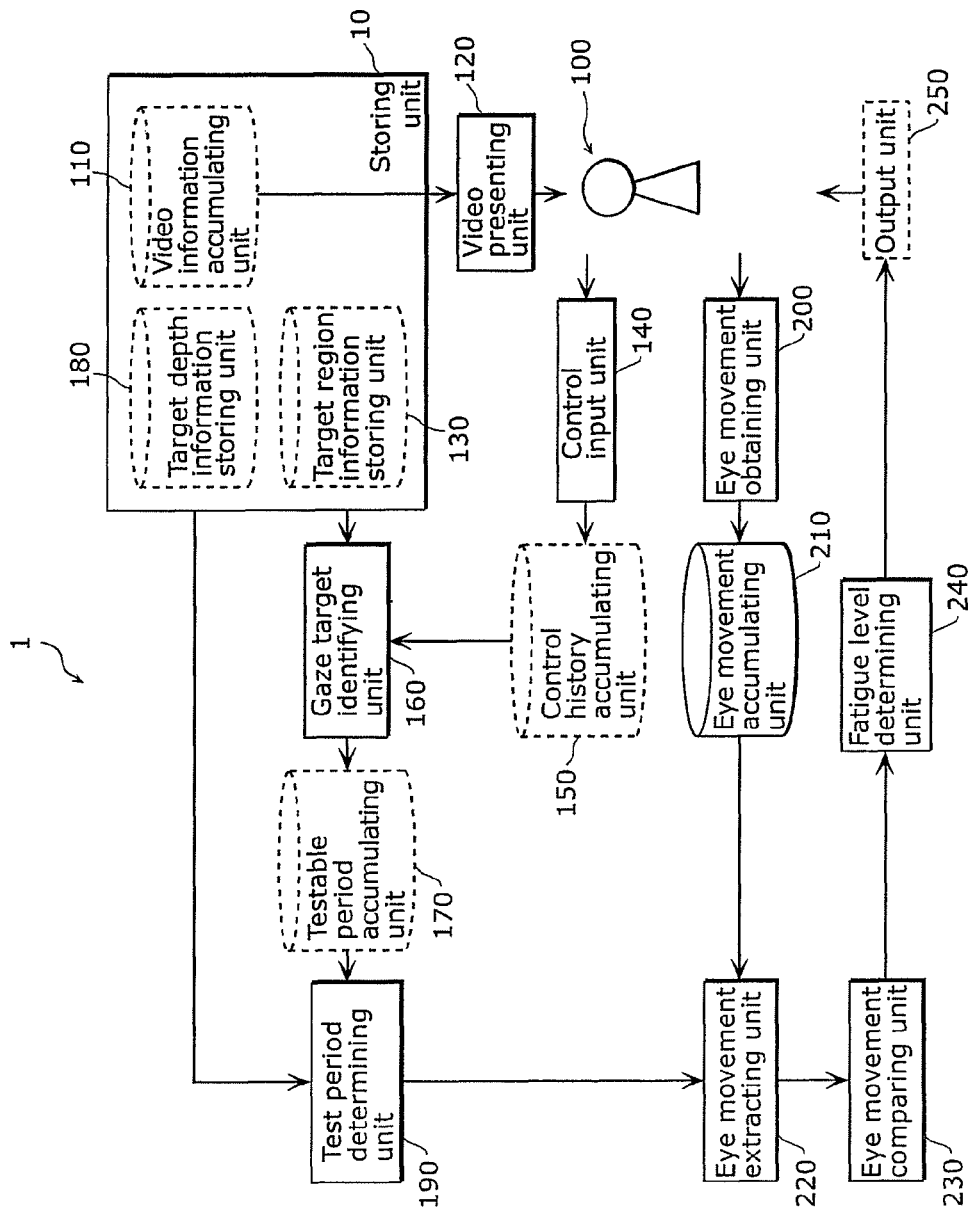
FIG. 3 is a block diagram illustrating an example of an overall structure of a game machine including a visual fatigue level measuring device according to Embodiment 1.

FIG. 3 is a diagram showing a structure of a visual fatigue level measuring device 1 according to Embodiment 1.

The visual fatigue level measuring device 1 is a device which measures the level of visual fatigue of a user who is viewing 3D video based on experimental results described with reference to FIG. 1 and FIG. 2A to FIG. 2D. The visual fatigue level measuring device 1 includes: a storing unit 10 which includes a video information accumulating unit 110, a target depth information storing unit 180 and a target region information storing unit 130; a gaze target identifying unit 160; a testable period accumulating unit 170; a test period determining unit 190; a video presenting unit 120; a control input unit 140; a control history accumulating unit 150; an eye movement obtaining unit 200; an eye movement accumulating unit 210; an eye movement extracting unit 220; an output unit 250; a fatigue level determining unit 240; and an eye movement comparing unit 230.

The video information accumulating unit 110 is, for example, a hard disk which accumulates video information for 3D video including left-eye video and right-eye video. Here, the video information accumulating unit 110 accumulates 3D video information to be presented to a player (user) 100 who plays games.

The video presenting unit 120 is, for example, a display device which presents, to the player 100, 3D video (left-eye video and right-eye video) based on the video information accumulated in the video information accumulating unit 110.

The target region information storing unit 130 is, for example, a hard disk which stores target region information which includes information for identifying each visual target in the 3D video indicated by the video information accumulated in the video information accumulating unit 110, and information indicating time at which each visual target is presented by the video presenting unit 120. Here, the target region information storing unit 130 stores information indicating time positions of visual targets included in the video information accumulated in the video information accumulating unit 110 and information indicating regions of the visual targets on the screen in the video.

The control input unit 140 is, for example, an input controller which receives control by the player 100 with respect to the presented 3D video. Here, the control input unit 140 is an apparatus used by the player 100 to input control with respect to the presented 3D video.

The control history accumulating unit 150 is, for example, a hard disk which accumulates information (control history) indicating the history of control that are input by the control input unit 140.

The gaze target identifying unit 160 is a processing unit which determines that, when the control input unit 140 receives a predetermined control, the player 100 was gazing at the visual target in the video presented by the video presenting unit 120 at the time when the predetermined control was received, by referring to the target region information stored in the target region information storing unit 130. Here, the gaze target identifying unit 160 identifies the visual target, in the video, at which the player 100 was gazing when the control was input, based on the information (control history) of a series of controls input by the player 100 accumulated in the control history accumulating unit 150 and the information (target region information) on time and the region of the visual targets stored in the target region information storing unit 130. In order for that, the gaze target identifying unit 160 generates information which indicates a testable period which is a time period during which the player 100 was gazing at the visual target.

The testable period accumulating unit 170 is, for example, a hard disk which accumulates information which indicates the visual target in the video and the time period (testable period) during which the player 100 was gazing at the visual target that are identified by the gaze target identifying unit 160.

The target depth information storing unit 180 is, for example, a hard disk, which stores depth information which indicates the depth of visual targets in the 3D video indicated by the video information accumulated in the video information accumulating unit 110.

The test period determining unit 190 is a processing unit which determines two or more time periods (test periods) for measuring the level of visual fatigue based on the depth changes of the visual targets identified by the gaze target identifying unit 160, by referring to the target depth information stored in the target depth information storing unit 180. Here, the test period determining unit 190 determines the time periods (test periods) of eye movement data used for measuring visual fatigue caused due to eye movements, based on the information for identifying the visual targets stored in the testable period accumulating unit 170 and the depth information of the visual targets stored in the target depth information storing unit 180. More specifically, the test period determining unit 190 determines, as test periods, two or more different time periods that have the same depth change among the depth changes of the visual targets identified by the gaze target identifying unit 160.

The eye movement obtaining unit 200 is a processing unit which obtains data indicating movements of the left and right eyes (eye movements) of the player 100 with respect to the video presented by the video presenting unit 120. Here, the eye movement obtaining unit 200 obtains eye movements performed while the player 100 is playing games.

The eye movement accumulating unit 210 is, for example, a hard disk which accumulates data (eye movement data) which indicates eye movements of the player 100 obtained by the eye movement obtaining unit 200.

The eye movement extracting unit 220 is a processing unit which extracts data indicating eye movements in each of the two or more time periods determined by the test period determining unit 190, from among the data accumulated in the eye movement accumulating unit 210. Here, the eye movement extracting unit 220 extracts data indicating the eye movements in the time periods from the eye movement accumulating unit 210 based on the time periods of the eye movement data to be used for measuring visual fatigue output by the test period determining unit 190.

The eye movement comparing unit 230 is a processing unit which compares the eye movements performed in two or more time periods, based on the data extracted by the eye movement extracting unit 220. Here, the eye movement comparing unit 230 compares eye movements in the periods extracted by the eye movement extracting unit 220.

The fatigue level determining unit 240 is a processing unit which determines the level of visual fatigue of the player 100 based on the results of the comparison by the eye movement comparing unit 230. Here, the fatigue level determining unit 240 determines the current visual fatigue of the player 100 based on the result of the comparison of the eye movements in the periods output by the eye movement comparing unit 230. More specifically, the fatigue level determining unit 240 determines that the level of fatigue is higher as the differences in the eye movements in two test periods increases.

The output unit 250 is, for example, a display device or an audio output device which outputs the level of visual fatigue determined by the fatigue level determining unit 240. Here, the output unit 250 outputs, to the player 100, the state of visual fatigue of the player 100 determined by the fatigue level determining unit 240.

It is to be noted that the video information accumulating unit 110, the target region information storing unit 130, the control history accumulating unit 150, the testable period accumulating unit 170, the target depth information storing unit 180, and the eye movement accumulating unit 210 are implemented by one or more storage media, such as memory (for example, nonvolatile memory devices such as hard disks as described above). Furthermore, the output unit 250 is, for example, an indicator which lights lamp, a loudspeaker which outputs warning noise, or a signal generating unit which generates warning messages to be presented by the video presenting unit 120.

Furthermore, in view of achieving the objects of the present disclosure, the visual fatigue level measuring device 1 does not always have to include the structural elements surrounded by the dashed lines in FIG. 3 (the video information accumulating unit 110, the target region information storing unit 130, the target depth information storing unit 180, the control history accumulating unit 150, the testable period accumulating unit 170, and the output unit 250). The video information accumulating unit 110, the target region information storing unit 130, and the target depth information storing unit 180 are not always necessary as long as the visual fatigue level measuring device 1 can obtain video information, target region information and target depth information from outside via telephone lines, the Internet or the like. In a similar manner, the control history accumulating unit 150 is not always necessary because the gaze of the player 100 can be determined by the gaze target identifying unit 160 receiving outputs from the control input unit 140 and determining in real time whether the player 100 is gazing at a visual target. In a similar manner, the testable period accumulating unit 170 is not always necessary because test periods are determined by the test period determining unit 190 receiving outputs from the gaze target identifying unit 160 and determining in real time whether the received outputs can be used as test periods. In a similar manner, the output unit 250 is not always necessary because the objects of the present disclosure are achieved by the fatigue level determining unit 240 accurately determining the level of fatigue of the player 100. The same are applied to the following exemplary embodiments and variations (FIG. 41, FIG. 43, FIG. 46A, and FIG. 49).

FIG. 4 shows an example of video information 110a accumulated in the video information accumulating unit 110. As shown in FIG. 4, the video information accumulating unit 110 accumulates, as the video information 110a, for example, time information starting from the start time of video, image information corresponding to the respective time points, and information indicating that the image is to be presented to the left eye or the right eye.

Figure 5:
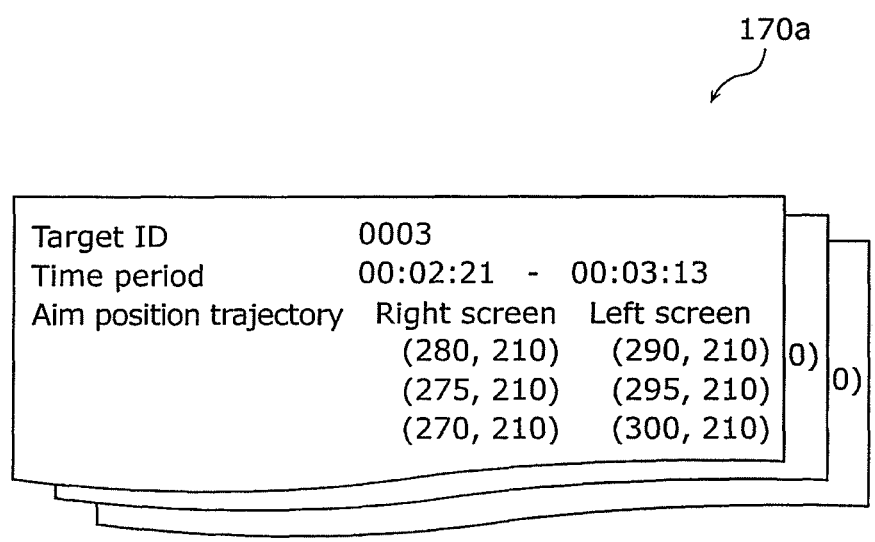
FIG. 5 shows an example of information indicating a testable period accumulated in a testable period accumulating unit shown in FIG. 3.

FIG. 5 shows an example of data 170a, that is, information indicating testable periods, accumulated in the testable period accumulating unit 170. As shown in FIG. 5, the data 170a, for example, includes: a target ID for identifying a visual target; a time period during which the player 100 was aiming at the visual target, that is, during which the player 100 was gazing at the visual target; and trajectories of the aim positions in the period during which the player 100 was aiming at the visual target.

Figure 6:
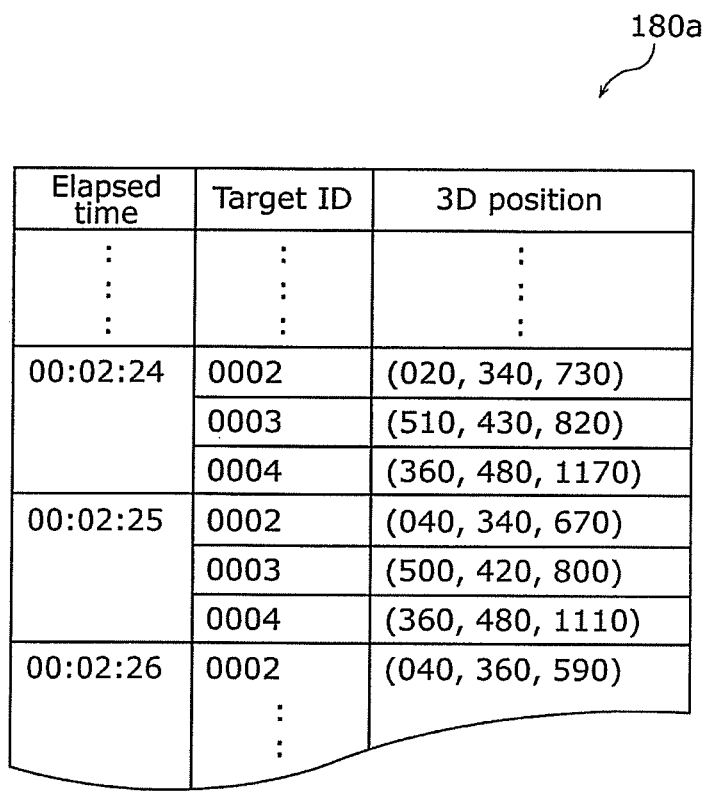
FIG. 6 shows an example of target depth information stored in a target depth information storing unit shown in FIG. 3.

FIG. 6 shows an example of target depth information 180a stored in the target depth information storing unit 180. As shown in FIG. 6, the target depth information 180a, for example, includes: IDs of respective targets displayed on the screen at a given time point, and 3D virtual positions of the targets.

FIG. 7 shows an example of target region information 130a stored in the target region information storing unit 130. As shown in FIG. 7, the target region information 130a, for example, includes: time information starting from the start time of video, IDs of targets included in images at respective time points, central coordinates of the targets in the right-eye screen, central coordinates of the targets in the left-eye screen, a sequence of coordinates of boundary lines of the targets in the right-eye screen, and a sequence of coordinates of boundary lines of the targets in the left-eye screen.

FIG. 8 shows an example of data (control history 150a) accumulated in the control history accumulating unit 150. As shown in FIG. 8, the control history 150a includes, for example, time information starting from the start time of video, details of controls by the player 100 at the respective time points, and positions on the screen of the control targets, such as the aim positions, at the respective time points.

FIG. 9 shows an example of data (eye movement data 210a) accumulated in the eye movement accumulating unit 210. As shown in FIG. 9, the eye movement data 210a includes, for example, time information starting from the start time of video, and coordinates of the centers of the pupils of the left and right eyes. Processing units such as the gaze target identifying unit 160, the test period determining unit 190, the eye movement extracting unit 220, the eye movement comparing unit 230, and the fatigue level determining unit 240 may be implemented by one or more CPUs and one or more memories. In other words, these processing units may be implemented by hardware such as a dedicated electric circuit (a semiconductor integrated circuit), or may be implemented by software such as a program executed by the CPU.

Figure 10:
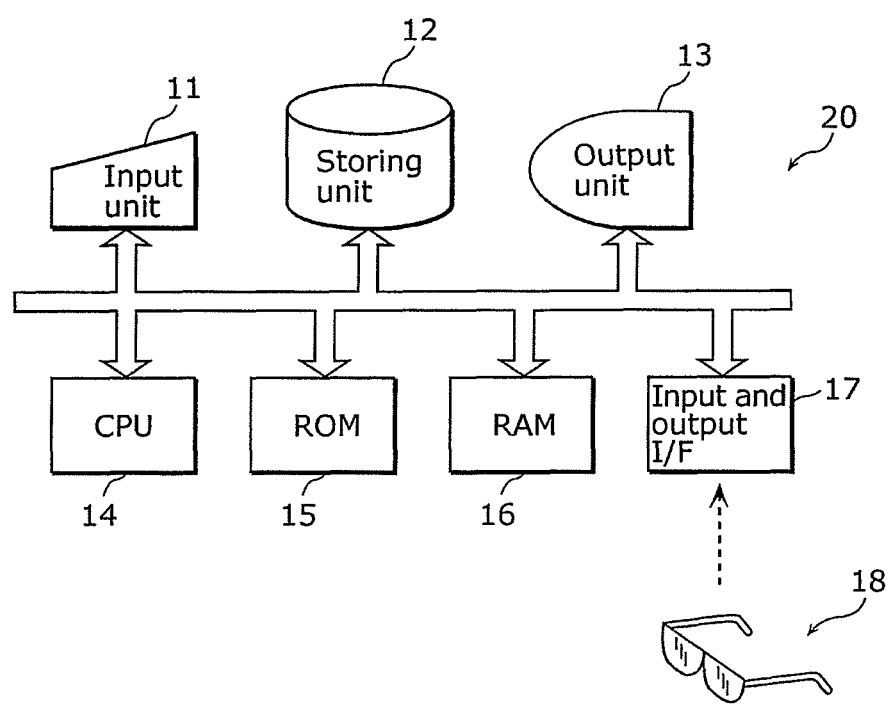
FIG. 10 is a block diagram illustrating a hardware configuration used when processing units included in the visual fatigue level measuring device according to Embodiment 1 is implemented by software.
Figure 13:
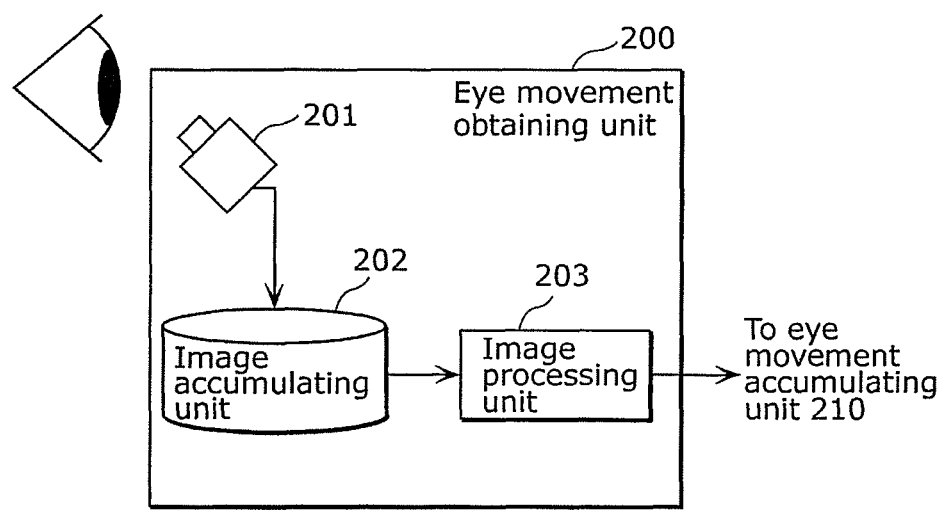
FIG. 13 is a block diagram illustrating an example of a detailed structure of an eye movement obtaining unit shown in FIG. 3.
Figure 25:
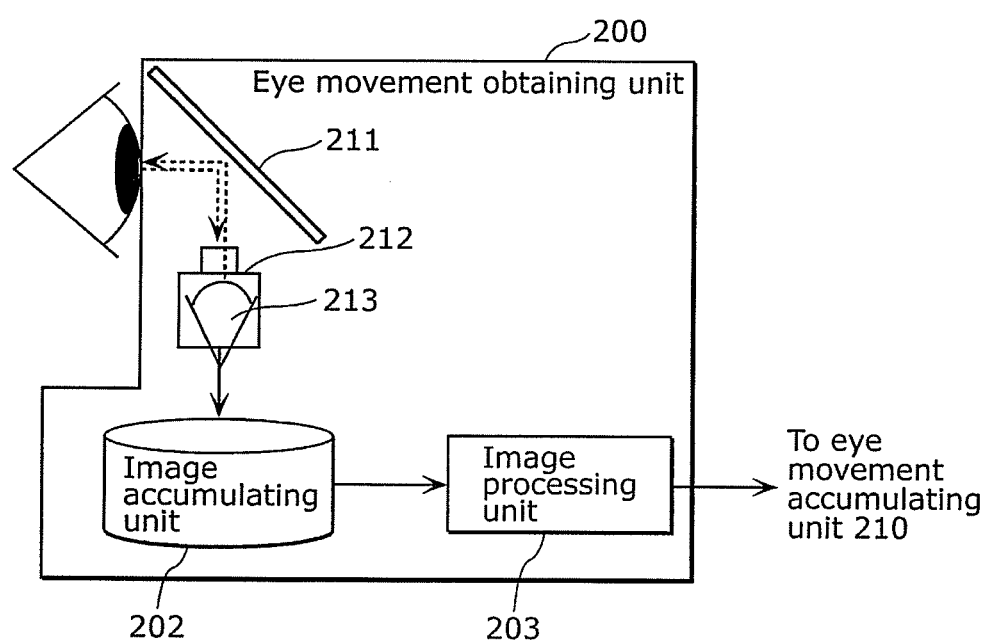
FIG. 25 is a block diagram illustrating another example of a detailed structure of the eye movement obtaining unit shown in FIG. 3.

FIG. 10 is a block diagram illustrating a hardware configuration used when the processing units of the visual fatigue level measuring device 1 according to Embodiment 1 is implemented by software. In the case where the processing units of the visual fatigue level measuring device 1 according to Embodiment 1 are implemented by software, as shown in FIG. 10, the visual fatigue level measuring device 1 may be implemented by a computer 20 which includes: an input unit 11 such as a keyboard or a mouse; a storing unit 12 such as a hard disk; an output unit 13 such as a display device; a CPU 14; a ROM 15; a RAM 16; an input and output interface (I/F) 17 which inputs and outputs signals to and from an external device; and 3D glasses 18 which includes the eye movement obtaining functions as shown in FIG. 1, and FIG. 13 and FIG. 25 which will be described later. More specifically, the control input unit 140 in FIG. 3 is mainly implemented by the input unit 11 included in the computer 20. The video presenting unit 120 and the output unit 250 in FIG. 3 are mainly implemented by the output unit 13 included in the computer 20. The control input unit 140 in FIG. 3 is mainly implemented by the 3D glasses 18 and the input and output I/F 17 included in the computer 20. The storing unit 10 in FIG. 3 is mainly implemented by the storing unit 12 included in the computer 20. The other processing units (the gaze target identifying unit 160, the test period determining unit 190, the eye movement extracting unit 220, the eye movement comparing unit 230, and the fatigue level determining unit 240) are implemented by the CPU 14 performing execution in accordance with programs stored in the ROM 15 or the storing unit 12 included in the computer 20 while using the RAM 16 as a temporal storage area.

Figure 11:
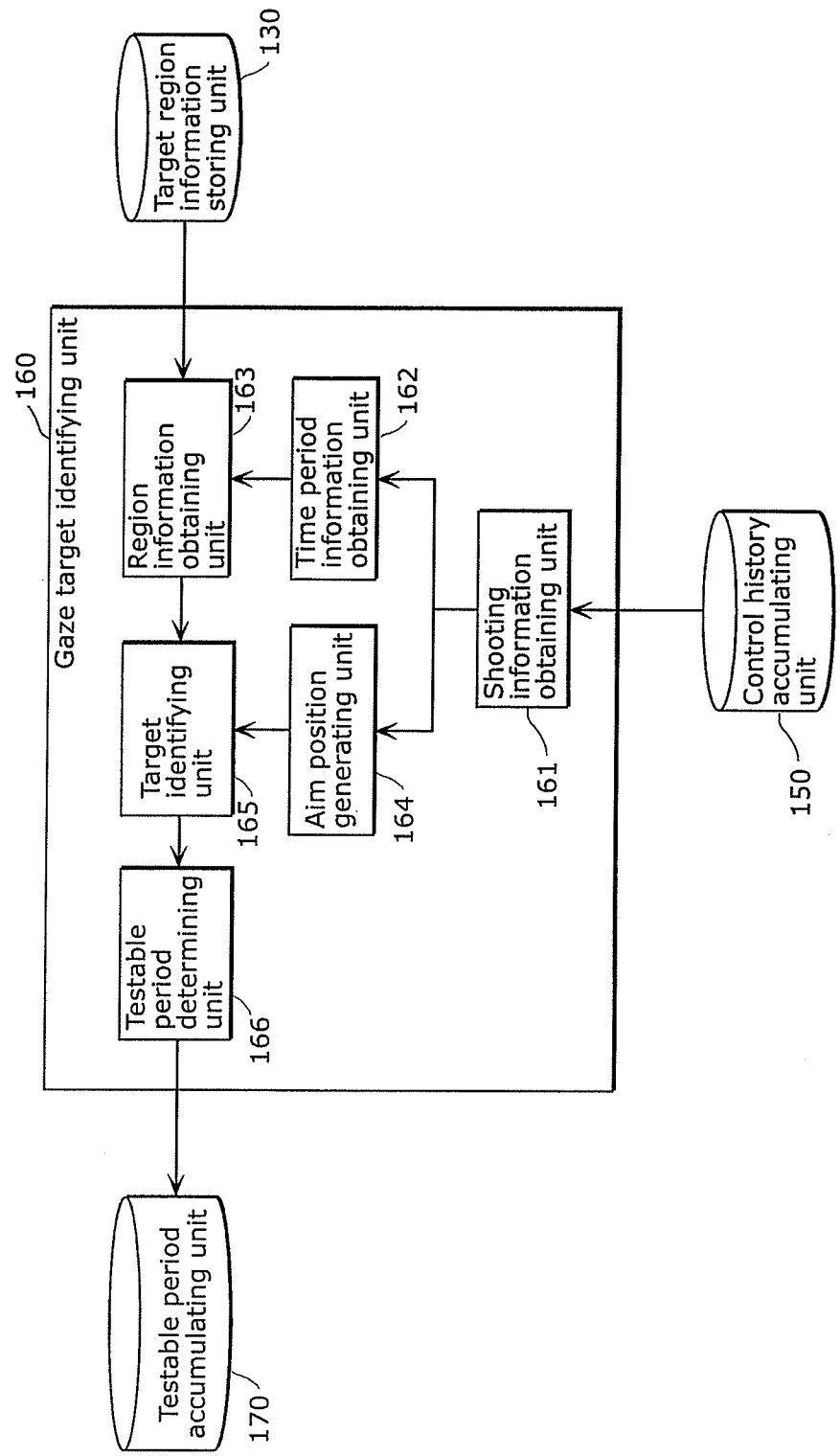
FIG. 11 is a block diagram illustrating an example of a detailed structure of a gaze target identifying unit shown in FIG. 3.

FIG. 11 shows a detailed structure of the gaze target identifying unit 160 according to Embodiment 1.

In Embodiment 1, a description is given of the visual fatigue level measuring device 1 with an example of a game including shooting scenes. As shown in FIG. 11, the gaze target identifying unit 160 includes: a shooting information obtaining unit 161 which obtains shooting information from a series of control inputs (control history 150a) accumulated in the control history accumulating unit 150; a time period information obtaining unit 162 which obtains time period information of shooting from shooting information obtained by the shooting information obtaining unit 161; a region information obtaining unit 163 which extracts region information of visual targets (target region information 130a) from the target region information storing unit 130 according to the time period output by the time period information obtaining unit 162; an aim position generating unit 164 which generates information indicating the aim position at which the player 100 performed shooting control, from the shooting information obtained by the shooting information obtaining unit 161; a target identifying unit 165 which identifies the visual target at which the player 100 aimed, based on the information indicating the aim position output by the aim position generating unit 164 and the region information of the visual target extracted by the region information obtaining unit 163; and a testable period determining unit 166 which determines, as a testable period, the time period during which the player 100 was aiming at the visual target identified by the target identifying unit 165. The testable period determining unit 166 outputs, to the testable period accumulating unit 170, the data 170a which indicates testable periods. The data 170a output here includes information indicating time periods corresponding to the testable periods, the target IDs of the targets at which the player 100 was aiming, and trajectories of the aim positions.

Figure 12:
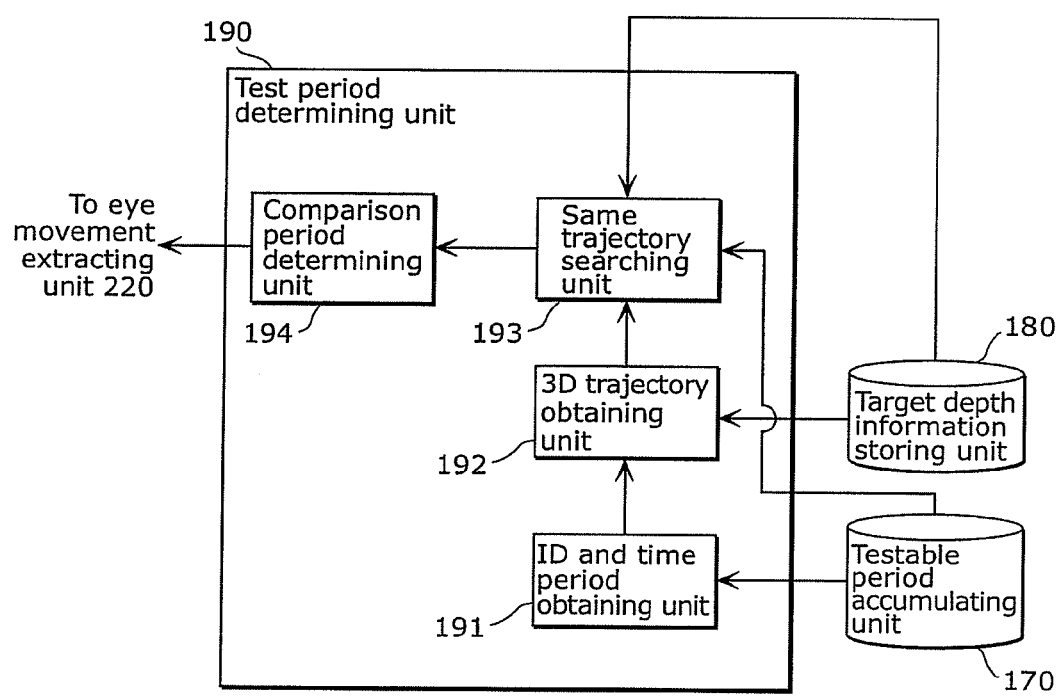
FIG. 12 is a block diagram illustrating an example of a detailed structure of a test period determining unit shown in FIG. 3.

FIG. 12 shows a detailed structure of the test period determining unit 190 shown in FIG. 3.

The test period determining unit 190 includes: an ID and time period obtaining unit 191 which obtains information (ID) for identifying the visual target at which the player 100 was gazing during the most recent testable period among the testable periods indicated by the data 170a stored in the testable period accumulating unit 170 and information indicating the time period during which the player 100 was gazing at the visual target; a 3D trajectory obtaining unit 192 which obtains, according to the information indicating the ID of the visual target and the time period obtained by the ID and time period obtaining unit 191, information (target depth information 180a) which indicates trajectories of 3D virtual positions of the visual target at which the player 100 was gazing from the target depth information storing unit 180; a same trajectory searching unit 193 which extracts, from the target depth information storing unit 180 and the testable period accumulating unit 170, information for identifying a testable visual target which has the same trajectory as the trajectory of the visual target in the most recent testable period indicated by the information obtained by the 3D trajectory obtaining unit 192; and a comparison period determining unit 194 which determines, as test periods, periods (comparison periods) used for comparing eye movements from among the testable periods which have the same trajectories indicated by the information extracted by the same trajectory searching unit 193.

FIG. 13 shows a detailed structure of the eye movement obtaining unit 200 shown in FIG. 3.

The eye movement obtaining unit 200 includes: a camera 201 for capturing images of the left and right eyes of the player 100; an image accumulating unit 202 which accumulates the images obtained by the camera 201; and an image processing unit 203 which processes the images of the eyes accumulated in the image accumulating unit 202 to calculate the center positions of the pupils of the left and right eyes. Although FIG. 13 schematically shows only one eye, it may be that the camera 201 is arranged for each of the left and right eyes to record right eye images and left eye images. It may also be that a single camera records images of both left and right eyes and the image processing unit 203 separately processes the images of the left and right eyes. The camera 201 may be provided to the frames of the stereoscopic shutter glasses, or may be provided to the frame or the like of the display screen.

Figure 14:
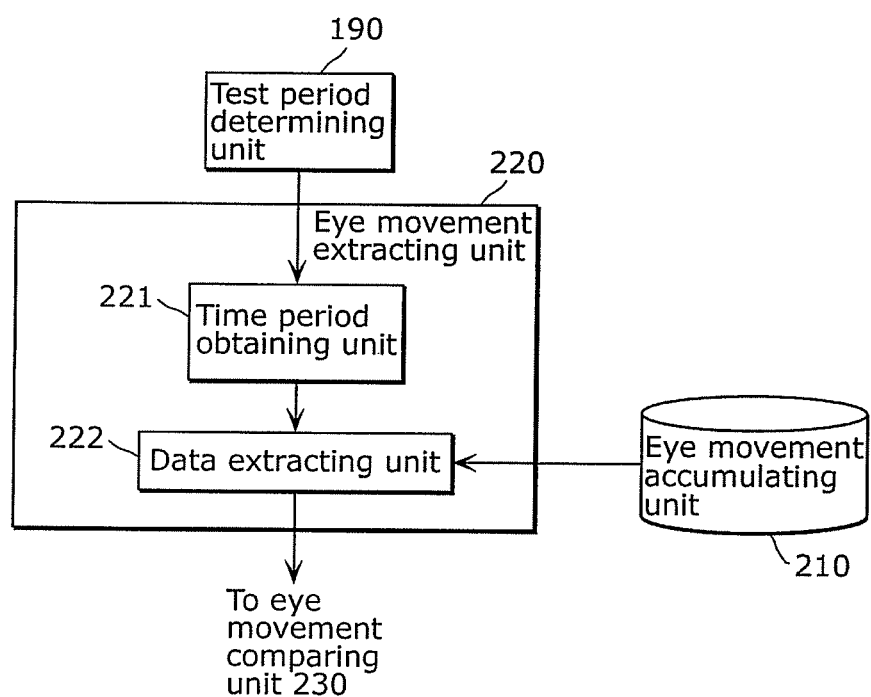
FIG. 14 is a block diagram illustrating an example of a detailed structure of an eye movement extracting unit shown in FIG. 3.

FIG. 14 shows a detailed structure of the eye movement extracting unit 220 shown in FIG. 3.

The eye movement extracting unit 220 includes: a time period obtaining unit 221 which obtains information of time periods for tests (test periods) output by the test period determining unit 190; and a data extracting unit 222 which extracts eye movement data based on the information of each time period obtained by the time period obtaining unit 221, from the eye movement data 210a accumulated in the eye movement accumulating unit 210.

Figure 15:
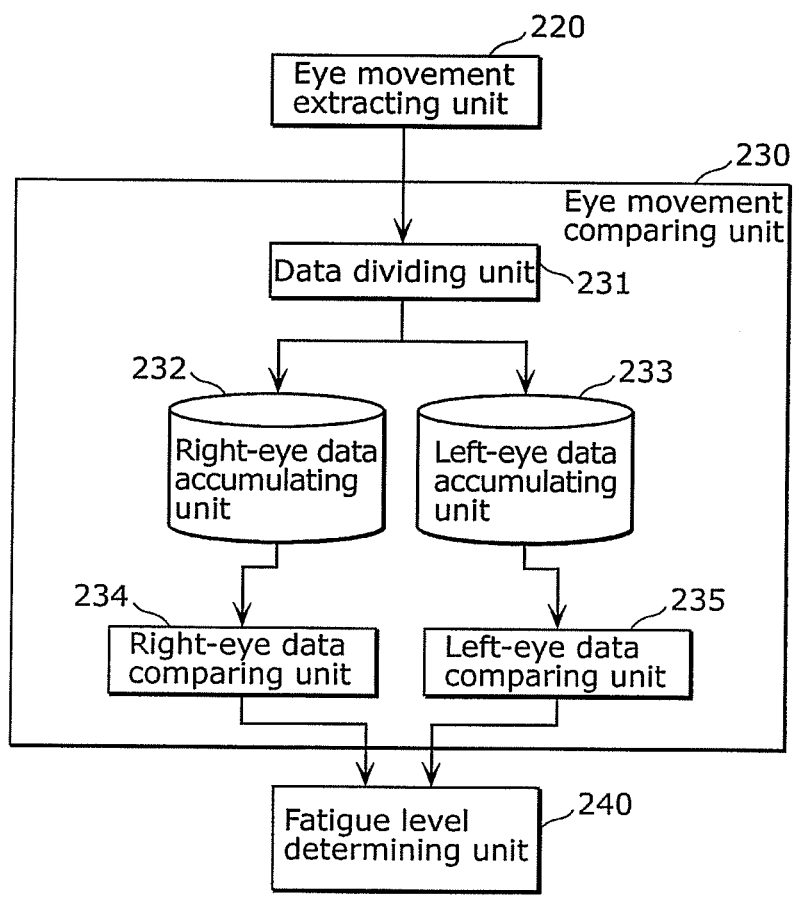
FIG. 15 is a block diagram illustrating an example of a detailed structure of an eye movement comparing unit shown in FIG. 3.

FIG. 15 shows a detailed structure of the eye movement comparing unit 230 shown in FIG. 3.

The eye movement comparing unit 230 includes: a data dividing unit 231 which obtains eye movement data corresponding to each test time period obtained by the eye movement extracting unit 220, and divides the obtained data into left-eye information and right-eye information; a right-eye data accumulating unit 232 which accumulates eye movement data of the right eye obtained by the data dividing unit 231; a left-eye data accumulating unit 233 which accumulates eye movement data of the left eye obtained by the data dividing unit 231; a right-eye data comparing unit 234 which compares eye movements in the test periods based on the eye movement data accumulated in the right-eye data accumulating unit 232; and a left-eye data comparing unit 235 which compares eye movements in the test periods based on the eye movement data accumulated in the left-eye data accumulating unit 233.

Figure 16:
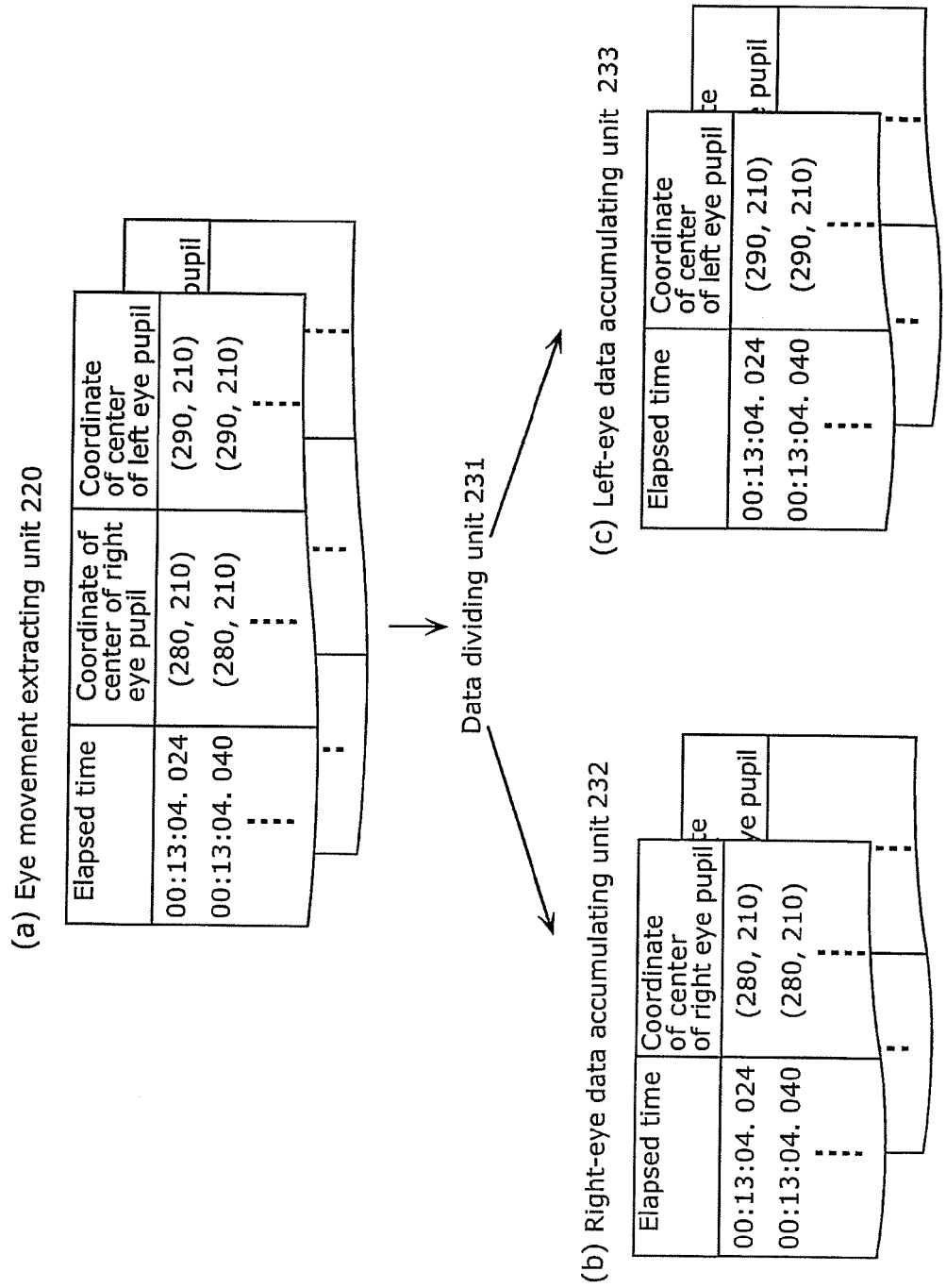
FIG. 16 shows an example of data accumulated in a right-eye data accumulating unit and a left-eye data accumulating unit shown in FIG. 15.

FIG. 16 shows an example of data accumulated in the right-eye data accumulating unit 232 and the left-eye data accumulating unit 233 shown in FIG. 15. In FIG. 16, (a) shows an example of the eye movement data extracted by the eye movement extracting unit 220 (more specifically, the data extracting unit 222). Here, (a) shows elapsed time from the start of the game and central coordinates of the pupils of both eyes corresponding to the respective time points, extracted from the eye movement accumulating unit 210 based on the test time period. The data dividing unit 231 divides such eye movement data into left-eye data and right-eye data. The right-eye data accumulating unit 232 accumulates only elapsed time and right-eye data, and the left-eye data accumulating unit 233 accumulates only elapsed time and left-eye data. The coordinates of the centers of the pupils are represented in a unit of pixel in the similar manner as the eye movement data 210a accumulated in the eye movement accumulating unit 210. The right-eye data accumulating unit 232 and the left-eye data accumulating unit 233 accumulate such eye movement data for each of the determined time periods.

Figure 17:
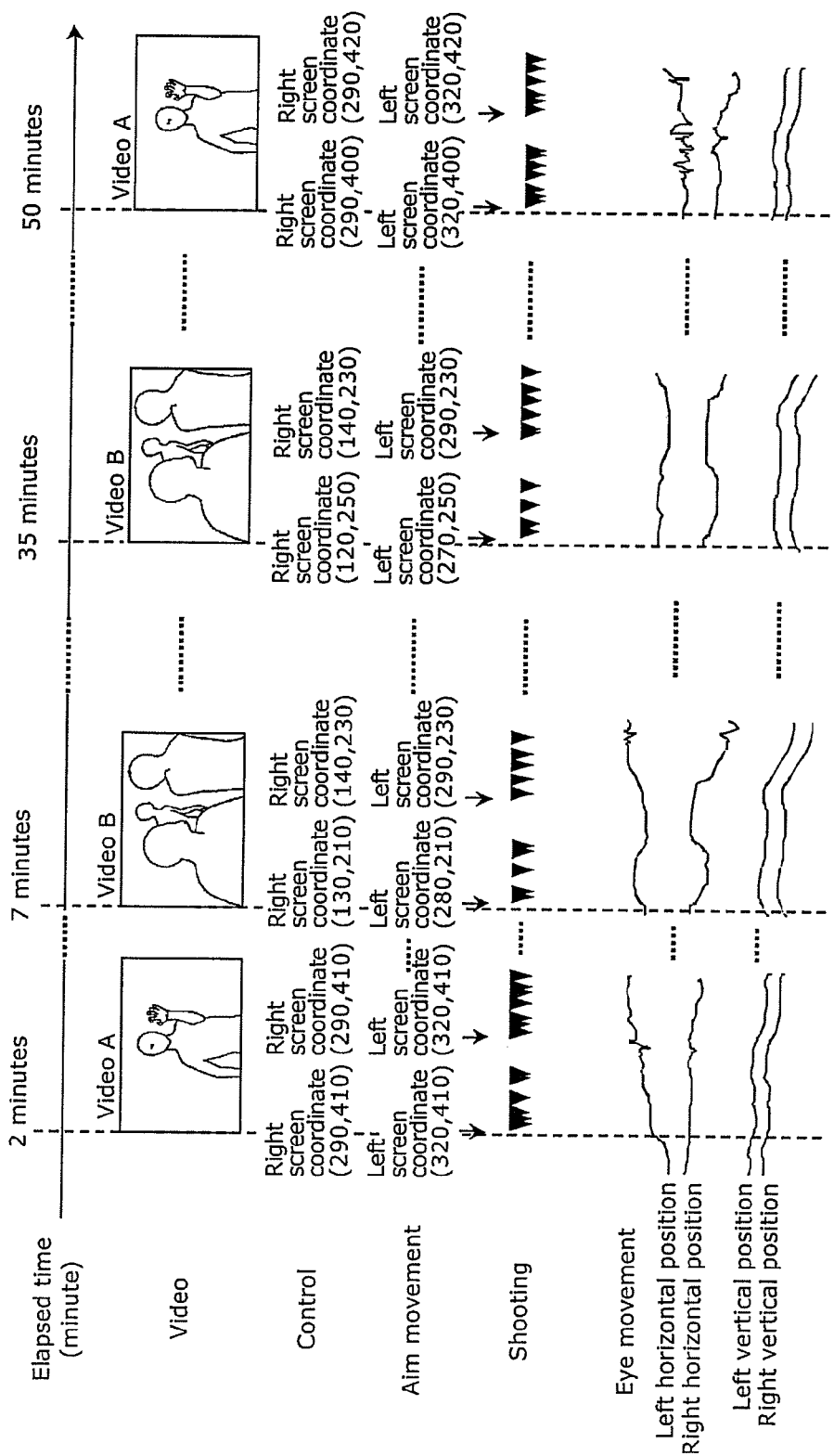
FIG. 17 is a schematic diagram illustrating temporal relationship between video, player control, and measurement results of eye movements of the player.

FIG. 17 schematically shows temporal relationship between video (3D video presented to the player 100), controls by the player 100, and measurement results of eye movements of the player 100. The top line indicates the elapsed time from the start of the game, the following line indicates the images ("video" in FIG. 17) corresponding to each elapsed time, and the line under that indicates the controls by the player 100 corresponding to each elapsed time. Here, as an example of the controls, movement of the aim position in shooting is indicated by the downward arrows, and the coordinates of the movement results are shown. Furthermore, the execution of shooting as a control is indicated by downward triangles. The lowermost line indicates the eye movements represented as the movements of the horizontal positions and the vertical positions of the centers of the pupils. With respect to the horizontal positions, the horizontal axis indicates time in the same manner in FIG. 2A to FIG. 2C, and the vertical axis indicates the positions on the horizontal axis of the coordinates of the eye images. With respect to the vertical positions, the horizontal axis also indicates time, and the vertical axis indicates the positions on the vertical axis of the coordinates of the eye images.

FIG. 17 shows the following history. After 2 minutes from the start of the game, video A was presented, and at that time the player 100 aimed at the visual target, and performed rapid fire. After 7 minutes from the start of the game, video B was presented, the player 100 aimed at the visual target having the smallest depth among visual targets, adjusted the aim position a couple of times, and then shot the visual target. After 35 minutes from the start of the game, the video B was presented again, the player 100 again aimed at the visual target having the smallest depth among visual targets, and shot the visual target. The trajectory of the visual target in the video B is the same at the elapsed time of 7 minutes and as of that at 35 minutes. The visual fatigue level measuring device 1 extracts eye movements performed when the player 100 aimed at the visual target having the same trajectory for performing rapid fire (that is, eye movements performed when the player 100 gazed at the visual target) and compares the eye movements performed at 7 minutes after the start of the game and the eye movements performed at 35 minutes after the start of the game. The eye movements can be compared because the trajectories of the visual targets are the same and the visual targets at which the player 100 gazed can be determined based on the controls of aiming and shooting. The eye movements start to be accumulated immediately after the start of the game; and thus, the eye movements at any elapsed time can be used for comparison. In the example of FIG. 17, the video A is presented again after 50 minutes from the start of the game, and the player 100 aimed at the visual target and performed rapid fire. With this, the eye movements can be compared between the elapsed time of 2 minutes and the elapsed time of 50 minutes. As shown in the example of FIG. 17, by comparing the eye movements at the elapsed time of 7 minutes and the eye movements at the elapsed time of 35 minutes in both of which the player 100 gazed at the visual target in the video B, it is shown that at the elapsed time of 35 minutes, the horizontal eye movements are smaller and the eye movements do not follow the trajectory of the visual target in the depth direction. Furthermore, by comparing the eye movements at the elapsed time of 2 minutes and the eye movements at the elapsed time of 50 minutes in both of which the player 100 gazed at the video A, it is shown that at the elapsed time of 50 minutes, horizontal eye movements are unstable and the eye movements do not follow the trajectory of the visual target in the depth direction. In this way, by comparing the eye movements performed immediately after the start of the game and the eye movements performed after a certain amount of time elapsed from the start of the game, it is possible to detect fatigue of the player 100.

Figure 18:
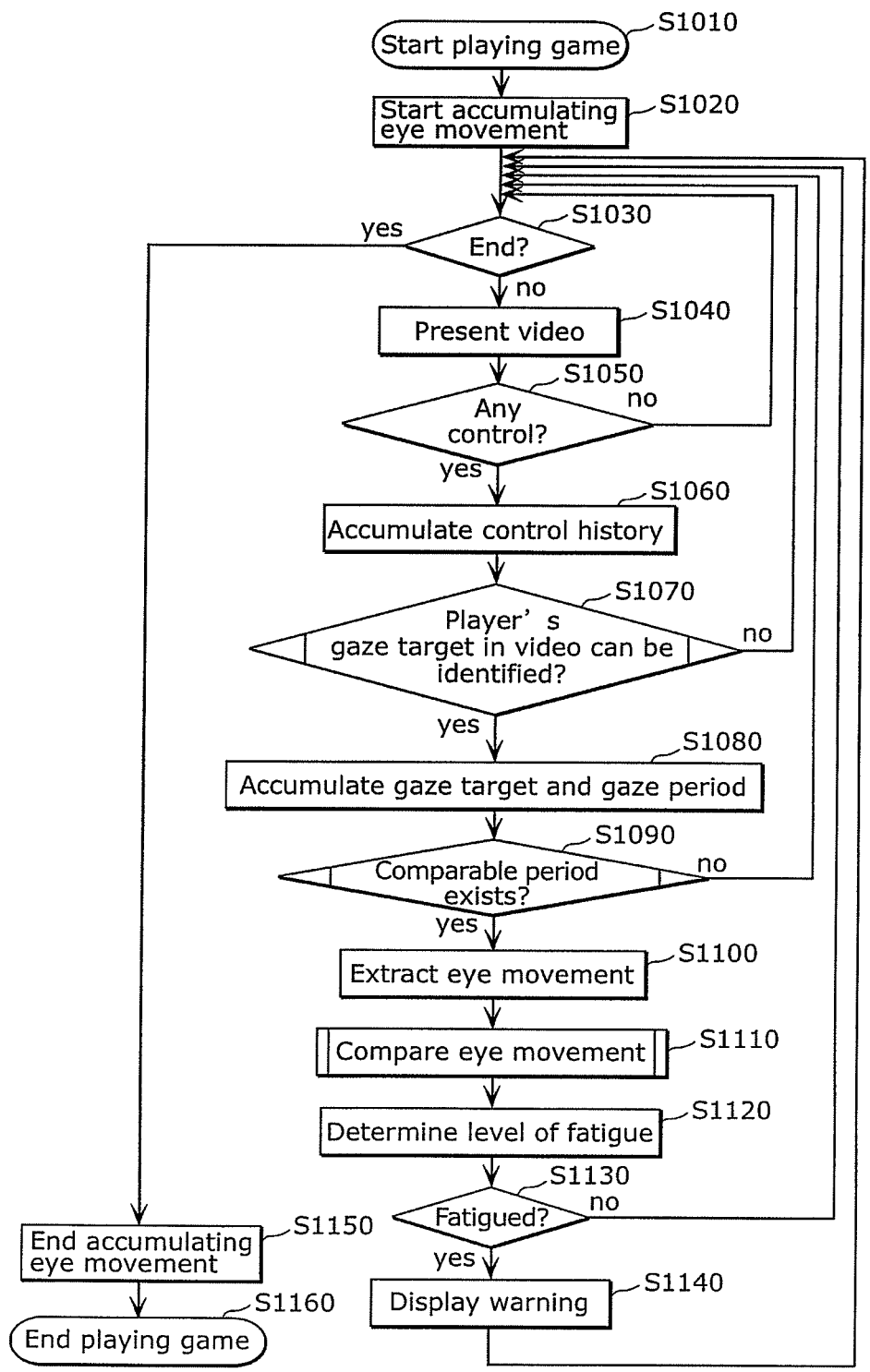
FIG. 18 is a flowchart of an example of operations of a game machine including the visual fatigue level measuring device according to Embodiment 1.
Figure 19:
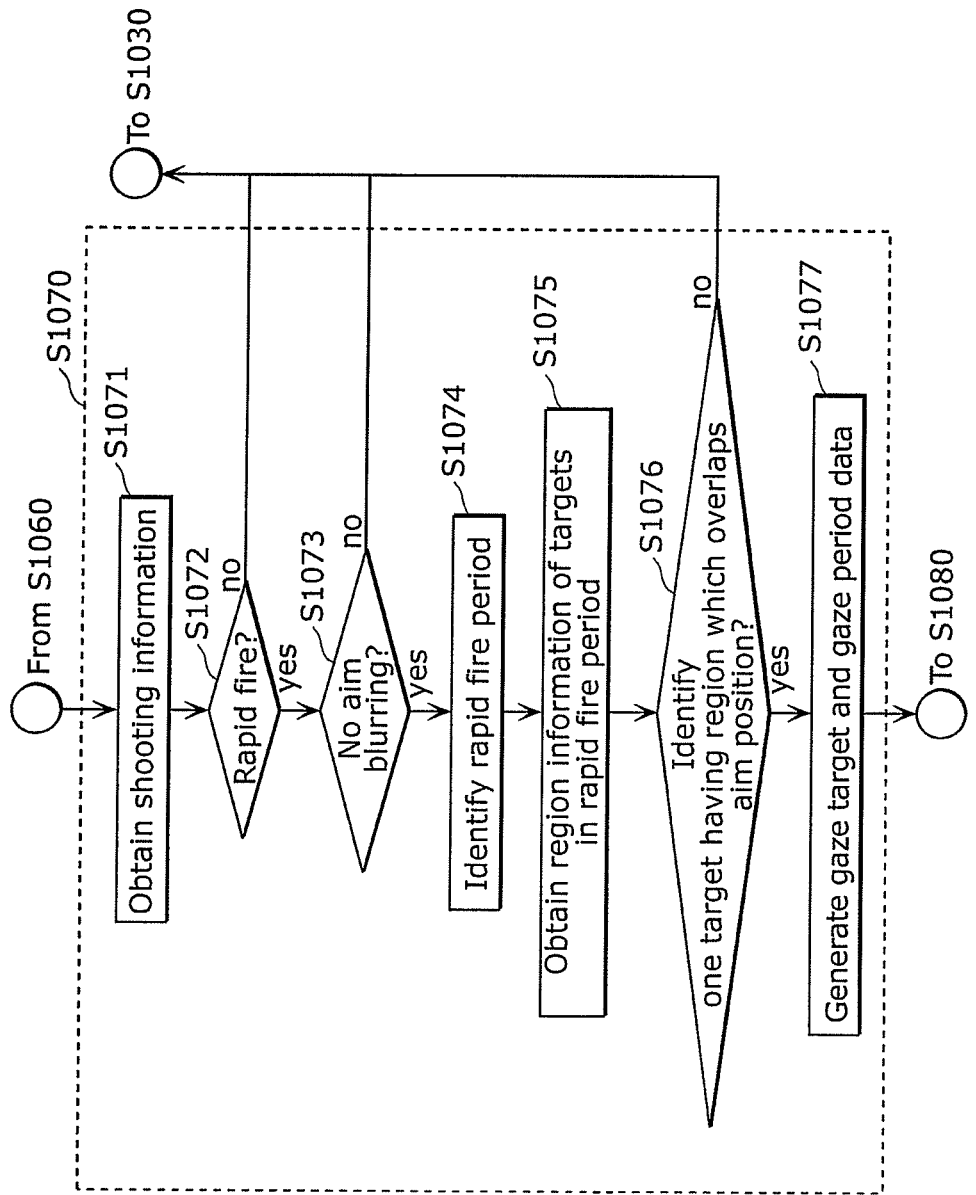
FIG. 19 is a flowchart of an example of the flow of the detailed processes in a target identifying step (Step S1070 in FIG. 18) according to Embodiment 1.
Figure 20:
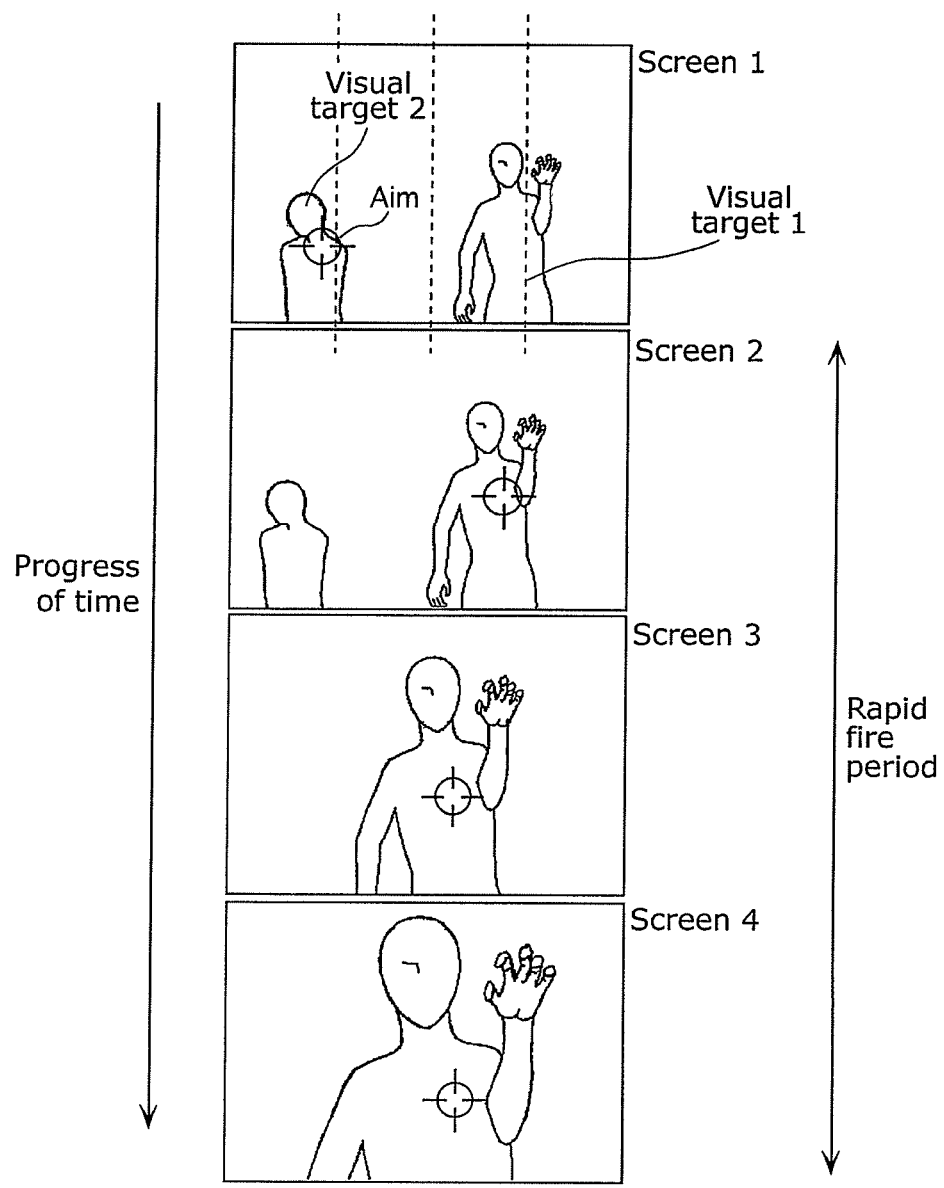
FIG. 20 is a schematic diagram illustrating an example of relationship between output video and control input in the target identifying step according to Embodiment 1.
Figure 21:
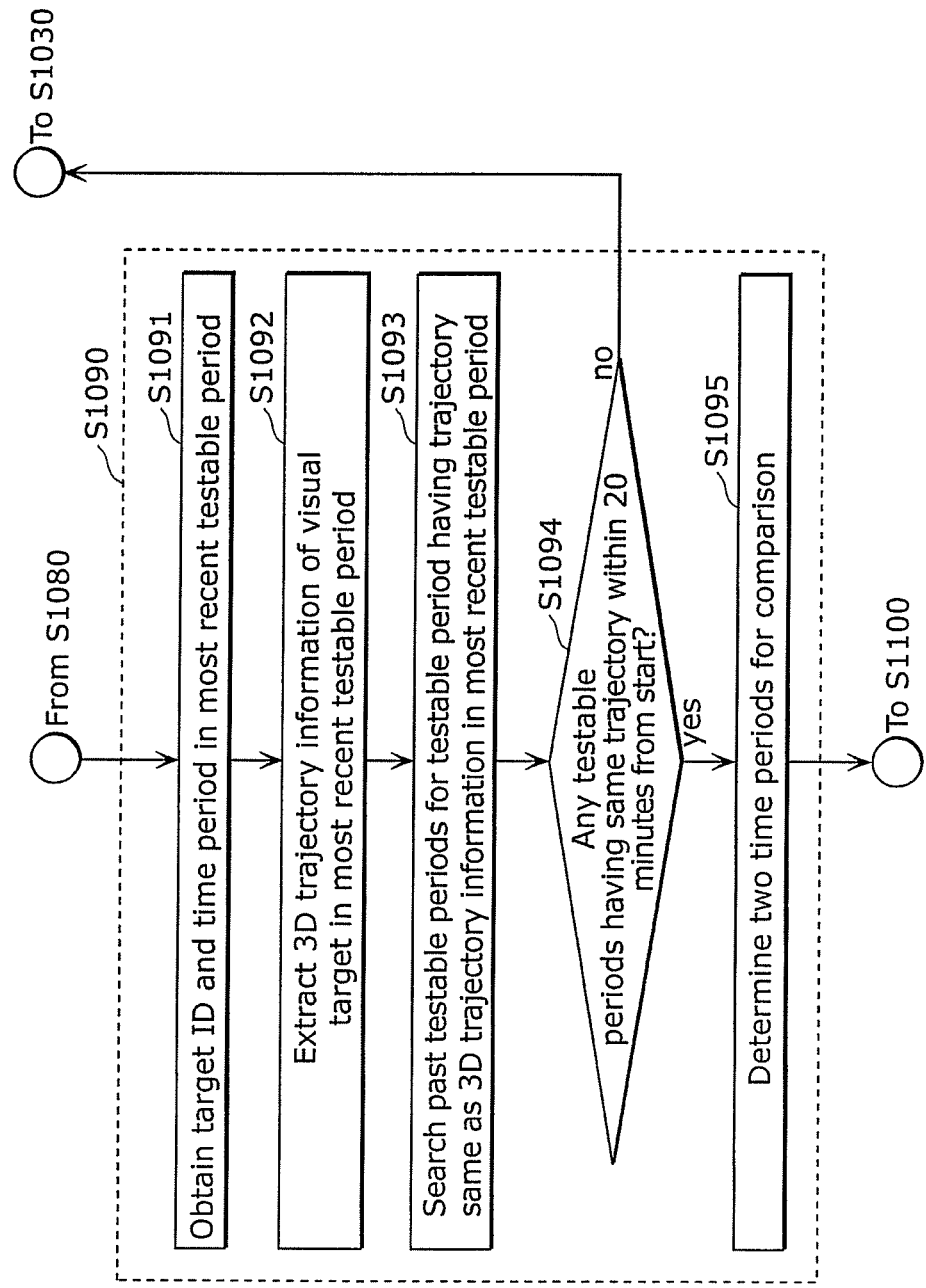
FIG. 21 is a flowchart of an example of the flow of the detailed processes in a comparable period extracting step (Step S1090 in FIG. 18) according to Embodiment 1.
Figure 23:
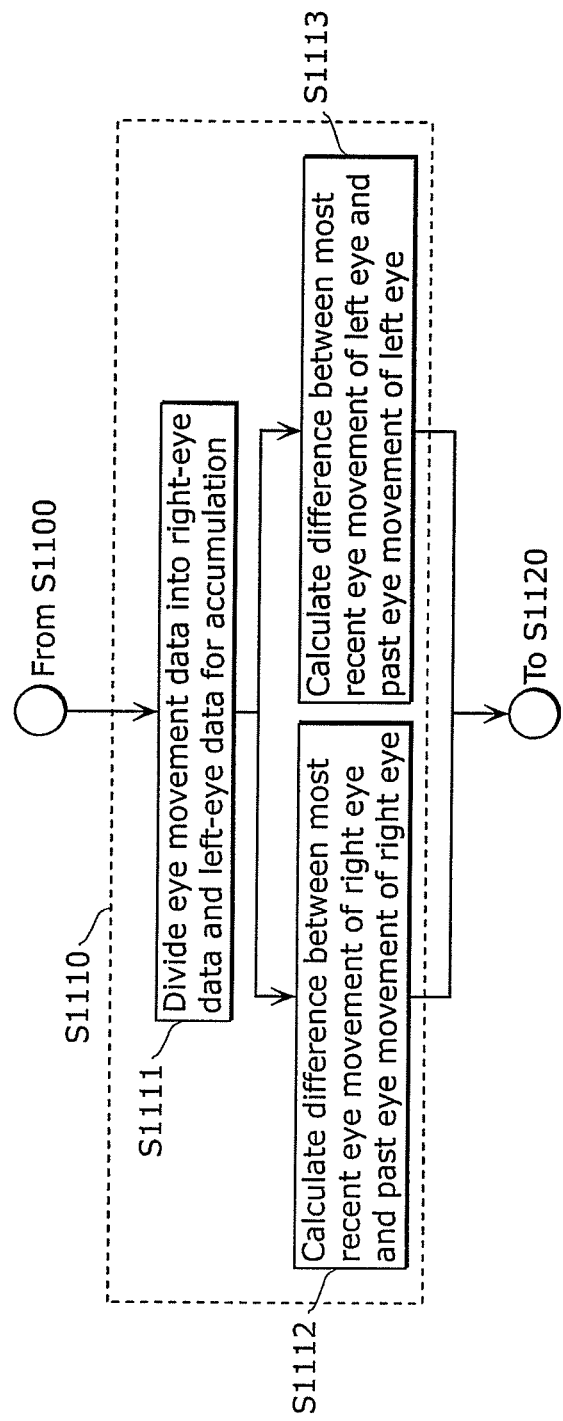
FIG. 23 is a flowchart of an example of the flow of the detailed processes in an eye movement comparing step (Step S1110 in FIG. 18) according to Embodiment 1.

FIG. 18 is a flowchart of the processes performed by the visual fatigue level measuring device 1 according to Embodiment 1. FIG. 19, FIG. 21, and FIG. 23 show details of part of the processes performed by the visual fatigue level measuring device 1. The following describes the processes with reference to FIG. 18 to FIG. 21.

First, the player 100 inputs a command for starting a game by an input unit that is not shown, and starts the game (S1010). When the game starts, the eye movement obtaining unit 200 starts measuring eye movements of both eyes, and accumulates the measurement results as the eye movement data 210*a* in the eye movement accumulating unit 210 (S1020).

The eye movement obtaining unit 200 checks if a command for ending the game has been input by the input unit that is not shown (S1030). In Step S1030, when the command for ending the game has been input (Yes in S1030), the process proceeds to Step S1150, and the eye movement obtaining unit 200 ends recording the eye movements (S1150). After ending the recording of the eye movements, the game ends (S1160).

On the other hand, when no command for ending the game has been input in Step S1030 (No in S1030), the process proceeds to Step S1040. In S1040, the video presenting unit 120 presents, to the player 100, video based on the video information 110*a* accumulated in the video information accumulating unit 110 (S1040). The control input unit 140 checks if the player 100 has performed any controls with respect to the video presented in Step S1040 (S1050). When the player 100 has performed no control in Step S1050 (No in S1050), the process returns to Step S1030. On the other hand, when the player 100 has performed controls in step S1050 (Yes in S1050), the control input unit 140 accumulates a series of controls (control history 150*a*) input in Step S1050, in the control history accumulating unit 150 (S1060). The control history 150*a* includes, as shown in FIG. 8, types of controls, control states, and control time information. For example, the control history 150*a* includes "shoot" as one type of controls, "aim position" as a control state, and "elapsed time from the start of the game" as time information. In Embodiment 1, an example of a game is used which includes shooting scenes. Here, a description is given of controls for rapid fire as an example of a series of controls. The rapid fire refers to a state where successive shooting controls are performed, and where the interval between each shooting is, for example, less than 500 ms. The gaze target identifying unit 160 identifies a visual target based on the display regions of the visual targets in the video that was being presented at the time of rapid fire, and based on information of the aim positions in the rapid fire controls (control history 150*a*) accumulated in the control history accumulating unit 150 in Step S1060. More specifically, when the player 100 keeps aiming at a single visual target for a predetermined period of time or more, for example, for two seconds or more, it means that the player 100 keeps gazing at the visual target. The gaze target identifying unit 160 then determines if it is possible to identify the target at which the player 100 keeps gazing for a predetermined period of time or more (S1070).

When it is possible to identify the target at which the player 100 keeps gazing in Step S1070 (Yes in S1070), the testable period accumulating unit 170 accumulates, as the data 170*a* indicating a testable period, an ID for identifying the visual target at which the player 100 kept gazing and information indicating the time period during which the player 100 was gazing at the visual target (S1080). On the other hand, when it is not possible to identify the target at which the player 100 kept gazing for a predetermined period of time or more in Step S1070 (No in S1070), the process returns to Step S1030.

The test period determining unit 190 then extracts, from the target depth information storing unit 180, the trajectory of the virtual positions of the virtual target at which the player 100 kept gazing (target depth information 180*a*) in the most recent testable period in the data 170*a* accumulated in the testable period accumulating unit 170, and searches the testable period accumulating unit 170 for a time period during which the player 100 was gazing at the visual target having the same trajectory as the trajectory of the visual target in the extracted most recent testable period, in Step S1080. In Embodiment 1, with an assumption that the player 100 was not fatigued at the time of the start of the game, fatigue is detected by comparing the eye movements in the time period that is within a predetermined period of time from the start of the game and the eye movements in the most recent testable period. When the test period determining unit 190 searches the testable period accumulating unit 170 for a time period during which the player 100 was gazing at the visual target having the same trajectory as the trajectory of the visual target in the most recent testable period, the test period determining unit 190 searches, for example, testable periods accumulated 20 minutes after the start of the game. The test period determining unit 190 determines if a time period exists during which the player 100 was gazing at the visual target having the same trajectory as the trajectory of the visual target in the most recent testable period (S1090).

When a time period exists during which the player 100 was gazing at the visual target having the same trajectory as the trajectory of the visual target in the most recent testable period (Yes in S1090), the eye movement extracting unit 220 extracts, from the eye movement accumulating unit 210, eye movement data of the most recent testable period and the time period during which the player 100 was gazing at the visual target having the same trajectory as the trajectory of the visual target in the most recent testable period (S1100). On the other hand, when no time period exists during which the player 100 was gazing at the visual target having the same trajectory as the trajectory of the visual target in the most recent testable period in Step S1090, the process returns to Step S1030.

With respect to the eye movement data extracted in Step S1100, the eye movement comparing unit 230 compares the eye movements in the most recent testable period and the eye movements performed within 20 minutes from the start of the game (S1110). The fatigue level determining unit 240 determines the level of fatigue based on the difference of the eye movements, obtained in Step S1110, between the most recent testable period and within 20 minutes from the start of the game (S1120).

The output unit 250 then determines if the level of fatigue determined in Step S1120 exceeds a predetermined value (S1130). For example, the level of fatigue is determined by three levels: no fatigue; fatigue symptoms; and fatigued. In this case, when the level of fatigue is fatigue symptoms or higher (Yes in S1130), the output unit 250 gives, to the player 100, a warning, indicating that the player 100 is having visual fatigue, on a display screen, by audio presentation headphones, or a loud speaker that are not shown (S1140), and the process returns to Step S1030. On the other hand, when the level of fatigue does not exceed the predetermined value in Step S1130 (No in S1130), the process returns to Step S1030. While the player 100 is playing the game, Steps S1030 to S1140 are repeatedly performed.

Now, referring to FIG. 19, a detailed description is given of Step S1070 in FIG. 18 (process for identifying the target at which the player 100 is gazing). The shooting information obtaining unit 161 obtains a series of shooting controls that are most recently made, from the control history 150a accumulated in the control history accumulating unit 150 in Step S1060 (S1071). The shooting information obtaining unit 161 determines if the series of shooting controls includes rapid fire, that is, a period during which each shooting control is performed at an interval of less than 500 ms (S1072). When the obtained controls included no rapid fire period in Step S1072 (No in S1072), the process returns to Step S1030 of FIG. 18. When the controls by the player 100 included a rapid fire period in Step S1072 (Yes in S1072), the aim position generating unit 164 extracts aim information in the rapid fire period from the shooting information obtained in Step S1071. Furthermore, the aim position generating unit 164 determines if the aim positions of successive shooting in the rapid fire period are distant from each other by a predetermined amount or more (if aim blurring occurred), for example, if the aim positions are distant by ¼ or more of the width of the screen (S1073). FIG. 20 shows an example of shooting scenes. The four pictures schematically show that video changes as time progresses from top to bottom. The four pictures show a period during which the successive shooting controls identified in Step S1072 are being performed. The dashed lines in screen 1 are line segments which divide the width of the screen into four. In the screen 1, the player 100 is aiming at a visual target 2. In screen 2, the player 100 is aiming at a visual target 1. Since the aim position in the screen 1 is distant from the aim position in the screen 2 by ¼ or more of the width of the screen, the screen 1 and the screen 2 are not considered to be rapid file. The control input is provided, for example, once per 50 ms. When the value is, for example, ¼ of the width of the screen, it is considered that the aim position has changed.

The aim position moves from the screen 2 to the screen 3, from the screen 3 to the screen 4 along with the movement of the visual target 1. Since the movement of the aim position is less than ¼ of the width of the screen, the shooting controls from the screen 2 to the screen 4 are considered to be rapid fire. When the aim positions of the successive shooting in the rapid fire period are not distant from one another by a predetermined amount or more, it is considered that no aim blurring is occurring and the player 100 is gazing at one visual target (Yes in S1073), and the process proceeds to Step S1074. On the other hand, when it is determined in Step S1073 that the successive aim positions are distant from one another by a predetermined amount or more and that the gaze position frequently moves among visual targets (No in S1073), the process returns to Step S1030 of FIG. 18.

In Step S1074, the time period information obtaining unit 162 identifies a time period corresponding to the rapid fire period identified by the shooting information obtaining unit 161 in S1072 (S1074). Here, a time period, from the time of the first shooting control to the time of the last shooting control in the period which is identified in Step S1072 and during which each shooting control is performed at an interval of less than 500 ms, is determined to be a rapid fire time period. The region information obtaining unit 163 extracts, from the target region information 130a stored in the target region information storing unit 130, the visual target in the video presented to the player 100 in the rapid fire time period identified in S1074 and the region of the visual target on the display screen (S1075). As shown in FIG. 7, the target region information storing unit 130 includes, as the target region information 130a, IDs for identifying visual targets, information on time positions in video, and information on regions of the visual targets on the screen. In cases where a plurality of visual targets were displayed during the rapid fire time period as shown in the screen 2 of FIG. 20, the visual targets and their regions on the screen are extracted.

The target identifying unit 165 then determines if it is possible to identify a visual target having a region which overlaps the aim position on the screen in the time period identified as the rapid fire period, among the regions of the visual targets extracted in S1075 (S1076). Here, when the aim position overlaps the region of one visual target, the target identifying unit 165 identifies the visual target as the visual target at which the player 100 was gazing during the shooting controls. On the other hand, when the aim position does not overlap any regions of the visual targets, or when the aim position overlaps the regions of a plurality of visual targets, it is not possible to identify one visual target. When it is not possible to identify one visual target in Step S1076 (No in S1076), the process returns to Step S1030 of FIG. 18. On the other hand, when it is possible to identify one visual target in Step S1076 (Yes in S1076), the testable period determining unit 166 determines, as a testable period, a time period that is within the rapid fire period and during which the aim position overlaps the region on the screen of the visual target identified in Step S1076, and generates data 170a to be accumulated in the testable period accumulating unit 170 (S1077). FIG. 5 shows an example of the data 170a which indicates a testable period accumulated in the testable period accumulating unit 170. The data 170a includes, for example, a target ID for identifying a visual target, a time period during which the player 100 was aiming at the visual target, that is, during which the player 100 was gazing at the visual target, and trajectories of the aim positions in the period during which the player 100 was aiming at the visual target.

Now, referring to FIG. 21, a detailed description is given of Step S1090 (process for searching for comparable periods) of FIG. 18.

Figure 22:
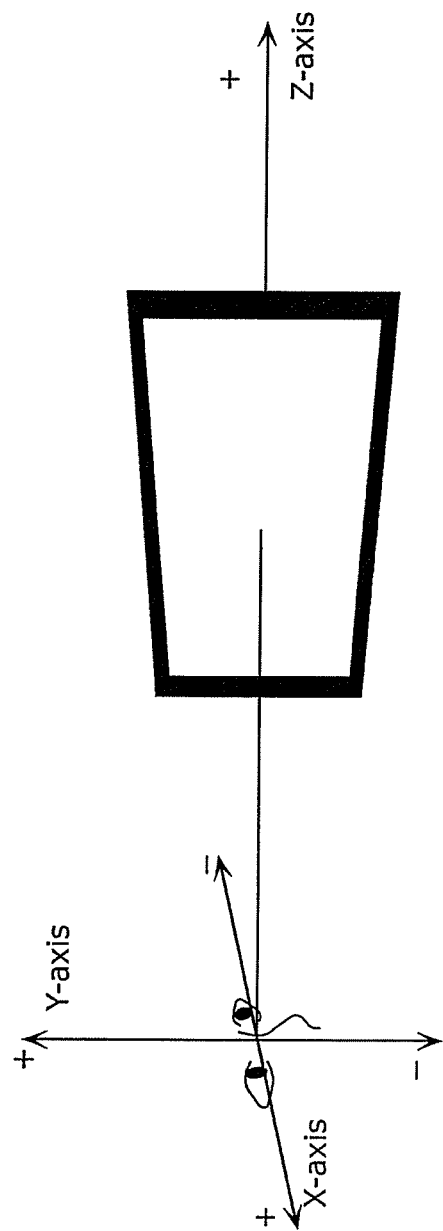
FIG. 22 is a diagram for explaining a virtual position.

The ID and time period obtaining unit 191 extracts a most recent testable period by referring to the testable period accumulating unit 170 (S1091). The 3D trajectory obtaining unit 192 then extracts, based on information of the ID of the visual target and the time period in the most recent testable period obtained in Step S1091, coordinates of 3D virtual position of the visual target in the most recent testable period (S1092). FIG. 6 shows an example of target depth information 180a stored in the target depth information storing unit 180. The target depth information 180a includes, for example, target object IDs displayed on the screen at given time points, and the 3D virtual positions of the visual targets. Here, the time refers to, for example, the elapsed time from the start of the game. As shown in FIG. 22, the virtual position is represented, for example, by representing the center of gravity of a target in the horizontal direction along an x-axis, the vertical direction along a y-axis, and the depth direction along a z-axis, with the center of the face of the player 100, as the origin, viewing the screen from a standard position that is 900 mm away from the front of the center of the screen. In the example of the target depth information 180a shown in FIG. 6, a unit of distance is mm. In the case of a stationary game machine, by fixing the positions of the display and the seat, it is possible to fix the position of the center of the face of the player 100 and the position of the display. In the case of a portable game machine which includes a display and a control input unit, a game machine which is connected to a home television, and a personal computer, by displaying, at the start of the game, an instruction for the distance between the position of the player 100 and the display, it is possible to guide the face of the player 100 to the position which allows eye movements of the player 100 to be measured. In cases where a plurality of players 100 play a game while viewing a single display, it may be that an infrared or a wireless position sensor is provided to the control input unit 140 to obtain the relative position between the display and each player 100, and a correction is made to the measurement result of the eye movements.

The x-axis has positive values in the direction to the right of the player 100, and negative values in the direction to the left of the player 100. The y-axis has positive values in the vertical direction from the player 100. The z-axis has positive values in the direction moving away from the player 100. The same trajectory searching unit 193 searches for a testable period during which the player 100 was gazing at the visual target having the same trajectory as the trajectory of the virtual positions of the visual target at which the player 100 was gazing in the most recent testable period extracted in Step S1092 (S1093). More specifically, in Step S1093, the same trajectory searching unit 193 extracts, from the target depth information storing unit 180, the trajectory of the virtual positions of the visual target (target depth information 180$a$) which correspond to the target ID and the time period in each testable period indicated by the data 170$a$ accumulated in the testable period accumulating unit 170, and searches testable periods that is within 20 minutes from the start of the game, for a visual target having the same trajectory as the trajectory of the virtual positions of the visual target at which the player 100 was gazing in the most recent testable period. In this way, it is possible to compare the state where the player 100 is not fatigued immediately after the start of the game and the most recent state. The same trajectory searching unit 193 determines if the result of the search in Step S1093 includes, within 20 minutes from the start of the game, any testable periods having the same trajectory as the most recent testable period (S1094).

When no testable period exists which has the same trajectory within 20 minutes from the start of the game in Step S1094 (No in S1094), the process returns to Step S1030 of FIG. 18. On the other hand, when a testable period exists which has the same trajectory within 20 minutes form the start of the game in Step S1094 (Yes in S1094), the comparison period determining unit 194 determines, as two periods for which the eye movements are compared, the most recent testable period and the searched testable period having the same trajectory within 20 minutes from the start of the game. The comparison period determining unit 194 then cuts out the time periods where the trajectories of the visual targets are the same from the two testable periods, and determines the cut out periods as the time periods used for tests (S1095). When a plurality of testable periods are extracted which have the same trajectory within 20 minutes from the start of the game, the comparison period determining unit 194 determines, as a comparison period, the testable period having the longest time period during which the trajectory of the visual target is the same as the trajectory of the visual target in the most recent testable period.

Here, in Step S1093, the same trajectory searching unit 193 searches for visual targets having the same trajectory as the trajectory of the virtual positions of the visual target at which the player 100 was gazing in the most recent testable period; however, it may be that the same trajectory searching unit 193 sets similarity degree of the trajectories and search for the periods having a predetermined similarity degree or higher. The similarity degree is obtained, for example, in such a way that, with respect to the trajectories from the start points to the end points of the two visual targets, the sum of the differences between the virtual positions, that is, the sum of the distance between the virtual positions are obtained, the value of the sum is divided by time length of the trajectory, and an inverse of the value thus obtained is determined to be the similarity degree. When the trajectories match, the similarity degree is set to an infinitive value. The similarity degree that is considered as similar is, for example, 1/50 (sec/mm) or greater. The value is adjusted depending on the size of the screen or the distance from the screen at the time of viewing. Alternatively, the similarity degree may be obtained in such a way that, with respect to the trajectories from the start points to the end points of the two visual targets, the sum of the differences between the virtual positions, that is, the sum of the distance between the virtual positions are obtained, and the sum is divided by the movement distance of one of the trajectories, for example, the trajectory that is within 20 minutes from the start of the game, and an inverse of the value thus obtained, that is, the ratio of the sum of the differences between the virtual positions to the movement distance, may be determined to be the similarity degree. For example, when the movement distance is ten times as great as or greater than the sum of the differences, it is considered to be similar. The value is adjusted depending on the size of the screen or the distance between the player 100 and the screen at the time of viewing.

Furthermore, here, in Step S1093, the same trajectory searching unit 193 searches for the visual targets having the same trajectory as the trajectory of the virtual positions of the visual target at which the player 100 was gazing in the most recent testable period; however, it may be that the same trajectory searching unit 193 extracts only depth movements of the visual targets, and searches for the visual targets having the same movement vector in depth.

Furthermore, here, in Step S1093, the same trajectory searching unit 193 searches for the visual targets having the same trajectory as the trajectory of the virtual positions of the visual target at which the player 100 was gazing in the most recent testable period; however, it may be that the same trajectory searching unit 193 searches for the time periods having the same or similar trajectory of the aim positions controlled by the player 100 in the testable period. The aim positions are accumulated as the horizontal positions on the screen. The similarity degree is, for example, obtained in such a way that, with respect to the trajectories from the start points to the end points of the two aim positions, the sum of the differences between the aim position coordinates of the left and right screens, that is, the sum of the distance between the aim positions are obtained, the value of the sum is divided by time length of the trajectory, and then an inverse of the value thus obtained is determined to be the similarity degree. When the trajectories match, the similarity degree is set to an infinitive value. The distance between the aim positions is represented in a unit of pixel. The similarity degree that is considered as similar is, for example, 1/30 (sec/pixel) or greater. The value is adjusted depending on the size or resolution of the screen.

Furthermore, when a plurality of testable periods having the same trajectory are extracted in Step S1094, the comparison period determining unit 194 determines, as a comparison period, the testable period having the longest period during which the trajectory of the visual target is the same as the trajectory of the visual target in the most recent testable period; however, it may be that the comparison period determining unit 194 may select the time period having the greatest depth movement or highest speed depth movement.

Furthermore, when a plurality of testable periods having the same trajectory are extracted in Step S1094, the comparison period determining unit 194 determines, as a comparison period, the testable period having the longest period during which the trajectory of the visual target is the same as the trajectory of the visual target in the most recent testable period; however, the comparison period determining unit 194 may select the period during which the color contrast ratio of the visual target to background is equivalent to that in the most recent testable period. The contrast ratio is calculated according to "Technique 2.2.1 [priority 3] Test the color attributes of the following elements for visibility" in Non-Patent Literature "Techniques for Accessibility Evaluation And Repair Tools" W3C Working Draft, 26 Apr. 2000. The range which is considered as equivalent is, for example, a case where the difference between the contrast ratios is ±5% or less.

In this way, comparison can be made under the same or similar conditions which influence stereoscopic viewing.

Furthermore, when a plurality of testable periods having the same trajectory are extracted in Step S1094, the comparison period determining unit 194 determines, as a comparison period, the testable period having the longest period during which the trajectory of the visual target is the same as the trajectory of the visual target in the most recent testable period; however, the comparison period determining unit 194 may select the period during which an amount of the line segment indicating the horizontal plane in the background image is equivalent to that in the most recent testable period. In the case of computer graphics, one-point perspective, two-point perspective, or 3-point perspective is often used for basic structure of background images. For comparing the amount of line segments indicating the horizontal planes, among the trajectory lines included in a background image in the perspectives used, the sum of the length of the line segments drawn along the trajectory lines other than the trajectory lines vertically drawn in the 3-point perspective is compared. The line segments are, for example, outlines of furniture or doors in the case of indoor, and are outlines of roofs, windows and doors of buildings in the case of outdoor. Examples of the range that is considered as equivalent include a case where the difference between the sums of the line segments is ±5% or less of the sum of the line segments in the background image of video in one of the testable periods, for example, the testable period within 20 minutes from the start of the game.

In this way, comparison can be made under the same or similar conditions which influence stereoscopic viewing.

Now, referring to FIG. 23, a detailed description is given of Step S1110 (process for comparing eye movements) of FIG. 18.

In Step S1100, in the eye movement extracting unit 220, the time period obtaining unit 221 obtains two time periods determined in Step S1095, and the data extracting unit 222 extracts eye movement data according to the time periods obtained by the time period obtaining unit 221, from the eye movement data 210a accumulated in the eye movement accumulating unit 210 from immediately after the start of the game.

The eye movement data 210a includes, as shown in FIG. 9, coordinates of the pupil center of the right eye and coordinates of the pupil center of the left eye, as well as time at which each coordinate was determined. Here, time is indicated by the elapsed time from the start of the game. For example, coordinates of the centers of the pupils of both eyes were measured every 50 milliseconds and accumulated. In Step S1100, with respect to two time periods, the data extracting unit 222 extracts coordinates of the pupil centers of both eyes at respective sample points from the start point to the end point which are indicated by the elapsed time from the start of the game in each time period.

As shown in FIG. 16, the data dividing unit 231 divides the eye data in the two time periods extracted by the eye movement extracting unit 220 in Step S1100, into right-eye data and left-eye data, and accumulates two items of the right-eye data in the right-eye data accumulating unit 232 and two items of the left-eye data in the left-eye data accumulating unit 233 (S1111). The right-eye data comparing unit 234 calculates the difference between the eye movement data of the right eye accumulated in the right-eye data accumulating unit 232 in Step S1111, more specifically, the difference between the eye movement data of the right eye in the most recent testable period and the eye movement data of the right eye in the testable period which is within 20 minutes from the start of the game and which corresponds to the state of the most recent visual target (S1112). The following describes an example of a method for calculating the difference. The eye movements are captured by the camera 201. The image processing unit 203 determines the positions of the centers of the pupils in each image at each sample point and records the determined positions. The two time periods extracted as comparison periods have the same trajectory of the virtual positions of the visual targets. Hence, the right-eye data comparing unit 234 determines the difference, that is, the absolute value of the difference between the most recent eye movement data and the eye movement data obtained within 20 minutes from the start of the game.

Here, the coordinates at each time sample point of the most recent right-eye movement data is represented by Math 1.

$$(Rxp_i, Ryp_i) \qquad \text{[Math 1]}$$

The coordinates at each time sample point of the eye movement data within 20 minutes from the start of the game is represented by Math 2.

$$(Rxs_i, Rys_i) \qquad \text{[Math 2]}$$

Here, with the start point of each time period being 0, i represents a value which indicates each sample point at a relative sample period from the start point of the time period. The maximum value of i is the number of sample points included in a time period. The two time periods have the same trajectory of the virtual positions of the visual targets. In other words, the two time periods have the same time length; and thus, the two time periods include the same number of sample points. When i is the same, it means that the virtual positions of the visual targets are the same.

The difference between the most recent eye movement data and the eye movement data obtained within 20 minutes from the start of the game can be represented by Math 3.

$$\Sigma(|Rxp_i - Rxs_i| + |Ryp_i - Rys_i|) \qquad \text{[Math 3]}$$

This is the sum of the displacement of the pupil centers within the time periods when the player 100 is gazing at a visual target at the same virtual position.

The left-eye data comparing unit 235 calculates the difference between the eye movement data of the left eye accumulated in the left-eye data accumulating unit 233 in Step S1111, more specifically, the difference between the eye movement data of the left eye in the most recent testable period and the eye movement data of the left eye in the testable period which is within 20 minutes from the start of the game and which corresponds to the state of the most recent visual target (S1113). The left-eye data is calculated in the same manner as the right-eye data.

More specifically, with respect to the eye movement data shown in FIG. 16, the left-eye data comparing unit 235 compares coordinates of the pupil centers at each time point from the start points to the end points of the time periods between the eye movement data in the most recent testable period and the eye movement data in the testable period which corresponds to the state of the most recent visual target. The left-eye data comparing unit 235 then calculates the difference of the coordinate positions of the pupil centers at an equivalent time point from the start of the time periods between the most recent testable period and the testable period corresponding to the state of the most recent visual target. The sum of the differences within the time periods is determined as the difference between the eye movement data.

The following describes an example of a method for determining the level of fatigue in Step S1120 of FIG. 18. The fatigue level determining unit 240 obtains the difference of the eye movements of the right eye and the difference of the eye movements of the left eye calculated in Step S1112. It is assumed that the player 100 is not fatigued for 20 minutes from the start of the game, and that the difference of the eye movements from the eye movements obtained within 20 minutes from the start of the game is caused due to visual fatigue.

The difference of the eye movement data of the right eye obtained in Step S1112 is divided by time length of the time period (millisecond), thereby determining the amount of displacement of the eye positions standardized with respect to time.

$$\Sigma(|Rxp_i - Rxs_i| + |Ryp_i - Rys_i|)/(\text{time length of time interval}) \quad [\text{Math 4}]$$

When the difference is below a predetermined level, for example, less than 10 pixel/millisecond, it is determined that no difference between eye movements exists. When the difference is 10 pixel/millisecond or greater, it is determined that the difference between eye movements exists. The fatigue level determining unit 240 determines the level of fatigue by three levels by adding the value obtained by dividing the difference between the right-eye movements obtained in Step S1112 by the time length of the time period and the value obtained by dividing the difference between the left-eye movements obtained in Step S1113 by the time length of the time period and by taking into account the movement speed of the visual target.

FIG. 24 shows an example of a table used by the fatigue level determining unit 240 for determining visual fatigue based on differences of left-eye movements, differences of right-eye movements, and movement speed of visual targets. The movement speed of visual targets is previously classified into three levels: fast; medium; and slow. For example, it is determined in such a manner that 1000 mm/1 s or higher is fast, 500 mm/is or higher and 1000 mm/1 s or lower is medium, and lower than 500 mm/1 s is slow. As the movement speed of visual targets in comparison periods increases, fatigue is likely to occur appearing as the difference in eye movements. As the movement speed decreases, fatigue is not likely to occur. For example, in cases where visual targets in comparison periods move at a speed of 1050 mm/1 s, the fatigue level determining unit 240 determines based on the table in FIG. 24 that no fatigue is occurring when both eyes has no eye movement difference. On the other hand, when either right or left eye has an eye movement difference, the fatigue level determining unit 240 determines that there are fatigue symptoms. When both eyes have eye movement differences, the fatigue level determining unit 240 determines that fatigue is occurring.

As described above, a game machine which includes the visual fatigue level measuring device 1 according to Embodiment 1 can identify a visual target at which the player 100 is gazing by controls input by the player 100 with respect to the visual target, and can compare, by using only video for games, eye movements performed when the player 100 is gazing at the visual target in a state where the player 100 is not fatigued immediately after the start of the game, with the eye movements performed when the player 100 is gazing at the visual target while continuously playing the game. In the video for games, visual targets having the same trajectory can be presented at intervals during the story of the game without causing a feeling of strangeness, for example, by using the same video. It is not necessary to interrupt the game for measuring visual fatigue, or to perform calibration before starting the game. As a result, it is possible to provide the visual fatigue level measuring device 1 which does not interrupt enjoyment of games. Furthermore, since fatigue is determined based on the comparison between the state of the player 100 immediately after the start of the game and the state of the player 100 after continuously playing the game, it is possible to determine the level of fatigue of the player 100 without being influenced by individual differences of stereoscopic viewing ability or accustomed degree of stereoscopic viewing.

In Embodiment 1, the camera 201 for capturing images of eyes are used for directly capturing images of the eyes; however, as shown in FIG. 25, it may be that a half mirror 211 is placed in front of the eyes, an infrared camera 212 and an infrared source 213 are placed below or above the eyes so that images of the eyes are captured using the infrared rays reflected by the half mirror 211. In this way, in cases where a camera is provided to shutter glasses for stereoscopic viewing, images of the eyes can be captured without placing the camera in front of the eyes. In other words, it is possible to enjoy viewing video comfortably without the camera interfering.

Figure 26:
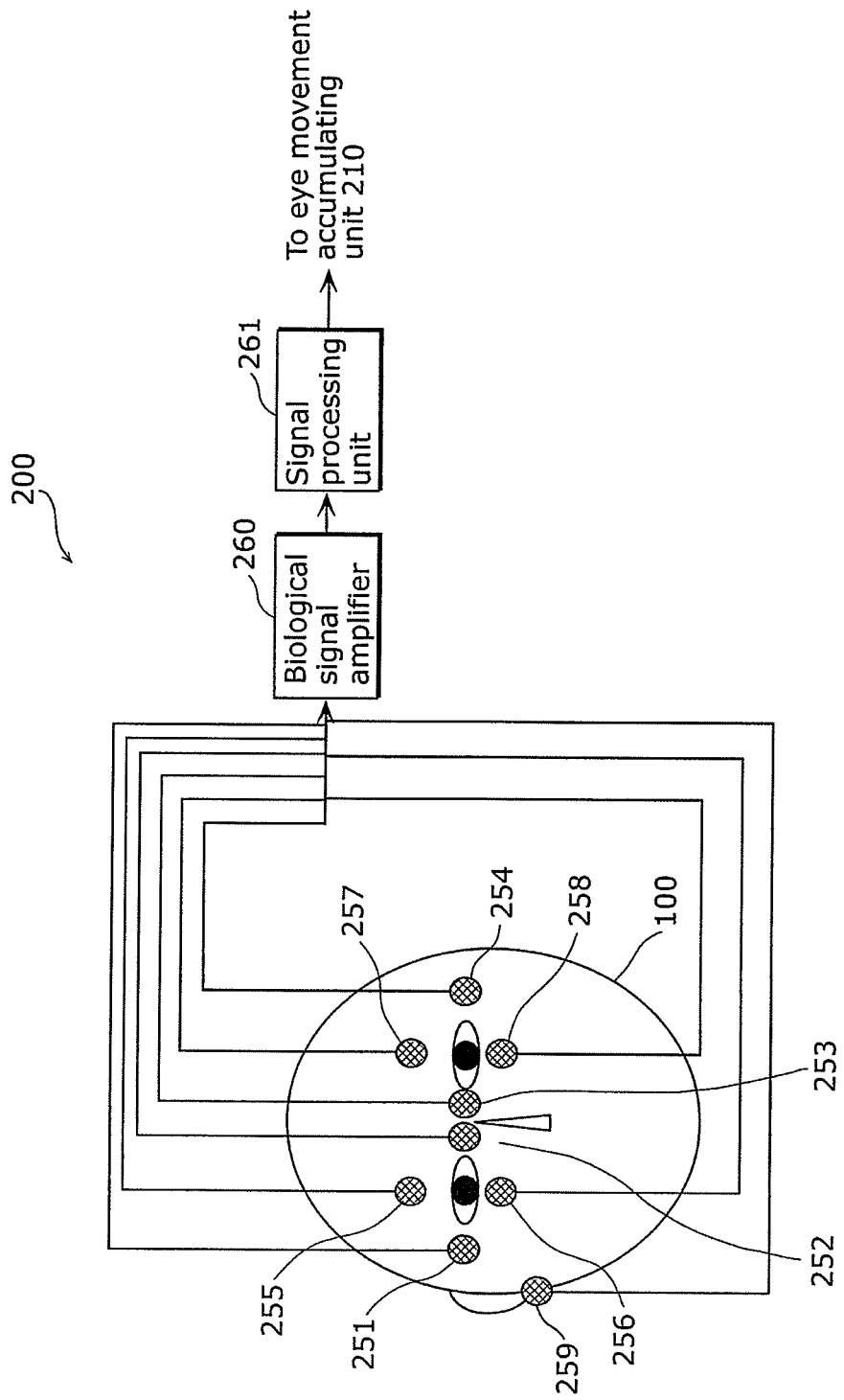
FIG. 26 is a block diagram illustrating another example of a detailed structure of the eye movement obtaining unit shown in FIG. 3.
Figure 27A:
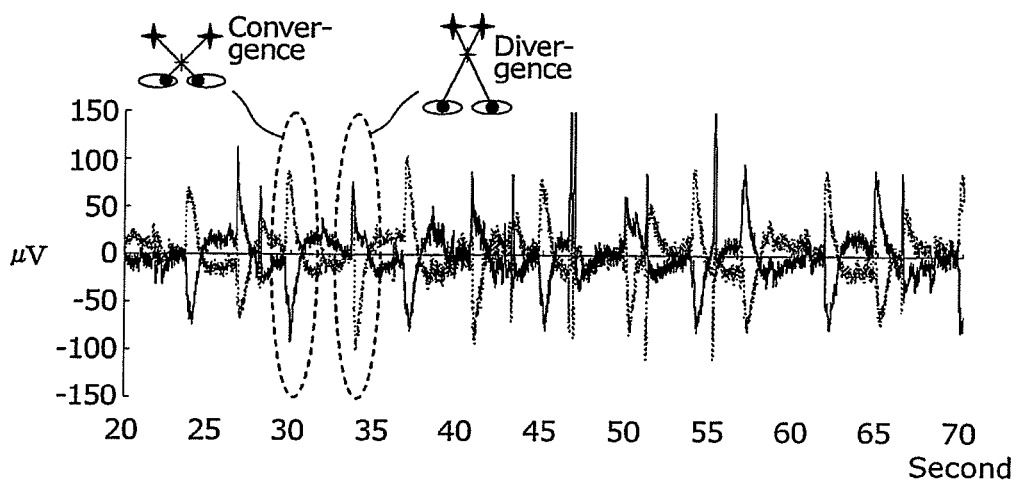
FIG. 27A is a graph showing an example of horizontal eye potentials obtained by the eye movement obtaining unit.
Figure 27B:
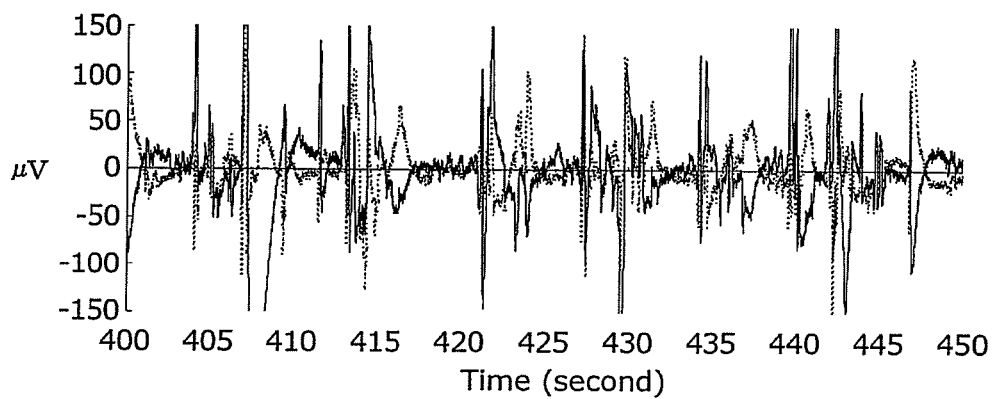
FIG. 27B is a graph showing another example of horizontal eye potentials obtained by the eye movement obtaining unit.
Figure 27C:
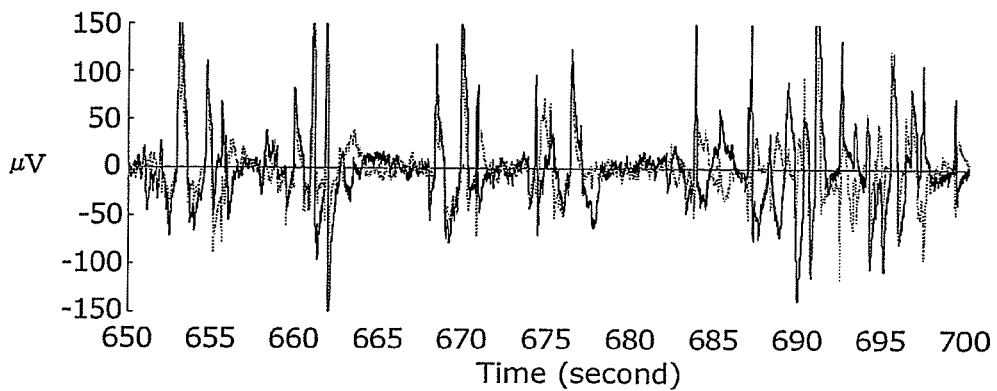
FIG. 27C is a graph showing another example of horizontal eye potentials obtained by the eye movement obtaining unit.

Furthermore, in Embodiment 1, the eye movement obtaining unit 200 obtains eye movements from the images of the eyes; however, it may be that eye movements are obtained by eye potentials (electro-oculography) which allow obtainment of eye movements from surrounding areas of the eyes using electric characteristics of the eyes. For example, as shown in FIG. 26, at least four measuring electrodes 251, 252, 253, and 254 are attached around the eyes of the player 100, and one electrode (an electrode 259) for a reference potential is attached to the skin of an ear lobe, back of the ear or the forehead. The four electrodes 251 to 254 are electrodes for measuring movement of the eyes in the horizontal direction, and are arranged to contact skins of the outer corners of the eyes and the inner corners of the eyes. FIG. 26 further shows an electrode 255 and an electrode 257 that contact areas of the forehead above the eyebrows, and an electrode 256 and an electrode 258 that contact areas below the eyes. The electrodes 255 to 258 are for measuring the movement of the eyes in the vertical direction. A biological signal amplifier 260 obtains electric potentials obtained by the respective electrode 251 to 258, for amplification. A signal processing unit 261 performs filtering or the like to reduce or remove noise generated in the signal amplified by the biological signal amplifier 260, and subtracts the potential of the electrode 259 that is a reference electrode from each of the potentials of the electrodes 251 to 258 that are measuring electrodes to standardize the potentials of the measuring electrodes. Furthermore, the potential indicating the horizontal movement of the right eye is extracted from the difference between the potentials of the electrode 251 and the electrode 252, and the potential indicating the horizontal movement of the left eye is extracted from the difference between the potentials of the electrode 253 and the electrode 254. The potential of the vertical movement of the right eye is extracted from the difference between the potentials of the electrode 255 and the electrode 256, and the potential indicating the vertical movement of the left eye is extracted from the difference between the potentials of the electrode 257 and the electrode 258. Data indicating these potentials are accumulated in the eye movement accumulating unit 210 as the eye movement data 210a. In this case, in Step S1110, the eye movement comparing unit 230 compares horizontal eye potentials of each eye, and also compares vertical eye potentials of each eye, instead of comparing positional information of the eyes. FIG. 27A to FIG. 27C show examples of horizontal eye potentials. FIG. 27A to FIG. 27C show a record of eye potentials of a subject who alternately gazed at a visual target whose virtual distance was 90 cm from the subject and a visual target whose virtual distance was 30 cm from the subject, under the viewing conditions same as those in FIG. 2A to FIG. 2C. The 3D video used here has heavier load with respect to visual system compared to ordinary video content. Thus, fatigue appears in the eye potentials sooner than ordinary video content. FIG. 27A shows the eye potentials in the state where the subject has no fatigue from 20 to 70 seconds immediately after the start of the viewing. FIG. 27B shows the eye potentials for 50 seconds in the state where the subject started to feel fatigue after the elapse of 400 seconds from the start of the viewing. FIG. 27C shows the eye potentials for 50 seconds in the state where stereoscopic viewing is difficult due to fatigue after the elapse of 650 seconds from the start of the viewing.

In each graph, the horizontal axis indicates elapsed time from the start of the viewing experiment in seconds, and the vertical axis indicates, in microvolts, eye potentials obtained as the differences in the potentials from the electrodes placed at the inner and outer corners of the left and right eyes. In FIG. 27A to FIG. 27C, solid lines indicate eye potentials of the left eye of the subject. The positive potentials indicate that the eye moved toward the left side of the subject, that is, toward the outer corner of the eye. The negative potentials indicate that the eye moved toward the inner corner of the eye. Dashed lines indicate eye potentials of the right eye of the subject. The positive potentials indicate that the eye moved toward the left side of the subject, that is, toward the inner corner of the right eye. The negative potentials indicate that the eye moved toward the outer corner of the right eye. When a visual target comes closer to the subject decreasing the depth of the virtual position, the eyes of the subject has convergence, and the left and right eyes move toward the inner corners of the eyes. In FIG. 27A to 27C, the graph of the left eye indicates negative potentials, and the graph of the right eye indicates positive potentials. The eye potentials shown in FIG. 27A to FIG. 27C are records of AC signals, and are records of potential changes. The potential changes generated when the eye moves are recorded. When the eye stays at the position after the movement, the potential attenuates approaching 0. Hence, unlike FIG. 2A to FIG. 2C, it is difficult to observe the position at which the eye stays, however, it is possible to record eye movements performed in accordance with depth change of a visual target.

In the state shown in FIG. 27A where the subject has no fatigue immediately after the start of the viewing, the left and right eyes move in the opposite direction in accordance with depth change of the visual target, thereby repeating convergence and divergence.

In the state shown in FIG. 27B where the subject is feeling visual fatigue after the continuous viewing, convergence and divergence are correctly performed in some cases with respect to the visual target which repeatedly changes the distance to the subject between 90 cm and 30 cm. In other cases, the eyes move in phase multiple times without convergence or divergence, showing that the eyes are not being able to follow the depth movement. Furthermore, in the state shown in FIG. 27C where stereoscopic viewing is not possible at the close position due to visual fatigue, the eyes move almost in phase, and proper movement of convergence and divergence are not performed. Even when convergence or divergence where the eyes move in reversed phase is performed, its movement is small. In this way, it is also possible to observe visual fatigue of a viewer who is viewing 3D video by temporally comparing the potentials of the eyes obtained while viewing the 3D video.

Figure 28:
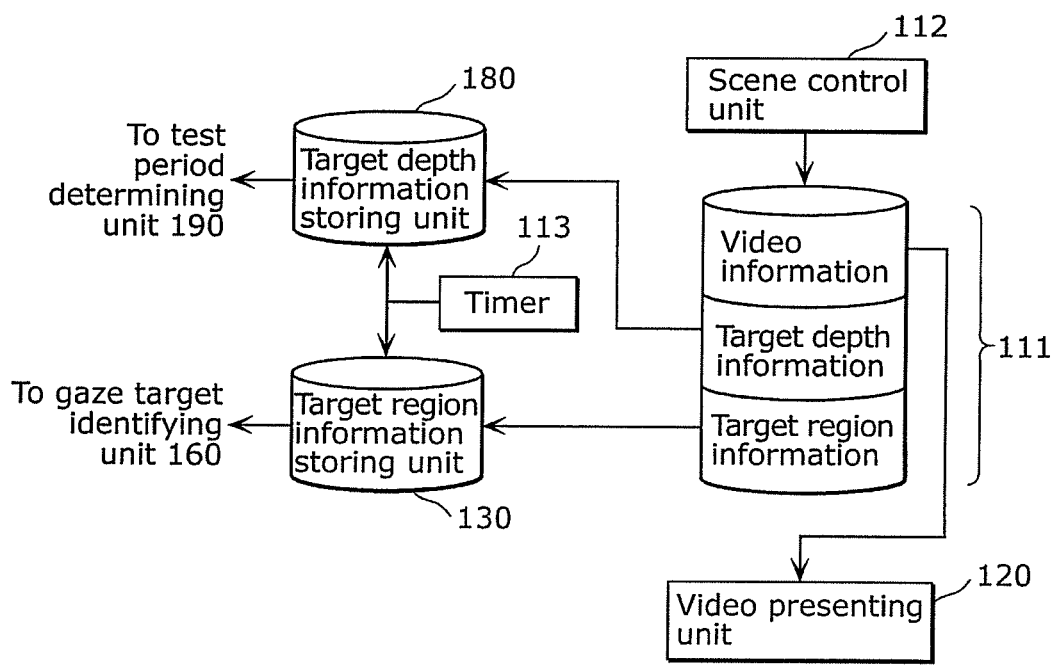
FIG. 28 is a block diagram illustrating an example of another structure of a game machine including the visual fatigue level measuring device according to Embodiment 1.

Furthermore, in Embodiment 1, it has been described that the video information accumulating unit 110, the target region information storing unit 130, and the target depth information storing unit 180 store predetermined information; however, in cases where different scenes are output depending on game progress such as in a role-playing game, it may be that, as shown in FIG. 28, region information and depth information of visual targets corresponding to the video presented to the player 100 along with the game progress are stored. In the structure shown in FIG. 28, in accordance with the game progress, a scene control unit 112 identifies video to be output from a video information accumulating unit 111 which accumulates, for example, video information for each scene and region information (target region information) and depth information of visual targets in the video information. The video information accumulating unit 111 outputs video information to the video presenting unit 120 according to an instruction from the scene control unit 112, and outputs, to the target region information storing unit 130, region information of the corresponding visual targets (target region information 130a). The video information accumulating unit 111 further outputs, to the target depth information storing unit 180, depth information of the visual targets (target depth information 180a) corresponding to the output video. The target region information storing unit 130 stores, as region information of the visual targets (target region information 130a), information output from the video information accumulating unit 111 along with time information determined by the timer 113. In the similar manner, the target depth information storing unit 180 stores, as depth information of visual targets (target depth information 180a), information output from the video information accumulating unit 111 along with the time information determined by the timer 113.

Figure 29:
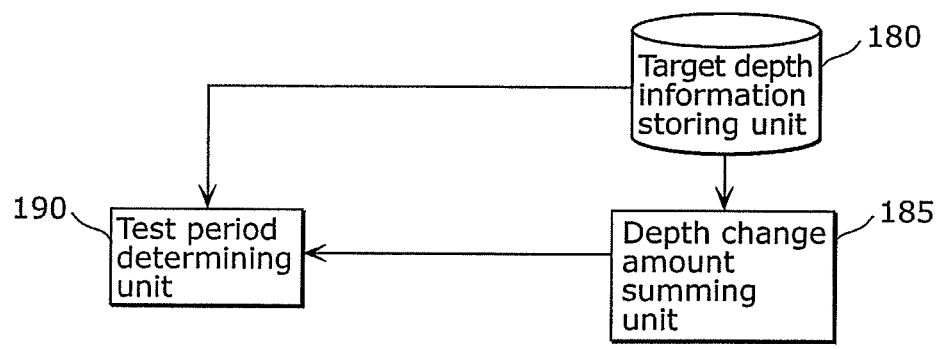
FIG. 29 is a block diagram illustrating an example of another structure of a game machine including the visual fatigue level measuring device according to Embodiment 1.

Furthermore, in Embodiment 1, it has been described that the test period determining unit 190 selects a time period to be compared with the most recent eye state from among the testable periods within 20 minutes from the start of the game; however, it may be that under the assumption that the player 100 is not likely to be fatigued immediately after the start of the game, the test period determining unit 190 determines the most recent testable period after a predetermined period of time, for example, after 30 minutes or more from the start of the game, and compares the most recent eye movements with the eye movements in an earlier time period. Furthermore, since viewing video with large depth movement during games easily causes fatigue, a depth change amount summing unit 185 may be added as shown in FIG. 29. The depth change amount summing unit 185 extracts, from the target depth information storing unit 180, depth information of all visual targets (target depth information 180a) included in the video presented to the player 100, and outputs the sum of the depth information as a depth change index. As time progresses after the start of the game, the sum of the depth information increases. It may also be that the most recent testable period is determined after the sum of the depth change amount exceeds a predetermined level and increases to the amount at which the player 100 may be fatigued, and the eye movements in the most recent testable period is compared with the eye movements in a time period during which the sum of the depth change amount falls within another predetermined level, that is, the value of the total depth change amount that is within the range which causes no fatigue. For example, in the case where the player 100 is playing games at 90 cm away from the screen, when the sum of the depth change amount exceeds 4000 cm, the value is set to a level at which the player 100 may be fatigued, and the time period during which the sum of the depth change amount is less than 2000 cm is determined as a range which does not cause fatigue. It is to be noted that these values should be adjusted depending on, for example, the size of the screen, or the distance between the player 100 and the screen.

(Variation 1 of Embodiment 1)

The following describes Variation 1 of Embodiment 1. Since the basic structure of Variation 1 of Embodiment 1 is the same as that of Embodiment 1, its description is omitted.

Figure 30:
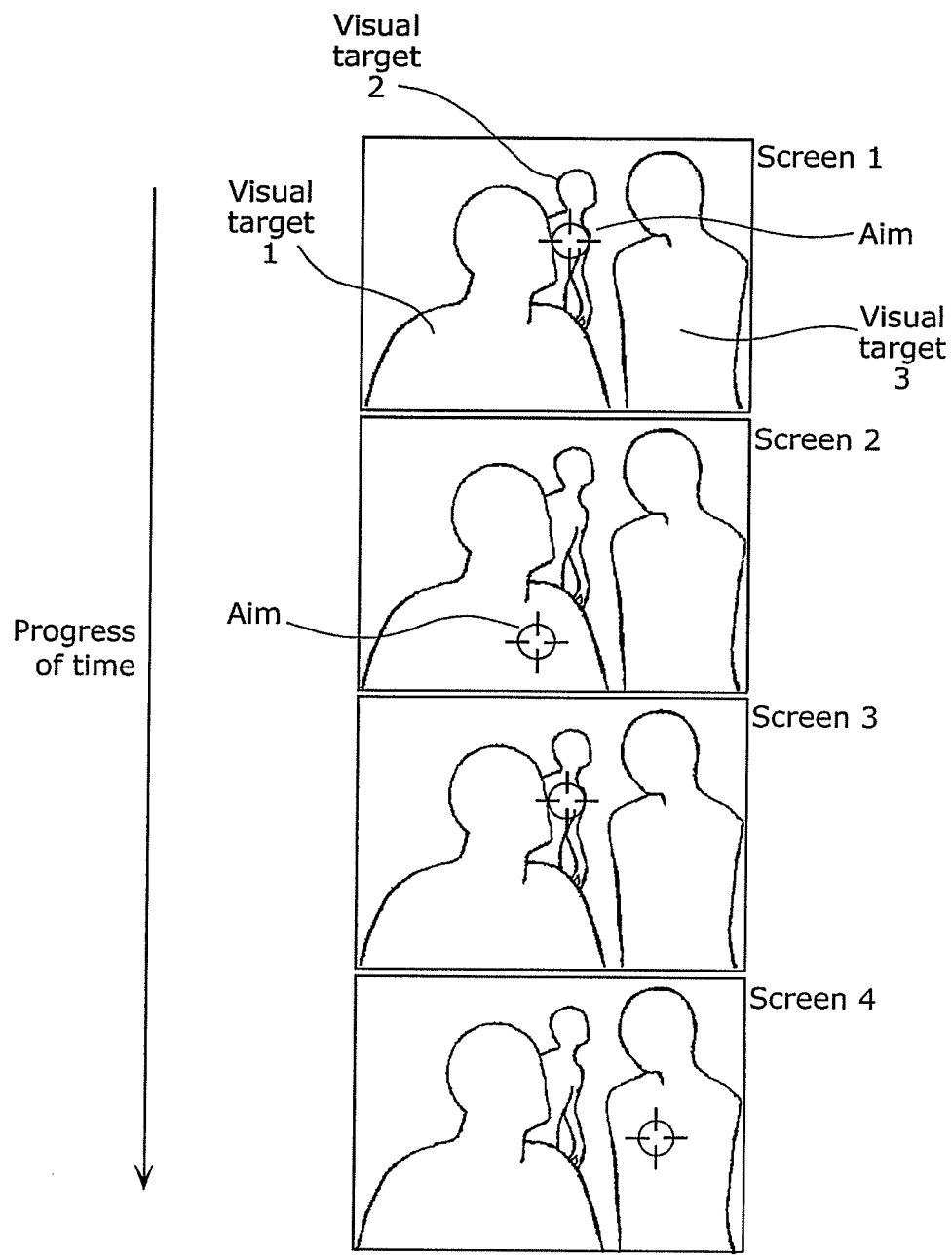
FIG. 30 is a schematic diagram illustrating an example of relationship between output video and control input in a target identifying step according to Variation 1 of Embodiment 1.

A time period extracted as a testable period in Variation 1 of Embodiment 1 is not a period during which the player 100 is gazing at one visual target, but a period during which the player 100 alternately views visual targets arranged at different depth virtual positions. FIG. 30 schematically shows a case where the player 100 views a plurality of visual targets alternately. A visual target 1 is at the very front, and a visual target 2 is at the very back. In Screen 1, the player 100 is performing shooting control aiming at the visual target 2 at the very back. In Screen 2, the player 100 is performing shooting control aiming at the visual target 1 at the very front. In Screen 3, the player 100 is aiming at the visual target 2 at the very back again. In Screen 4, the player 100 is aiming at a visual target 3. In Variation 1, as shown in the example of FIG. 30, time periods in each of which the player 100 alternately views different visual targets arranged at different depth virtual positions, are extracted as testable time periods, and periods having the same depth change of the visual targets at which the player 100 aimed are determined as comparison periods.

Figure 31:
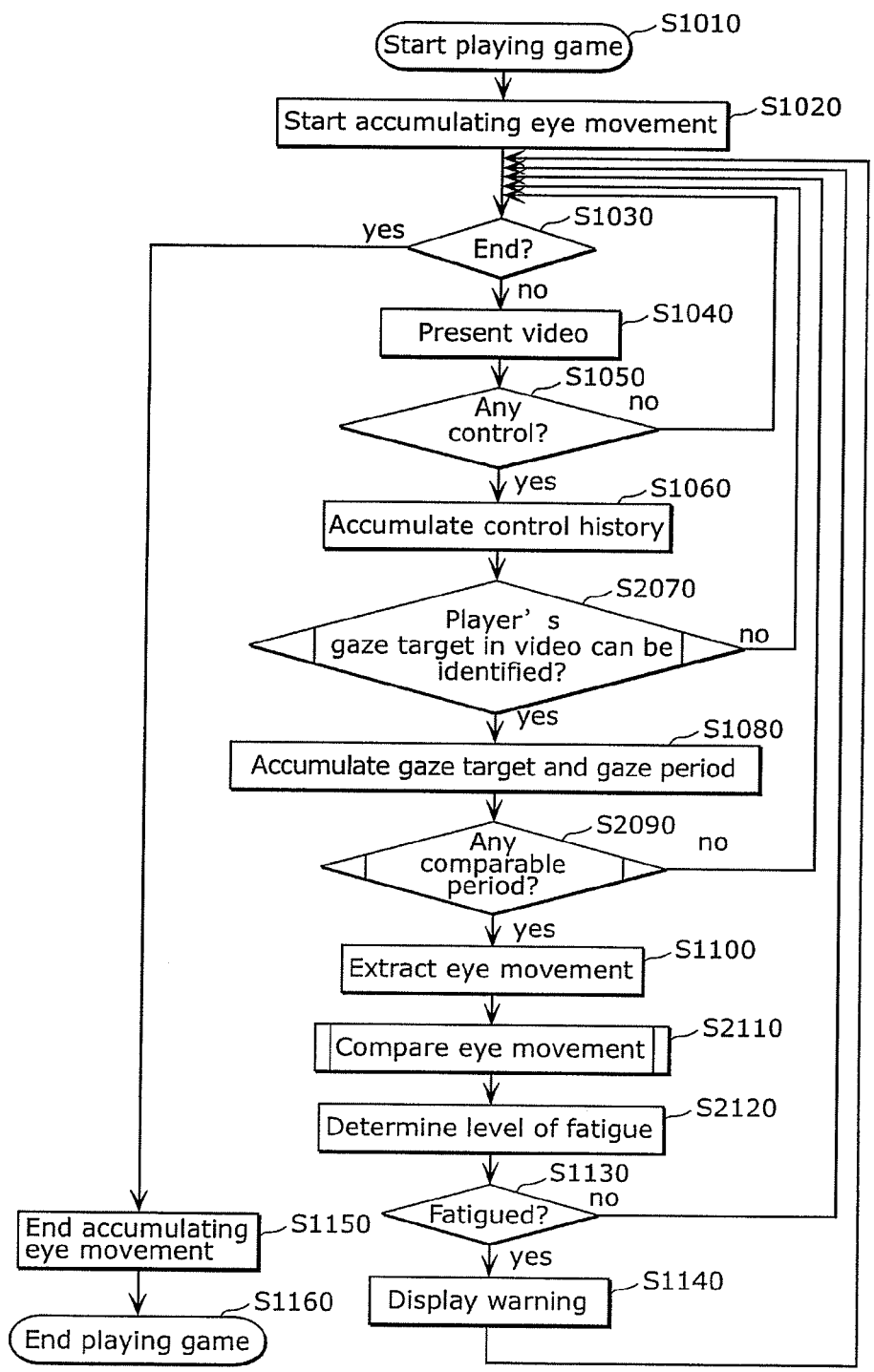
FIG. 31 is a flowchart of an example of the operations of a game machine including a visual fatigue level measuring device according to Variation 1 of Embodiment 1.

FIG. 31 is a flowchart of the processes performed by the visual fatigue level measuring device according to Variation 1 of Embodiment 1.

The processes performed by the visual fatigue level measuring device according to Variation 1 of Embodiment 1 are the same as those of Embodiment 1 other than the following points: Step S1070 is replaced with Step S2070; Step S1090 is replaced with Step S2090; Step S1110 is replaced with Step S2110, and Step S1110 is replaced with Step S2120, and duplicated descriptions are omitted.

Figure 32:
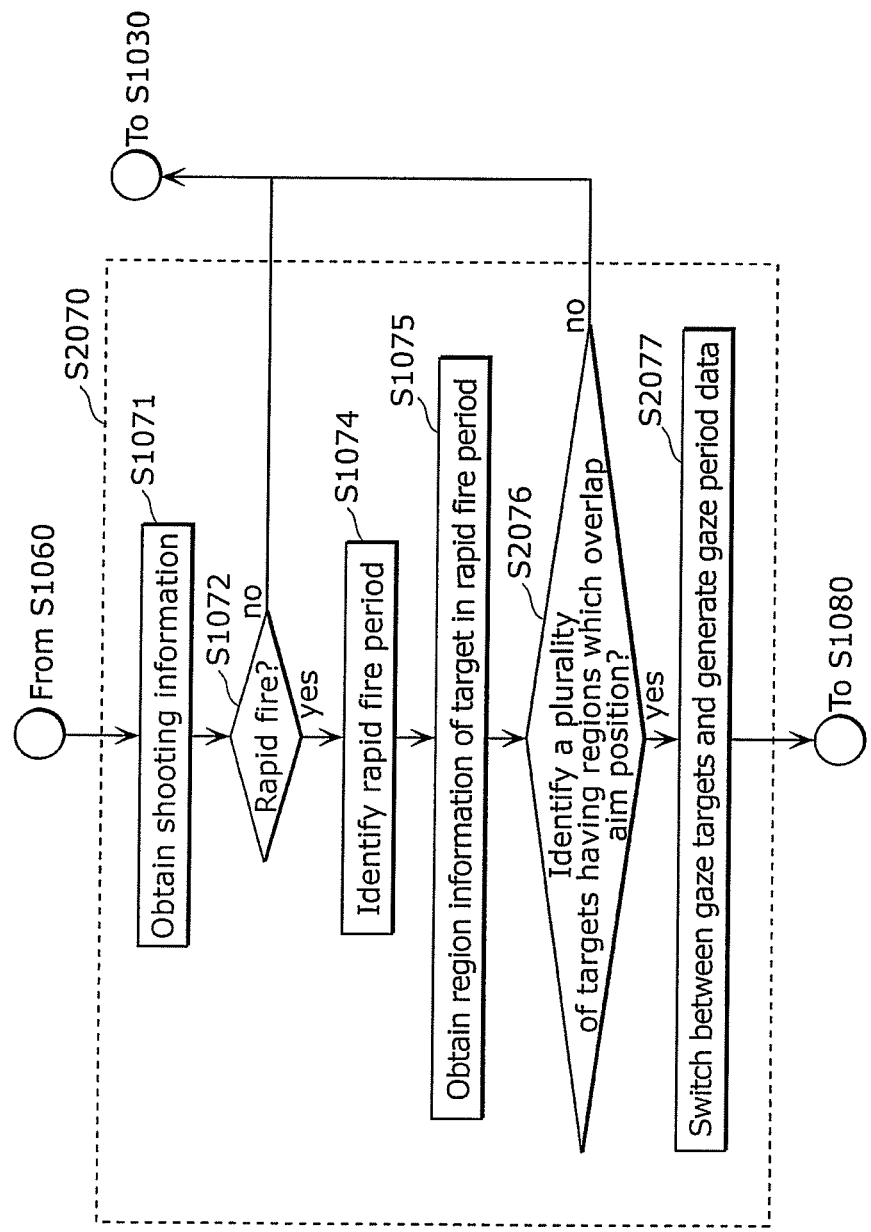
FIG. 32 is a flowchart of an example of the flow of the detailed processes in the target identifying step (Step S2070 in FIG. 31) according to Variation 1 of Embodiment 1.
Figure 34:
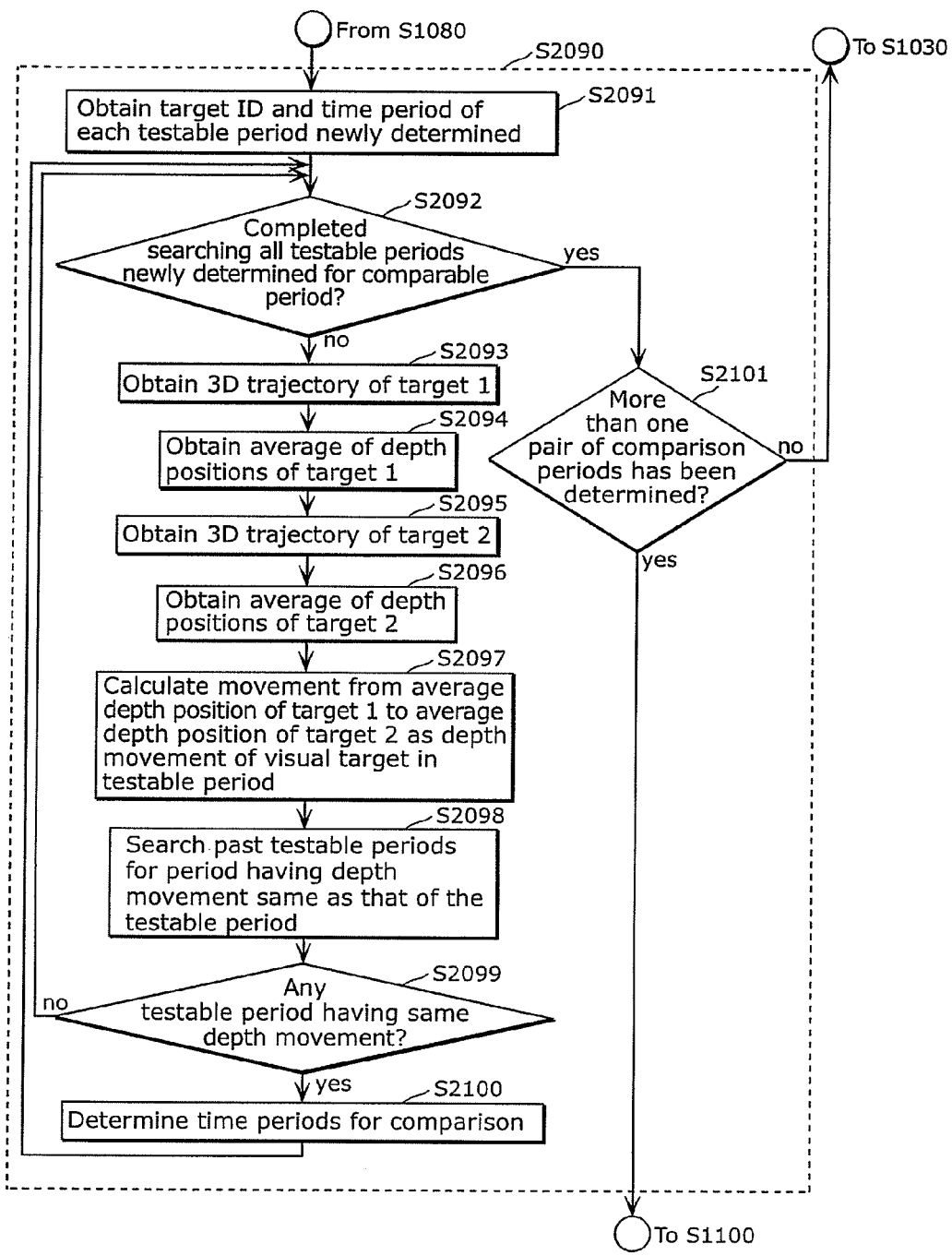
FIG. 34 is a flowchart of an example of the flow of the detailed processes in a comparable period extracting step (Step S2090 in FIG. 31) according to Variation 1 of Embodiment 1.
Figure 35:
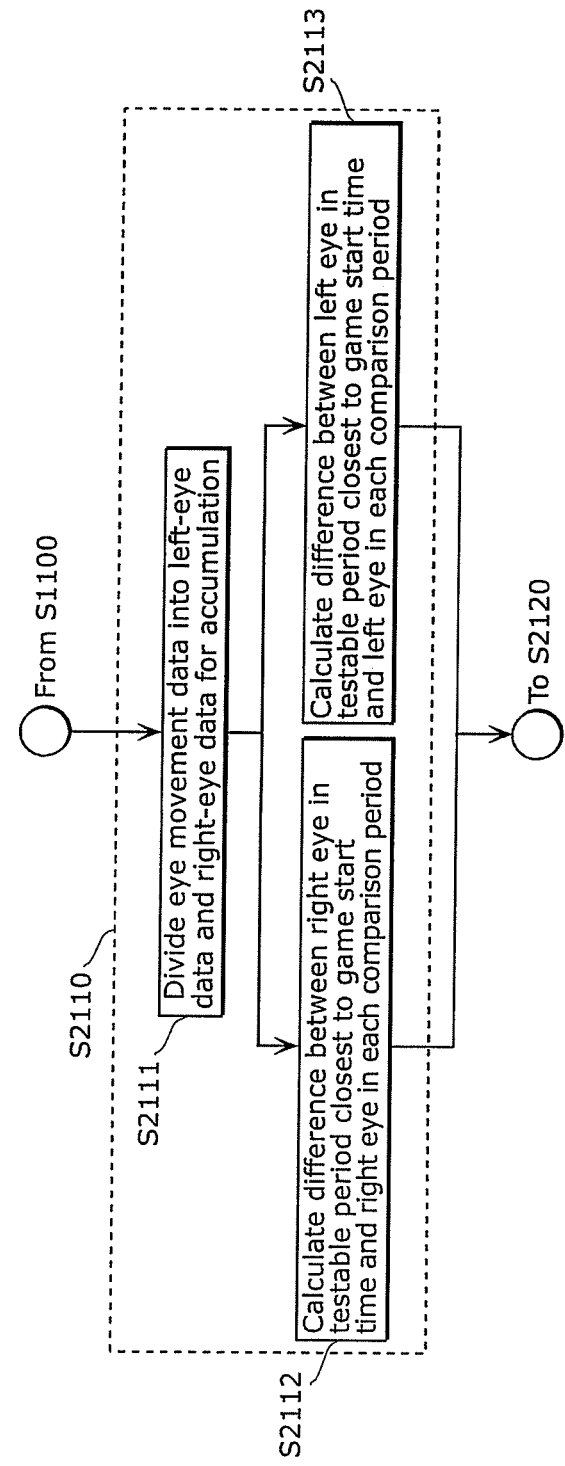
FIG. 35 is a flowchart of an example of the flow of the detailed processes in an eye movement comparing step (Step S2110 in FIG. 31) according to Variation 1 of Embodiment 1.

Each of FIG. 32, FIG. 34, and FIG. 35 is a flowchart of a detailed part of the processes performed by the visual fatigue level measuring device according to Variation 1. FIG. 32 shows a detailed process of Step S2070 for identifying visual targets at which the player 100 is gazing. Referring to FIG. 32, a detailed description is given of Step S2070. Descriptions of processes same as those in FIG. 19 are not given.

The shooting information obtaining unit 161 obtains a series of shooting controls that is most recent made from the control history 150a accumulated in the control history accumulating unit 150 in Step S1060 (S1071). The shooting information obtaining unit 161 determines if the series of shooting controls includes rapid fire, that is, a period during which each shooting control is performed at an interval of less than 500 ms (S1072). When the controls included no rapid fire period in Step S1072 (No in S1072), the process returns to Step S1030 of FIG. 31. On the other hand, when the controls included a rapid fire period in Step S1072 (Yes in S1072), the time period information obtaining unit 162 identifies, as a time period corresponding to the rapid fire period identified by the shooting information obtaining unit 161 at S1072, a time period from the first shooting control to the last shooting control in a rapid fire period. The region information obtaining unit 163 extracts, from the target region information storing unit 130, a visual target in the video presented to the player 100 during the rapid fire time period identified in Step S1074 and the region of the visual target on the display screen (S1075). When there are a plurality of visual targets which were displayed during the rapid fire time period as shown in FIG. 30, the visual targets and their regions on the screen are extracted. The target identifying unit 165 determines if it is possible to identify a plurality of visual targets each having a region which overlaps the aim position on the screen in the time period identified as the rapid fire period, among the regions of the visual targets extracted in S1075 (S2076).

Figure 33:
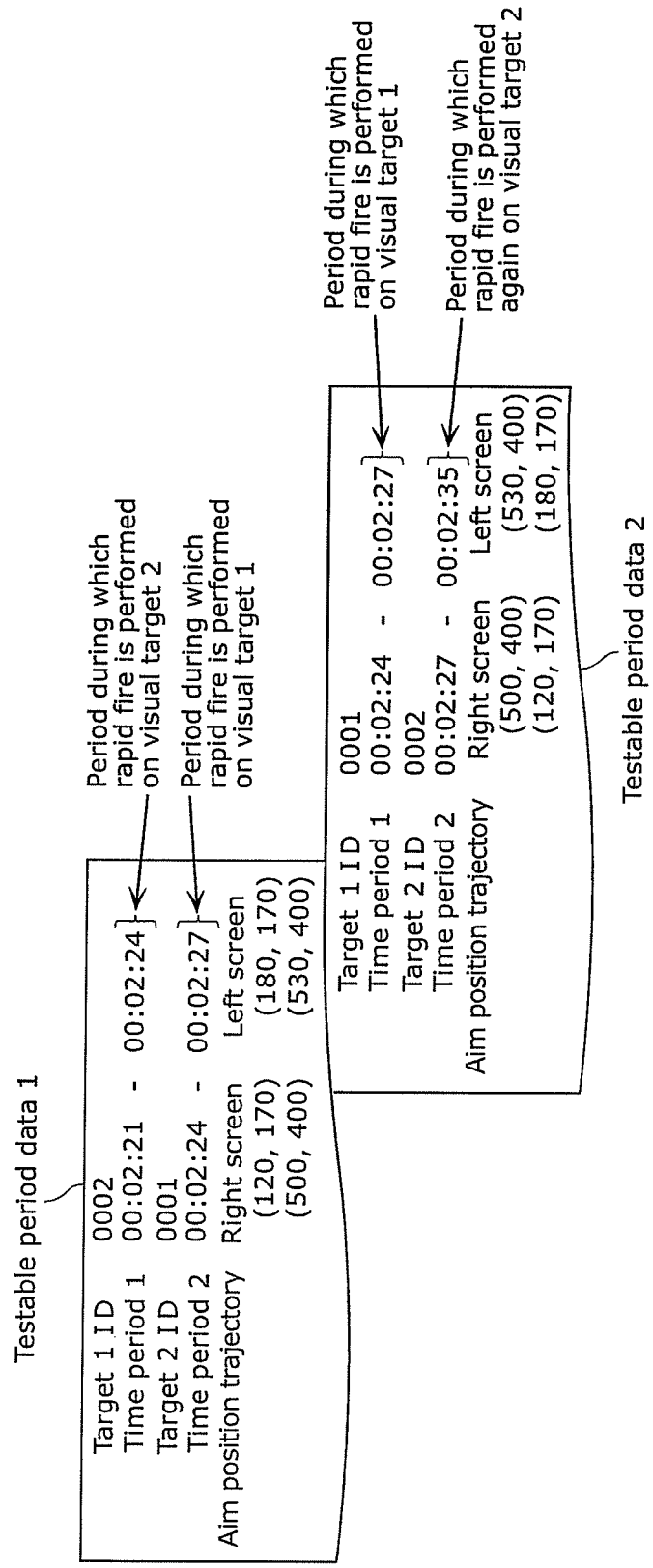
FIG. 33 shows an example of information of testable periods according to Variation 1 of Embodiment 1.

When the aim position does not overlap any regions of the visual targets in the rapid fire period, or when only one visual target which overlaps the aim position is identified (No in S2076), the process returns to Step S1030 in FIG. 31. Furthermore, when the aim position overlaps the regions of a plurality visual targets, it is not possible to identify a visual target, and thus, the process returns to Step S1030 of FIG. 31. On the other hand, in the rapid fire period, when the visual targets identified as the visual targets each having a region which overlaps the aim position change over time, that is, when a plurality of visual targets which overlap the aim position are identified (Yes in S2076), the process continues to Step S2077. The example of FIG. 30 shows a rapid fire period which is from Screen 1 to Screen 4. In Screen 1, the visual target 2 is identified as a visual target which overlaps the aim position, that is, as a gaze point. In Screen 2, the visual target 1 is identified as a gaze point. In Screen 3, the visual target 2 is identified as a gaze point again. In Screen 4, the visual target 3 is identified as a gaze point. In this way, in Step S2076, a state is extracted where the visual target at which the player 1000 gazes changes in the rapid fire time period. The testable period determining unit 166 determines, as a testable period, of the rapid fire period in which a plurality of visual targets were identified in Step S2076, a time period including the period in which the aim position on the screen moves from one visual target to another visual target, and generates data 170a to be accumulated in the testable period accumulating unit 170 (S2077). FIG. 33 shows an example of data 170a accumulated in the testable period accumulating unit 170. The data 170a, for example, includes: two target IDs which indicate the aim position moved from which target to which target; time period 1 during which the aim position overlapped the visual target before the aim position moved; time period 2 during which the aim position overlapped the visual target after the aim position moved; and the trajectories of the aim positions. The testable period data 1 shown in FIG. 33 is an example of testable period data which describes changes from Screen 1 to Screen 2, while the testable period data 2 is an example of testable period data which describes changes from Screen 2 to Screen 3. The target ID shown above indicates the visual target which overlaps the aim position before the movement, and the target ID shown below indicates the visual target which overlaps the aim position after the movement. Both of the testable period data 1 and the testable period data 2 includes the time period of Screen 2. The time period 2 in the testable period data 1 overlaps the time period 1 in the testable period data 2.

FIG. 34 shows a detail of Step S2090 (process for searching for comparable periods) in FIG. 31. Referring to FIG. 34, a detailed description is given of Step S2090.

First, the ID and time period obtaining unit 191 extracts all data 170a which indicates testable periods newly accumulated, from the testable period accumulating unit 170 (S2091). The 3D trajectory obtaining unit 192 determines if searching all of the testable periods obtained in Step S2091 for comparable periods has been completed (S2092). When all search has been completed in Step S2092 (Yes in S2092), the process proceeds to Step S2101. On the other hand, when there are testable periods which have not been searched in S2092 (No at S2092), the process proceeds to Step S2093. In Step S2093, the 3D trajectory obtaining unit 192 obtains, from the target depth information storing unit 180, 3D virtual position coordinates of the visual target 1 (target depth information 180a) that is a visual target before the aim position, that is, the gaze point moves, with respect to one testable period for which searching for comparable periods has not been completed among the newly accumulated testable periods obtained in Step S2091.

The 3D trajectory obtaining unit 192 then extracts, from the 3D virtual position coordinates obtained in Step S2093, the coordinates of the visual target 1 in the depth direction. More specifically, the 3D trajectory obtaining unit 192 calculates the average of the coordinates in the depth direction in the time period during which the aim position overlapped the region of the visual target 1, and determines the obtained average value as the depth position of the visual target 1 before the aim position, that is, the gaze point moved (S2094). The 3D trajectory obtaining unit 192 then obtains the 3D virtual position coordinates of the visual target 2 that is the visual target after the aim position, that is, the gaze point moved, in the same testable period as in S2093. The 3D trajectory obtaining unit 192 extracts the coordinates of the visual target 2 in the depth direction from the 3D virtual position coordinates obtained in Step S2095. More specifically, the 3D trajectory obtaining unit 192 calculates the average of the coordinates in the depth direction in the time period during which the aim position overlapped the region of the visual target 2, and determines the calculated average value as the depth position of the visual target 2 before the aim position, that is, the gaze point moved (S2096). The 3D trajectory obtaining unit 192 further calculates, as depth movement in the testable period, the movement from the average depth position of the visual target 1 to the average depth position of the visual target 2 (S2097).

After that, the same trajectory searching unit 193 searches for testable periods including the same depth movement as the depth movement calculated in Step S2097 (S2098). The same trajectory searching unit 193 may perform processes equivalent to Step S2093 to Step S2097 with respect to past testable periods; however, it may be that in Step S2097, the 3D trajectory obtaining unit 192 stores depth movement information in the testable period in association with the testable period indicated by the data 170a accumulated in the testable period accumulating unit 170, and in Step S2098, the same trajectory searching unit 193 searches the data 170a accumulated in the testable period accumulating unit 170 for depth movement information without referring to the target depth information storing unit 180. The same trajectory searching unit 193 then determines if testable periods exist which have the same depth movement as the depth movement in the testable period (S2099). When no testable period having the same depth movement as the testable period exists in Step S2099 (No in S2099), the process returns to Step S2092. On the other hand, when one or more testable periods exist which have the same depth movement as that in the testable period in Step S2099 (Yes in S2099), the process proceeds to Step S2100.

The comparison period determining unit 194 determines, as comparison periods, a set including the testable period and one or more testable periods having the same depth movement as the testable period searched in Step S2093 (S2100), and the process returns to Step S2092. When all searches has been completed in Step S2092, (Yes in S2092), the process proceeds to Step S2101. In Step S2101, it is determined if it was possible to determine comparison periods in one or more testable periods among all of the testable periods newly determined (S2101). When one or more new testable periods exist for which comparison periods have been determined (Yes at S2101), the process proceeds to Step S1100 in FIG. 31. On the other hand, when no new testable period exists for which comparison periods have been determined (No at S2101), the process returns to Step S1030 in FIG. 31.

FIG. 35 shows a detail of Step S2110 (process for comparing eye movements) of FIG. 31. Referring to FIG. 35, a detailed description is given of Step S2110.

The time period obtaining unit 221 obtains the time period for each of the testable periods determined in Step S2100 in FIG. 34. The time period obtaining unit 221 determines the time period including the time periods 1 and 2 as the time period of each testable period, and extracts eye movement data corresponding to the determined time period of each testable period. The data dividing unit 231 divides the extracted eye movement data into right-eye data and the left-eye data, and accumulates the right and left data into the right-eye data accumulating unit 232 and the left-eye data accumulating unit 233, respectively (S2111). The right-eye data comparing unit 234 calculates the differences between the eye movement data of the right eye in the testable period closest to the start of the game and the right-eye data in each comparison period (S2112). At the same time, the left-eye data comparing unit 235 calculates the differences between the eye movement data of the left eye in the testable period closest to the start of the game and the left-eye data in each comparison period (S2113).

Figure 36:
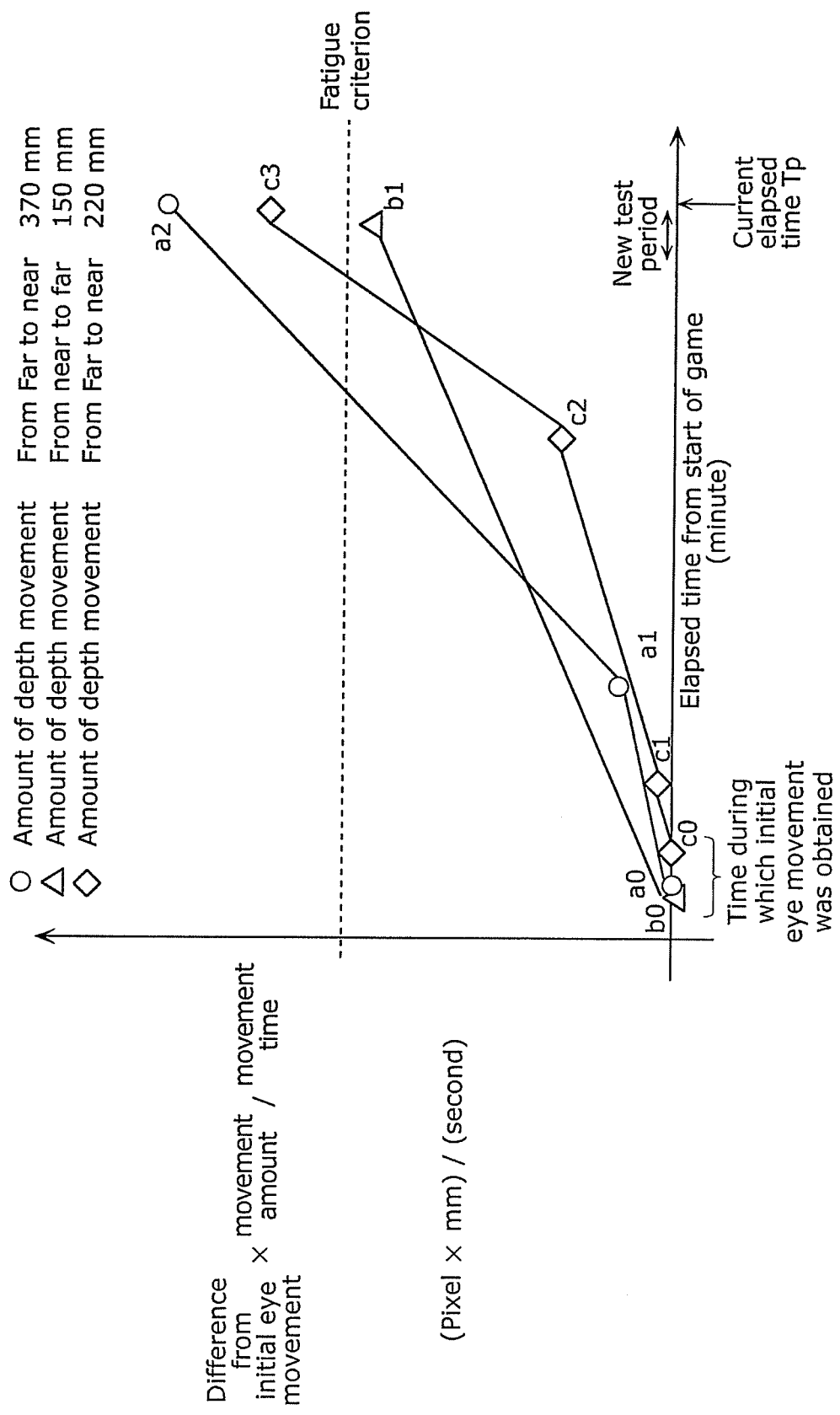
FIG. 36 is a diagram for explaining an example of a method for determining the level of fatigue according to Variation 1 of Embodiment 1.

The following describes an example of a method for determining the level of fatigue in Step S2120. The fatigue level determining unit 240 obtains the differences between the right-eye movements obtained in Step S2112 and the differences between the left-eye movements obtained in Step S2113. In the graph of FIG. 36, the horizontal axis indicates the start time of the time period of the testable period as the time elapsed from the start of the game, and the vertical axis indicates differences between the eye movement data closest to the start of the game and the eye movement data in each comparison period normalized by the depth movement amount. The example of FIG. 36 shows three new testable periods for which comparison period sets are determined: the testable period in which the visual target moves 370 mm in the depth direction toward the player 100 (the graph indicated by circles); the testable period in which the visual target moves 150 mm in the depth direction away from the player 100 (the graph indicated by triangles); and the testable period in which the player 100 moves 220 mm in the depth direction toward the player 100 (the graph indicated by diamonds). It is shown that two comparable periods are included in the period which is indicated by the circles and in which the visual target moves 370 mm toward the player 100, and that one comparable period is included in the period which is indicated by the triangles and in which the visual target moves 150 mm away from the player 100. Furthermore, it is shown that three comparable periods are included in the period which is indicated by the diamonds and in which the visual target moves 220 mm toward the player 100. As fatigue index values in the period which is indicated by circles and in which the visual target moves 370 mm toward the player 100, it is determined that the fatigue index at the time closest to the start of the game is a0, the fatigue index in the next testable period is a1, and the fatigue index in the third testable period is a2. In the period which is indicated by triangles and in which the visual target moves 150 mm away from the player 100, it is determined that the fatigue index at the time closest to the start of the game is b0, and the fatigue index in the next testable period is b1. In the period which is indicated by diamonds and in which the visual target moves 220 mm toward the player 100, it is determined that the fatigue index at the time closest to the start of the game is c0, and the subsequent fatigue indexes are c1, c2, and c3 along the elapsed time. With respect to differences between eye movements, the comparable period that is closest to the start of the game is considered as a standard value in Step 2112 and Step S2113; and thus, the value of the vertical axis at the point closest to the start of the game is 0. Since loads of eye movements increase as the depth movement amount increases, the differences between the eye movements per time obtained in Step S2112 and S2113 are further divided by the depth movement amount and the value thus obtained is determined a fatigue index. In the example of a2 of FIG. 36, the fatigue level determining unit 240 obtains the absolute value of the difference between the position of center of the right eye pupil in the a2 period and the position of center of the right eye pupil in the a0 period at each time point, and the sum thereof is determined as the difference between the right-eye movements in the testable period that is closest to the start time of the game and the right-eye movements in the comparison period. The eye movements of the left eye are obtained in the similar manner to the right eye. The difference between the right-eye movements and the difference between the left-eye movements are added and divided by the time length of the comparison period. For example, the difference of the eye movements between a2 and a0 is obtained in such a manner that the sum of the left-eye movement difference and the right-eye movement difference is 800 pixels, and 800 pixels are divided by the time length of 0.4 seconds of the comparison period, resulting in 2000 (pixel/ seconds). This is further divided by the depth movement amount, 370 mm, resulting in 5.4 (pixel×mm/second). In the similar manner, the fatigue level determining unit 240 obtains a fatigue index for eye movements in other comparison periods. Among the obtained fatigue indexes, the ratio of the fatigue indexes which exceed a predetermined fatigue criterion is obtained and determined as the level of fatigue (S2120). The fatigue criterion is, for example, 4.8 (pixel× mm/second). This value is experimentally obtained. In the example of FIG. 36, among the comparison periods other than a0, b0, and c0, a2 and c3 are the comparison periods which have fatigue indexes exceeding the fatigue criterion. The fatigue level determining unit 240 determines the level of fatigue at the current elapsed time Tp by the ratio of the comparison periods which exceeded the fatigue criterion among the fatigue indexes of comparison periods of the new test periods. In the example of FIG. 36, the fatigue indexes in two comparison periods among the three new test periods exceeded the fatigue criterion; and thus, the level of fatigue at the current elapsed time Tp is determined as 67%.

Referring back to FIG. 31, the output unit 250 determines if the level of fatigue obtained in Step S2120 is to be alerted (S1130). For example, when the level of fatigue is 50% or higher (Yes in S1130), the output unit 250 gives, to the player 100, a warning, indicating that the player 100 is having visual fatigue, on a display screen, by audio presentation headphones, or a loud speaker (S1140), and the process returns to Step S1030. On the other hand, when the level of fatigue does not exceed a predetermined value in Step S1130 (No in S1130), the process returns to Step S1030. While the player 100 is playing the game, Steps S1030 to S1140 are repeated.

In Variation 1 of Embodiment 1, as shown in FIG. 36, it is possible to obtain the level of fatigue which changes over time after the start of the game. Accordingly, processes may be performed such as outputting a warning when the level of fatigue rapidly increases.

As described above, a game machine which includes the visual fatigue level measuring device according to Variation 1 can identify visual targets at which the player 100 is gazing by controls input by the player 100 with respect to the visual targets, and can compare, over time, eye movements performed when the player 100 is gazing at the visual targets in a state where the player 100 is not fatigued immediately after the start of the game, with the eye movements performed when the player 100 is gazing at the visual targets while continuously playing the game. By presenting visual targets having the same or similar trajectories at intervals along with the story of the game, eye movements can be compared by using only video for the game. It is not necessary to interrupt the game for measuring the level of visual fatigue, or to perform calibration before starting the game. As a result, it is possible to provide a visual fatigue level measuring device which does not interrupt enjoyment of games.

Furthermore, as in Variation 1, by using, for measuring fatigue, eye movements performed when the player 100 moves the aim position from one visual target to another visual target, changes in the states of fast eye movements which are likely to cause fatigue are measured. This facilitates detection of visual fatigue of the player 100.

(Variation 2 of Embodiment 1)

Figure 37:
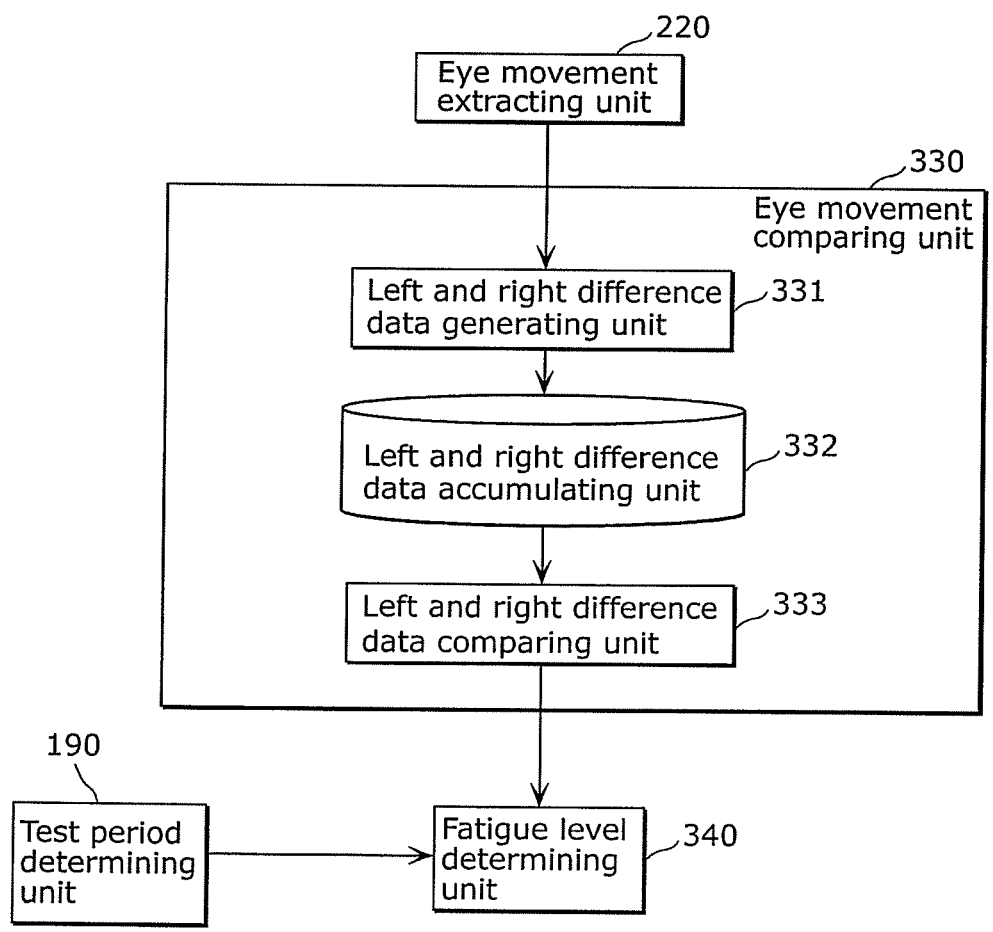
FIG. 37 is a block diagram illustrating an example of a detailed structure (portions different from Embodiment 1) of a game machine including a visual fatigue level measuring device according to Variation 2 of Embodiment 1.

The following describes Variation 2 of Embodiment 1. As shown in FIG. 37, Variation 2 of Embodiment 1 is the same as Embodiment 1 except the following points: the eye movement comparing unit 230 is replaced with an eye movement comparing unit 330; and the fatigue level determining unit 240 is replaced with a fatigue level determining unit 340. Thus, detailed descriptions are given only of the eye movement comparing unit 330, the fatigue level determining unit 340, and processes involved in these units.

In Embodiment 1, for comparing eye movements, comparison of right-eye movements and comparison of left-eye movements are separately performed. The level of fatigue is determined based on each comparison result of the left and right eyes. In Variation 2, the difference of positional information between the left and right eyes, that is, the difference between the angles of the eyes for stereoscopic viewing are obtained, and fatigue is determined based on the changes in the values of the differences between the eyes.

FIG. 37 shows a detailed structure of the eye movement comparing unit 330 according to Variation 2. The eye movement comparing unit 330 is a processing unit which compares eye movements using the difference between a pupil center position of the left eye and a pupil center position of the right eye, and includes a left and right difference data generating unit 331, a left and right difference data accumulating unit 332, and a left and right difference data comparing unit 333. The fatigue level determining unit 340 obtains, from the test period determining unit 190, movement trajectories of visual targets in comparison periods.

Figure 38:
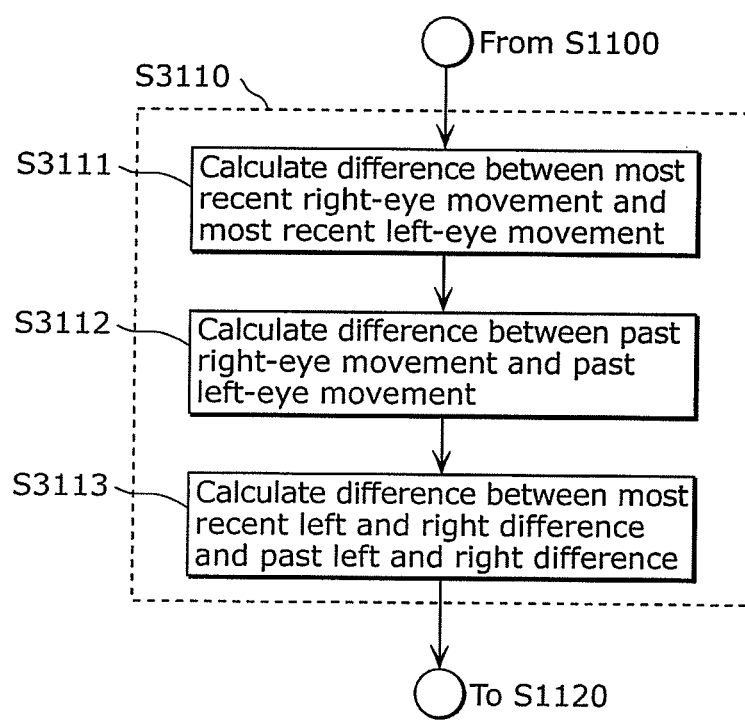
FIG. 38 is a flowchart of an example of the flow of the detailed processes of an eye movement comparing step (Step S3110) according to Variation 2 of Embodiment 1.

The same operations as those in Steps S1010 to S1100 in Embodiment 1 are performed in Variation 2. Step S1110 in Embodiment 1 is replaced with Step S3110 in Variation 2. FIG. 38 is a flowchart of details of Step S3110 (process for comparing eye movements).

Referring to FIG. 38, a detailed description is given of Step S3110. As in Embodiment 1, the gaze target identifying unit 160 identifies a visual target at which the player 100 is gazing by controls input by the player 100 with respect to the visual target. The eye movement extracting unit 220 extracts eye movements corresponding to the comparison periods from eye movement data 210a accumulated in the eye movement accumulating unit 210, in accordance with two comparable time periods that are the most recent testable period determined in Step S1090 and a past testable period that can be compared with the most recent testable period (S1100). The left and right difference data generating unit 331 obtains the difference of eye movements between the left and right eyes in the most recent time period among the eye movements obtained in Step S1100, and accumulates, in the left and right difference data accumulating unit 332, the difference as left and right difference data.

Here, the eye movements are expressed as coordinate data that represent the pupil center positions. The difference refers to the difference of the pupil center positions between the left and right eyes that is expressed two-dimensionally. FIG. 39 shows an example of the left and right difference data 332a accumulated in the left and right difference data accumulating unit 332. The left and right difference data 332a includes elapsed time from the start of the game, and differences between left and right eye positions in the horizontal direction and differences between left and right eye positions in the vertical direction at each elapsed time. The left and right difference data 332a is recorded for each time period. More specifically, the left and right difference data 332a is obtained as described below.

The coordinates of the center of the right eye pupil in the most recent time period are represented by Math 5.

$$(Rxp_i, Ryp_i) \quad \text{[Math 5]}$$

The coordinates of the center of the left eye pupil are represented by Math 6.

$$(Lxp_i, Lyp_i) \quad \text{[Math 6]}$$

The difference of the pupil center positions between the left and right eyes can be represented by Math 7.

$$(Lxp_i - Rxp_i, Lyp_i - Ryp_i) \quad \text{[Math 7]}$$

The "left and right difference of horizontal axis" in FIG. 39 is represented by Math 8.

$$Rxp_i - Lxp_i \quad \text{[Math 8]}$$

The "left and right difference of vertical axis" in FIG. 39 is represented by Math 9.

$$Ryp_i - Lyp_i \quad \text{[Math 9]}$$

3D video provides stereoscopic view by using differences in the horizontal direction between left and eye images, that is, parallax angle. The eye movements peculiar to stereoscopic viewing appear as the differences between horizontal movements of the left and right eyes. Thus, in Step S3111, only the difference between the pupil center positions in the horizontal direction may be calculated as the difference of the movements between the left and right eyes.

Furthermore, the left and right difference data generating unit 331 obtains the difference between eye movements of the left and right eyes for each time period that is within 20 minutes from the start of the game in the same manner as in S3111, and accumulates the obtained differences in the left and right difference data accumulating unit 332 (S3112).

The coordinates of the center of the right eye pupil in a time period within 20 minutes from the start of the game are represented by Math 10.

$$(Rxs_i, Rys_i) \quad \text{[Math 10]}$$

The coordinates of the center of the left eye pupil is represented by Math 11.

$$(Lxs_i, Lys_i) \quad \text{[Math 11]}$$

The difference between the pupil center positions of the left and right eyes can be represented by Math 12.

$$(Lxs_i - Rxs_i, Lys_i - Rys_i) \quad \text{[Math 12]}$$

The left and right difference data comparing unit 333 obtains the difference between (i) data of the difference, obtained in Steps S3111, of the movements between the left and right eyes in the most recent eye movements and (ii) data of the difference, obtained at S3112, of the movements between the left and right eyes within 20 minutes from the start of the game (S3113).

Here, with respect to the differences between pupil center positions of the left and right eyes at respective sample points, the left and right difference data comparing unit 333 obtains, for two time periods, the difference, that is, an absolute value of the difference at each sample point i having a starting point 0 in the time period. With respect to all of the sample points within the time period, the sum of the differences is obtained by Math 13.

$$\Sigma(|(Lxp_i - Rxp_i) - (Lxs_i - Rxs_i)| + |(Lyp_i - Ryp_i) - (Lys_i - Rys_i)|) \quad \text{[Math 13]}$$

The value thus obtained is determined as the difference between the most recent eye movements and the eye movements within 20 minutes from the start of the game.

Figure 40:
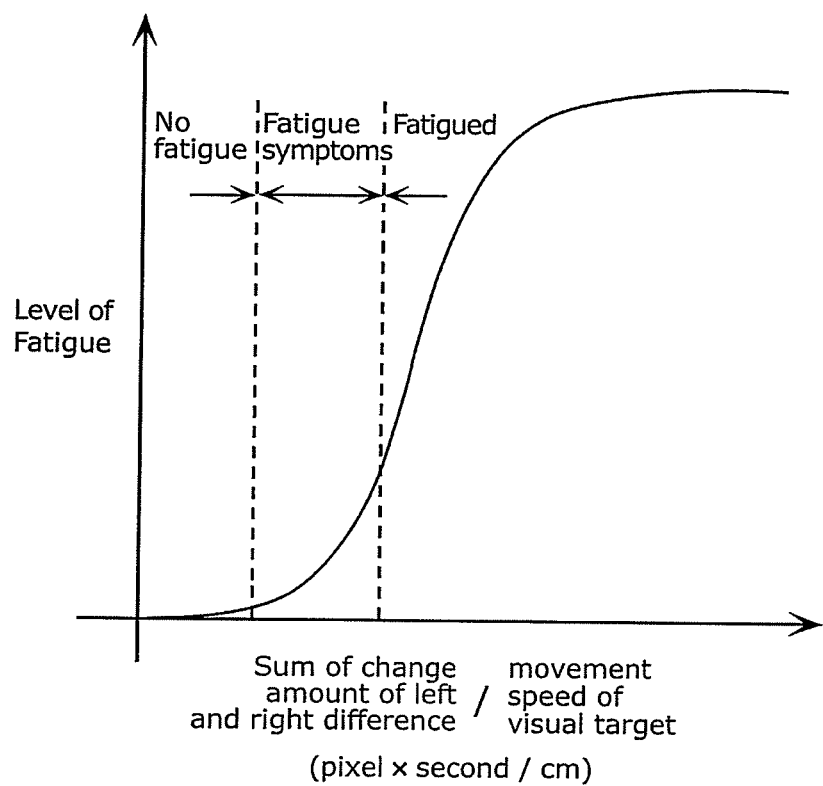
FIG. 40 is a diagram for explaining an example of a method for determining the level of fatigue according to Variation 2 of Embodiment 1.

The fatigue level determining unit 340 calculates the movement speed of the visual target based on trajectory information of the visual target in the time period that is obtained from the test period determining unit 190 for comparison. As shown in FIG. 6, the trajectory information of visual targets are accumulated as 3D coordinate positions at each elapsed time after the start of the game. The 3D coordinate positions are virtual positions of the visual targets with the head position of the player 100 as the origin. The fatigue level determining unit 340 obtains the movement distance (cm), in a 3D space, of a target having a region which overlaps the aim position in the time period, and the obtained movement distance is divided by the time length (seconds) of the time period, thereby determining the movement speed of the visual target. The fatigue level determining unit 340 calculates a fatigue index by dividing the difference which is obtained in Step S3113 and which is between (i) the difference between the most recent eye movements of the left and right eyes and (ii) the difference between the movements of the left and right eyes within 20 minutes from the start of the game, by the movement speed of the visual target. FIG. 40 schematically shows relationship between fatigue and "sum of change amount of left and right difference/movement speed of visual target" that is a fatigue level index.

The fatigue level determining unit 340 determines the level of fatigue by, for example, dividing into three regions: no fatigue, fatigue symptoms, and fatigued.

As described, a game machine including the visual fatigue level measuring device according to Variation 2 identifies a visual target at which the player 100 is gazing by controls input by the player 100 with respect to the visual target, and compares the eye movements performed when the player 100 is gazing at the visual target in the state where the player 100 is not fatigued immediately after the start of the game and the eye movements performed when the player 100 is gazing at the visual target in the state where the player 100 continuously playing the game. By presenting visual targets having the same or similar trajectory at intervals along the story of the game, it is possible to measure visual fatigue using only video for the game. It is not necessary to interrupt the game for measuring the level of visual fatigue, or to perform calibration before starting the game. As a result, it is possible to provide a visual fatigue level measuring device which does not interrupt enjoyment of games.

Furthermore, as in Variation 2, by calculating the level of fatigue according to the movement speed of the visual target at which the player 100 is gazing, it is possible to determine the level of fatigue appropriately when the eyes follow the movement of the visual target and different level of fatigue is caused depending on the speed of the visual target. More specifically, when the eyes follow fast movement of the visual target, fatigue is likely to occur, and when the eyes follow slow movement of the visual target, fatigue is less likely to occur. It is possible to determine visual fatigue of the player 100 regardless of the movement speed of the visual target, by dividing the difference between (i) the difference in the most recent eye movements between the left and right eyes and (ii) the difference in the eye movements between the left and right eyes within 20 minutes from the start of the game by the movement speed of the visual target and determining the obtained value as a fatigue level index. This allows the level of visual fatigue of the player 100 to be detected more correctly.

Embodiment 2

Figure 41:
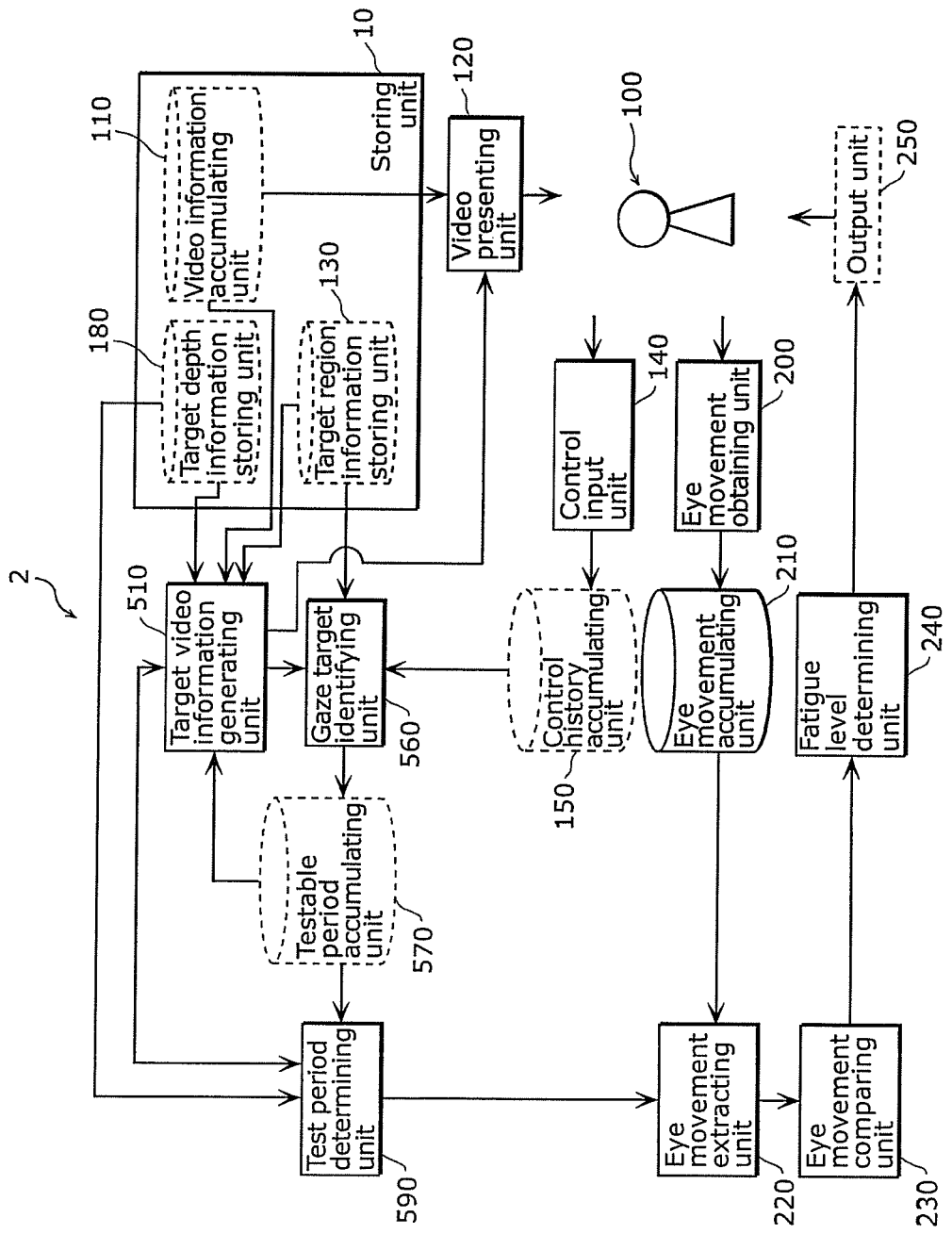
FIG. 41 is a block diagram illustrating an example of an overall structure of a game machine including a visual fatigue level measuring device according to Embodiment 2.

Next, a description is given of Embodiment 2 of the present disclosure. FIG. 41 is a diagram showing a structure of a visual fatigue level measuring device 2 according to Embodiment 2. The elements same as those in FIG. 3 according to Embodiment 1 are labeled with the same reference numerals, and their descriptions are omitted.

The visual fatigue level measuring device 2 according to Embodiment 2 has the same structure as that of the visual fatigue level measuring device 1 shown in FIG. 3 according to Embodiment 1 except the following points: the gaze target identifying unit 160 is replaced with a gaze target identifying unit 560, the testable period accumulating unit 170 is replaced with a testable period accumulating unit 570, the test period determining unit 190 is replaced with a test period determining unit 590, and a target video information generating unit 510 is added.

The visual fatigue level measuring device 2 includes: the video information accumulating unit 110; the video presenting unit 120 which presents 3D video to the player 100; the target region information storing unit 130; the control input unit 140; the control history accumulating unit 150; a target video information generating unit 510; a gaze target identifying unit 560; a testable period accumulating unit 570; a target depth information storing unit 180; a test period determining unit 590; the eye movement obtaining unit 200; the eye movement accumulating unit 210; the eye movement extracting unit 220; the eye movement comparing unit 230; and the fatigue level determining unit 240.

The target video information generating unit 510 is a processing unit which generates video including a visual target based on information which indicates a testable period accumulated in the testable period accumulating unit 570. Here, when the test period determining unit 590 cannot determine a comparison period which is testable, the target video information generating unit 510 generates video which can be used for a test, using video information 110a accumulated in the video information accumulating unit 110 in accordance with trajectory information of a visual target in a testable period accumulated in the testable period accumulating unit 570.

Figure 42:
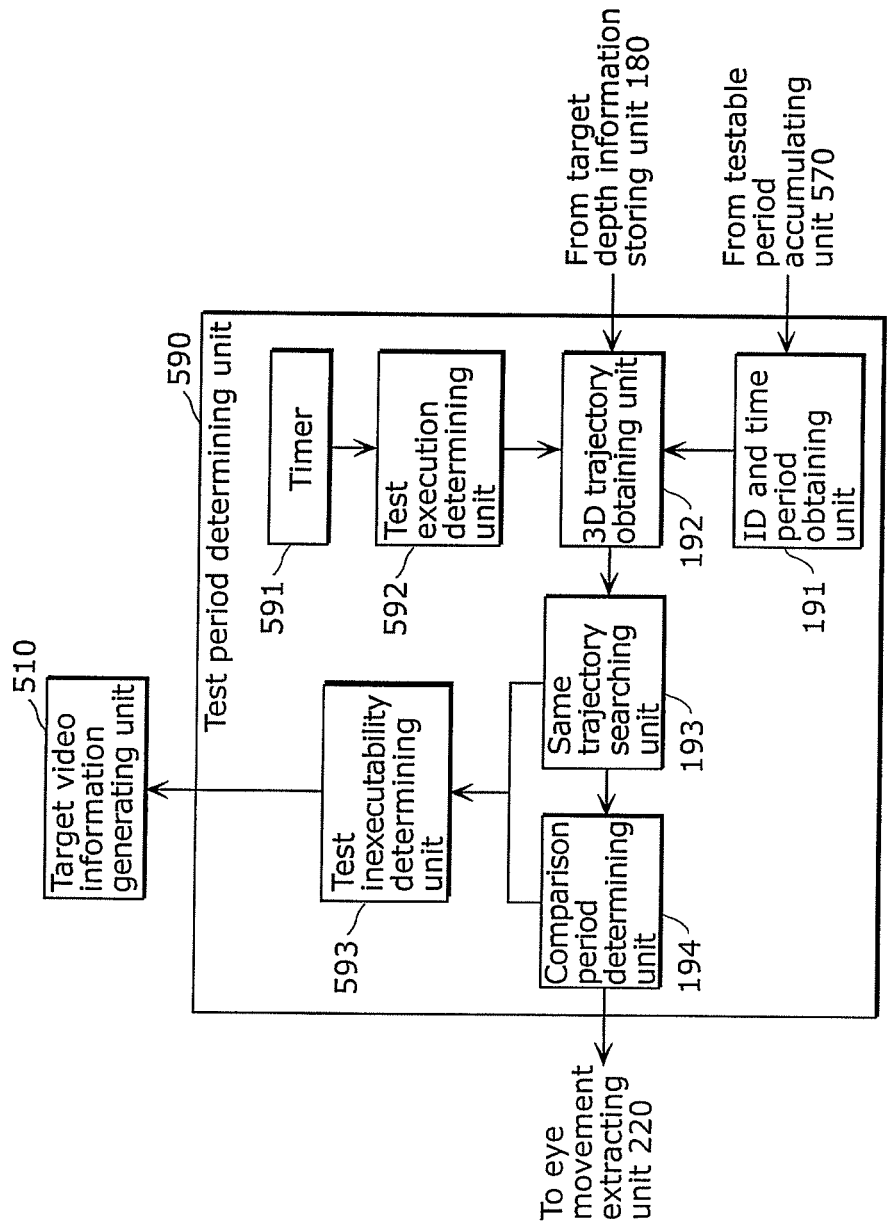
FIG. 42 is a block diagram illustrating an example of a detailed structure of a test period determining unit shown in FIG. 41.
Figure 43:
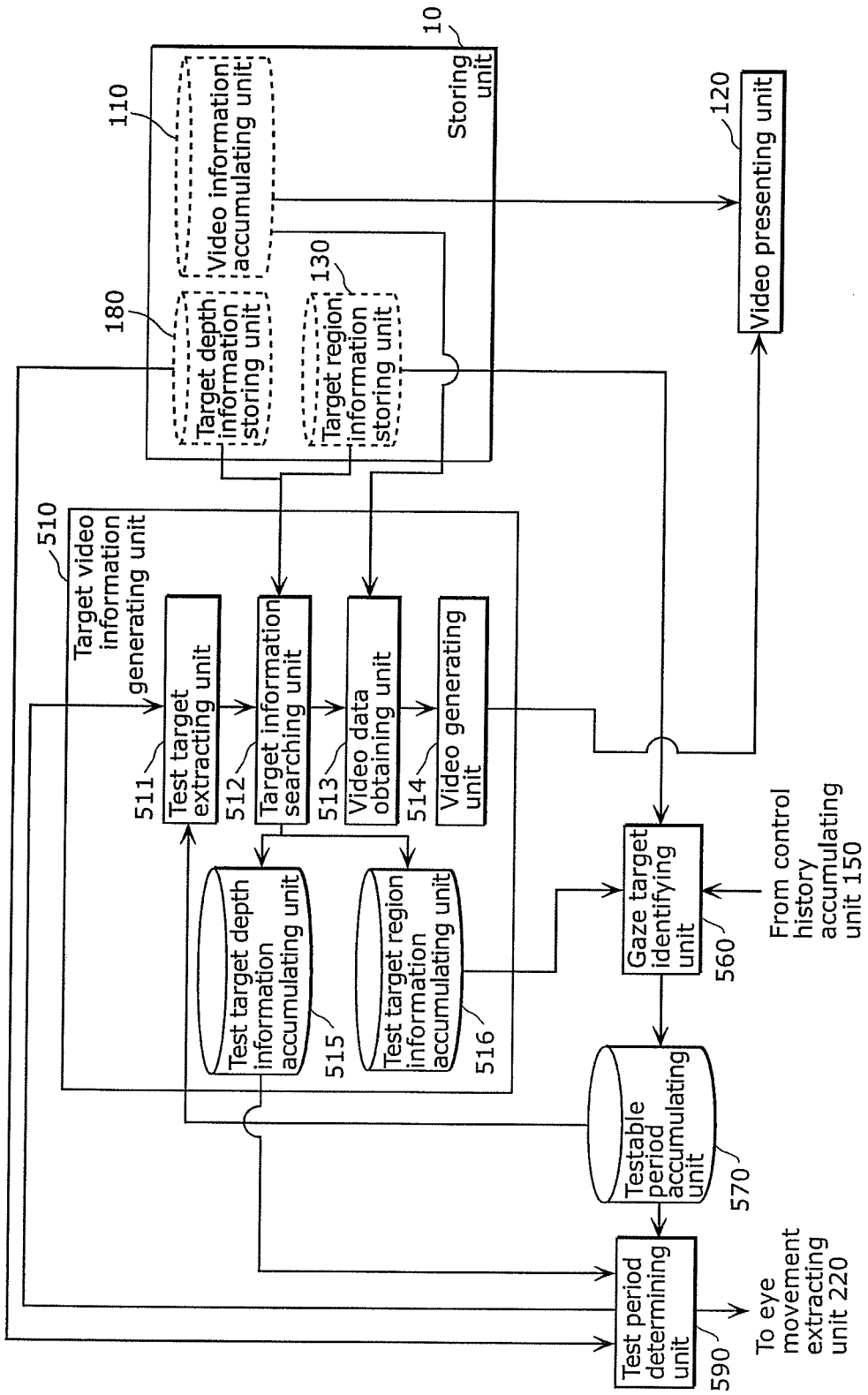
FIG. 43 is a block diagram illustrating an example of a detailed structure of a target video information generating unit shown in FIG. 41.

FIG. 42 is a part of a detailed structure of the test period determining unit 590 included in the visual fatigue level measuring device 1 according to Embodiment 2, and FIG. 43 is a part of a detailed structure of the target video information generating unit 510 included in the visual fatigue level measuring device 1.

FIG. 42 shows a detailed structure of the test period determining unit 590 shown in FIG. 41. The same elements as those in FIG. 12 according to Embodiment 1 are labeled with the same reference numerals, and their descriptions are omitted.

The test period determining unit 590 includes: the ID and time period obtaining unit 191; a timer 591 which measures time period during which games are being continuously played without fatigue level tests; a test execution determining unit 592 which determines the execution of fatigue level tests according to the time period during which the games are being continuously played without the fatigue level tests; the 3D trajectory obtaining unit 192; the same trajectory searching unit 193; the comparison period determining unit 194; and a test inexecutability determining unit 593 which determines that a test is inexecutable when a comparison period cannot be set such as a case where no testable period exists which has the same trajectory as the most recent testable period, or a case where no comparable period exists immediately after the start of the game.

FIG. 43 shows a detailed structure of the target video information generating unit 510 shown in FIG. 41. The target video information generating unit 510 includes: a test target extracting unit 511 which obtains information of a visual target from a testable period immediately after the start of the game; a target information searching unit 512 which obtains information of a visual target included in a testable period immediately after the start of the game; a video data obtaining unit 513 which obtains video of test visual targets; a video generating unit 514 which generates video which includes test visual targets; a test target depth information accumulating unit 515 which accumulates trajectory information of test visual targets; and a test target region information accumulating unit 516 which accumulates regions of test visual targets on the screen and information of time periods of the test visual targets.

Figure 44:
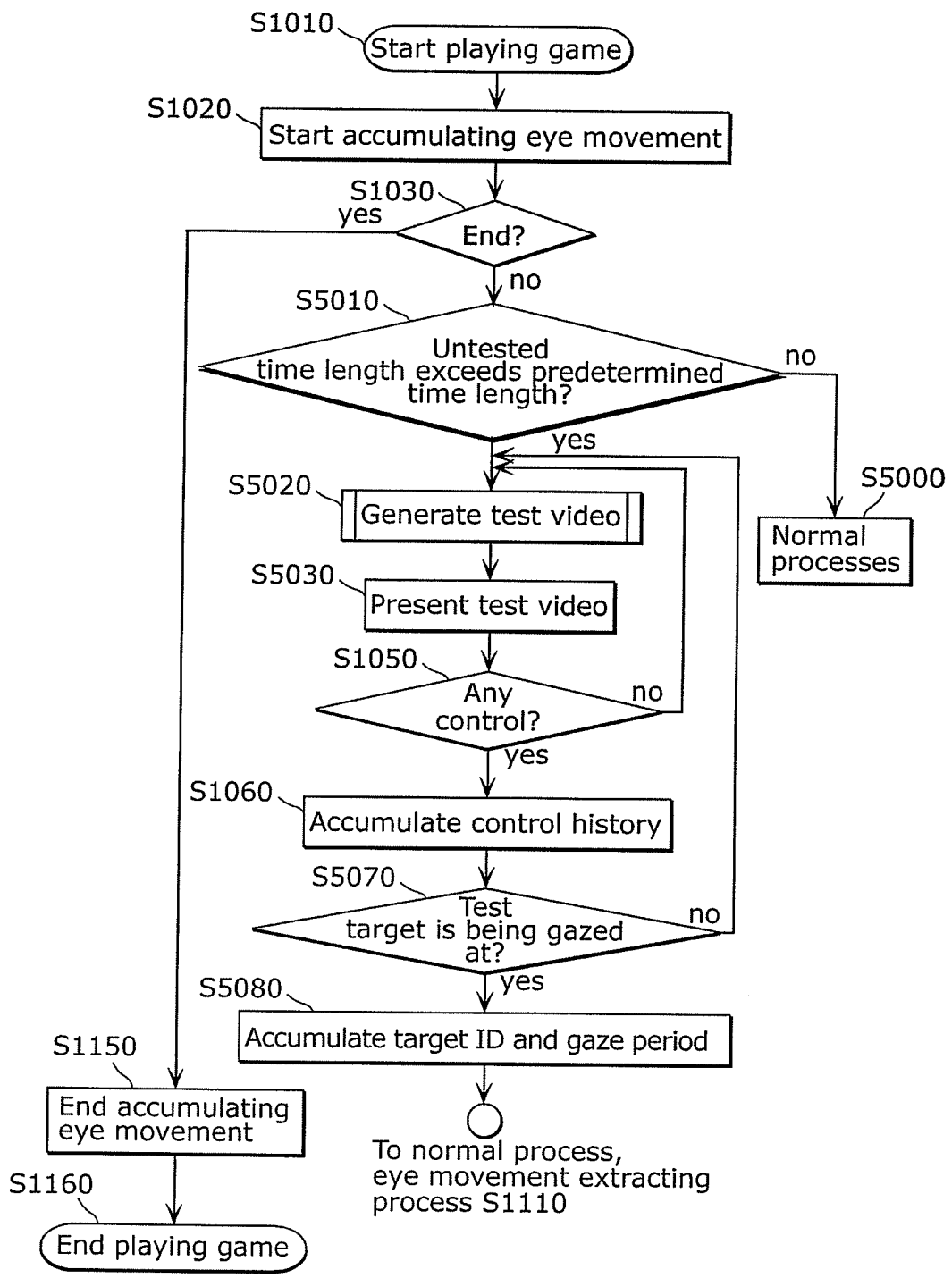
FIG. 44 is a flowchart of an example of the operations of a game machine including the visual fatigue level measuring device according to Embodiment 2.

Referring to FIG. 44, a description is given of the operations of the visual fatigue level measuring device 2 according to Embodiment 2.

FIG. 44 is a flowchart of the operations of the visual fatigue level measuring device 2 according to Embodiment 2. The operations after Step S1040 in Embodiment 1 are considered to be normal processes S5000 here, and its description is omitted. The same operations as those in FIG. 18 according to Embodiment 1 are labeled with the same reference numerals, and its description may be omitted.

First, the player 100 starts a game (S1010). When the game starts, the eye movement obtaining unit 200 starts measuring eye movements of both eyes, and accumulates the measurement results as eye movement data 210a in the eye movement accumulating unit 210 (S1020). The eye movement obtaining unit 200 checks if a command for ending the game has been input (S1030). In Step S1030, when the command for ending the game has been input (Yes in S1030), the process proceeds to Step S1150, and the eye movement obtaining unit 200 ends accumulating the eye movements (S1150). After ending the accumulation of the eye movements, the game ends (S1160).

On the other hand, when no command for ending the game has been input in Step S1030 (No in S1030), the process proceeds to Step S5010. In S5010, the test period determining unit 590 determines if the time length during which the player 100 is continuously playing the game without fatigue level tests exceeds a predetermined time length (S5010). The timer 591 in the test period determining unit 590 measures time elapsed from the start of the game time elapsed from the most recent fatigue level test. When the time length measured by the timer 591 exceeds a predetermined time length, for example, 30 minutes (Yes in S5010), the test execution determining unit 592 in the test period determining unit 590 determines the execution of a test. On the other hand, when the time length during which no test is executed does not exceed a predetermined time length (No in S5010), the process proceeds to the normal operations Step S5000. In the normal operations Step S5000, when a test cannot be executed on the most recent testable period because of the reasons such as no visual target exists which has the same trajectory as that in the most recent testable period or no data exists which corresponds to a testable period within 20 minutes from the start of the game, the process returned to Step S1030 in Embodiment 1; however, in Embodiment 2, information indicating that tests are inexecutable is output to the test inexecutability determining unit 593 in the test period determining unit 590.

When it is determined in Step S5010 that the time length with no test exceeds a predetermined time length (Yes in S5010), the test inexecutability determining unit 593 outputs information indicating that tests are inexecutable, and the process proceeds to Step S5020. The target video information generating unit 510 generates test video, and accumulates trajectory information of test visual targets in the test target depth information accumulating unit 515, and accumulates region information and time information of test visual targets, in the test target region information accumulating unit 516 (S5020). The video presenting unit 120 presents the test video generated in Step S5020 to the player 100 (S5030). Here, the control input unit 140 checks if the player 100 has controlled the control input unit 140 with respect to the video presented in Step S5030 (S1050). When there is no control by the player 100 in Step S1050 (No in 1050), the process returns to Step S5020. On the other hand, when there are controls by the player 100 in Step S1050 (Yes in S1050), the control input unit 140 accumulates a series of controls that are input, as control history 150a in the control history accumulating unit 150 (S1060).

The gaze target identifying unit 560 then determines if the player 100 keeps gazing at a test visual target (S5070). When the player 100 is not gazing at the test visual target in S5070 (NO in S5070), the process returns to Step S5020. On the other hand, when the player 100 is gazing at the test visual target in Step S5070 (Yes in S5070), the process proceeds to Step S5080. In Step S5080, the testable period accumulating unit 570 accumulates an ID used by the video target information generating unit 510 for identifying the test visual target and the time period during which the player 100 was gazing at the visual target, as a testable period (S5080). The test period determining unit 590 extracts, from the test target depth information accumulating unit 515, trajectory of the virtual positions of the test visual target accumulated in the testable period accumulating unit 570 in Step S5080, extracts the testable period that was used for setting the test visual target, and determines the time period which corresponds to the gaze period with respect to the test visual target (S5090). As a result, two time periods are set. The subsequent processes are the same as the processes after Step S1100 according to Embodiment 1, and thus, its description is omitted.

Figure 45:
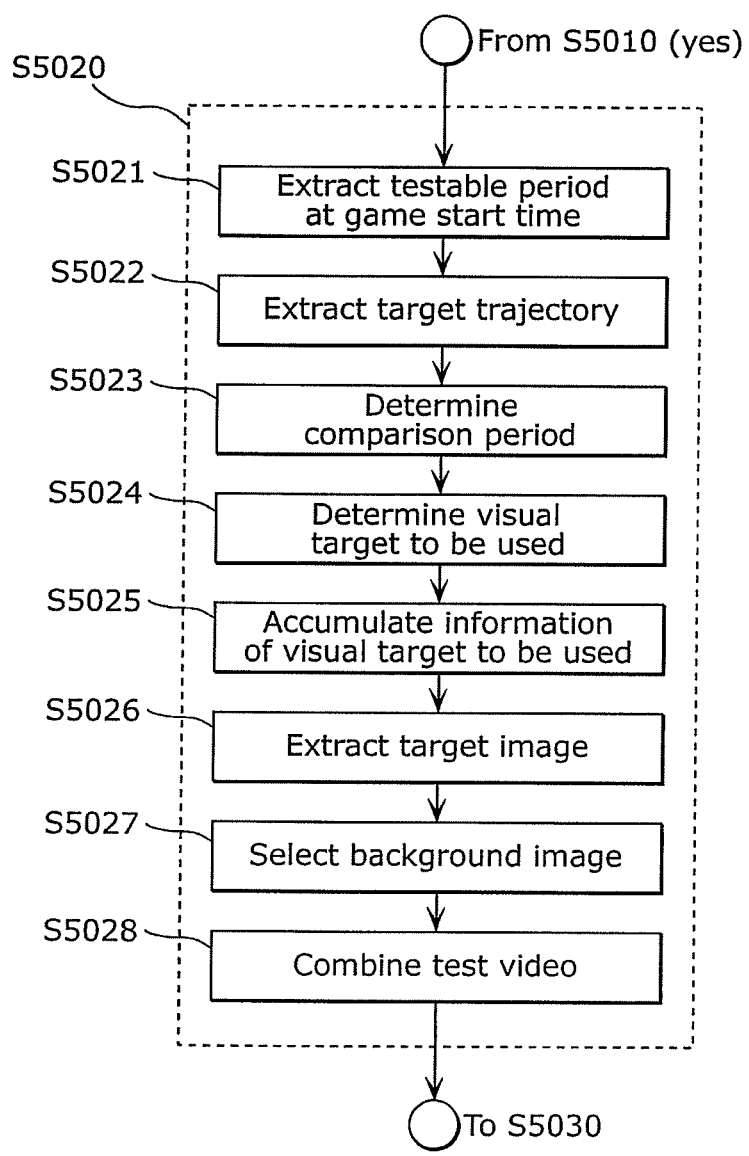
FIG. 45 is a flowchart of an example of the flow of the detailed processes in a test video generating step (Step S5020 in FIG. 44) according to Embodiment 2.

The following describes a detail of Step S5020 where the target video information generating unit 510 generates test video, with reference to FIG. 45. When tests cannot be executed and the time length with no test exceeds a predetermined time length in Step S5010 (Yes in S5010), the test target extracting unit 511 first extracts, from the testable period accumulating unit 570, a testable period which has a time period that is within a time period that can be considered that the player 100 is not fatigued after the start of the game, for example, a time period that is within 20 minutes from the start of the game (S5021). The target information searching unit 512 extracts, from the target depth information storing unit 180, movement trajectory of a visual target (target depth information 180a) in the testable period (S5022). When there are a plurality of testable periods, the target information searching unit 512 selects, as a comparison period, a testable period including a visual target which has a trajectory with a large depth movement. The large depth movement causes large eye movements, facilitating the detection of fatigue (S5023). Furthermore, the target information searching unit 512 searches the target depth information storing unit 180 for a visual target which has the same trajectory as the visual target in the comparison period. When no visual target exists which has the same trajectory as the visual target in the comparison period, or when no visual target exists which has the same trajectory other than the visual target in the comparison period, the target information searching unit 512 determines the visual target in the comparison period as a visual target to be used. (S5024). When a plurality of visual targets exist which have the same trajectory, a visual target is selected which is included in a scene having lightness information or contrast information close to those in the comparison period. The target information searching unit 512 then accumulates, in the test target depth information accumulating unit 515, movement trajectory of the visual target to be used determined in Step S5024. The target information searching unit 512 further accumulates, in the test target region information accumulating unit 516, region information of the visual target to be used and relative time position information in test video (S5025).

Next, the video data obtaining unit 513 extracts video information 110a of the visual target to be used from the video information accumulating unit 110, based on the ID, time period, and region information of the visual target to be used (S5026). The video data obtaining unit 513 extracts, from the video information accumulating unit 110, a background image which has a contrast equivalent to that in the comparison period (S5027). Finally, the video generating unit 514 overlays video of the visual target indicated by the video information 110a extracted in Step S5026 on the background image extracted in Step S5027 (S5028). The video indicated by the video information 110a extracted from the video information accumulating unit 110 is 3D video. In the image processing, right-eye video and left-eye video are combined.

In cases where visual targets having the same or similar trajectory are not presented for a long period of times during the game, and tests for measuring the level of fatigue are executed for a long period of time because the operations by the player 100 with respect to the game are insufficient to execute the tests, it is possible for the visual fatigue level measuring device 2 according to Variation 2 to measure the level of fatigue where necessary without interrupting the game, by generating and inserting test video into game content for securing executing tests. As a result, it is possible to provide the visual fatigue level measuring device 2 which does not interrupt enjoyment of games. In particular, when the story of the game changes according to selections of the player 100, such as a role-playing game, and when a pair of time periods during which visual targets are presented for comparing eye movements cannot be prepared, the story of the game is narrowed down, and video that can be compared with the accumulated testable periods is presented for securely executing tests. As a result, it is possible to prevent the player 100 from continuously playing the game for a long period of time without measuring the level of fatigue and from accumulating fatigue.

Embodiment 3

Figure 46A:
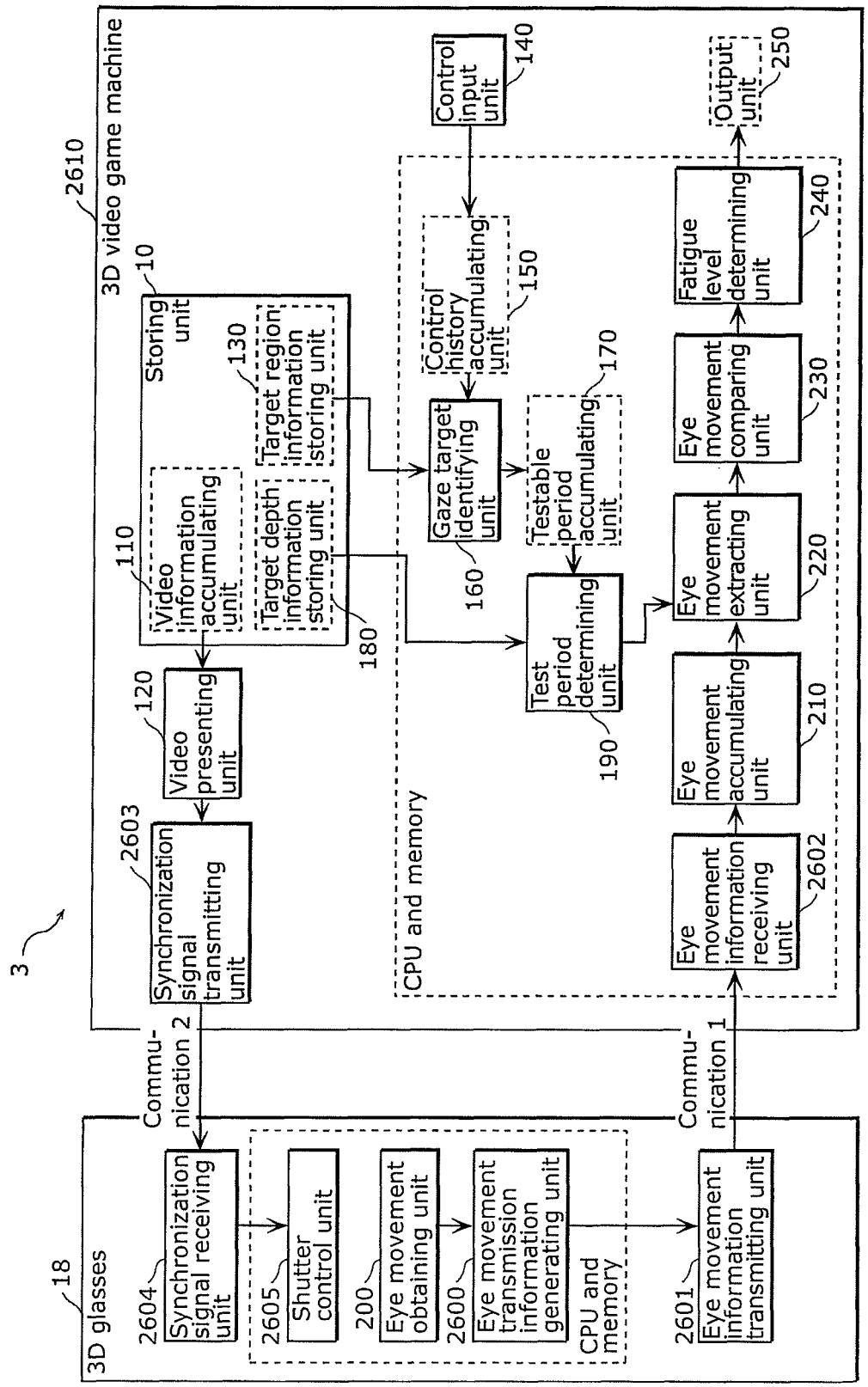
FIG. 46A is a block diagram illustrating an example of an overall structure of a visual fatigue level measuring device according to Embodiment 3.

In Embodiment 3, a description is given of a structure of a visual fatigue level measuring device 3 in which 3D glasses 18 and a 3D video game machine including a device for displaying images perform bidirectional communication. FIG. 46A shows an example of a structure of the visual fatigue level measuring device 3. In FIG. 46A, the blocks that have been described in the other Embodiments are labeled with the same reference numerals. The 3D video game machine 2610 is an example of an image display device for displaying 3D video.

The visual fatigue level measuring device 3 includes, in addition to the structure of the visual fatigue level measuring device 1 shown in FIG. 1, an eye movement transmission information generating unit 2600, an eye movement information transmitting unit 2601, an eye movement information receiving unit 2602, a synchronization signal transmitting unit 2603, a synchronization signal receiving unit 2604, and a shutter control unit 2605.

The eye movement transmission information generating unit 2600 processes the eye movement data of the player 100 measured by the eye movement obtaining unit 200 into a predetermined transmission format.

The eye movement information receiving unit 2602 transmits eye movement information of the player 100 generated by the eye movement transmission information generating unit 2600.

The synchronization signal transmitting unit 2603 transmits synchronization signals for switching between left-eye images and right-eye images, with respect to the images presented by the video presenting unit 120.

The synchronization signal receiving unit 2604 receives the signals transmitted from the synchronization signal transmitting unit 2603 in the 3D video game machine 2610.

The shutter control unit 2605 controls right-eye and left-eye shutters of the 3D glasses 18 based on the signals received by the synchronization signal receiving unit 2604. The right-eye shutter blocks right-eye video so that images are not presented to the right eye. The left-eye shutter blocks left-eye video so that images are not presented to the left eye.

Figure 49:
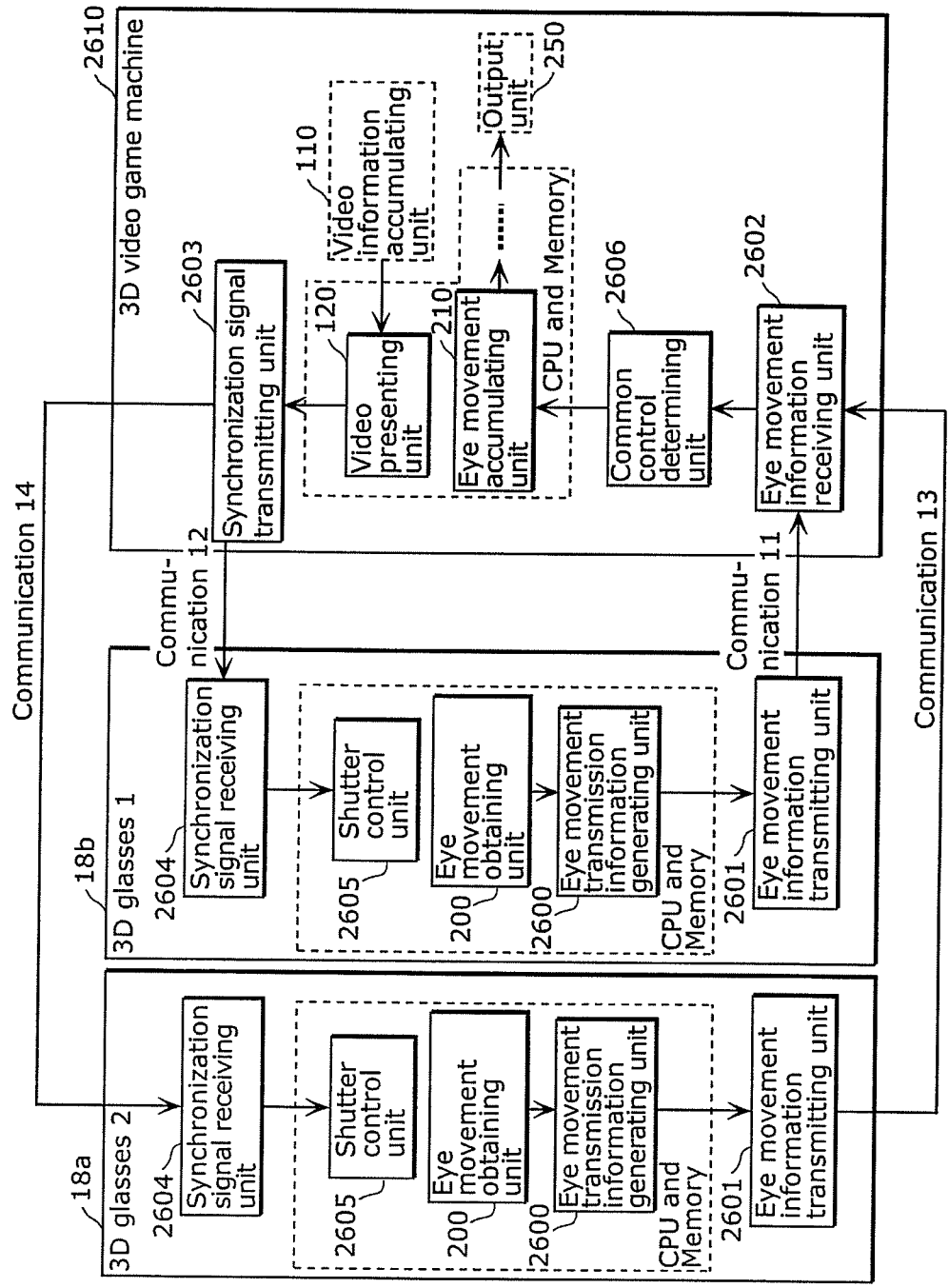
FIG. 49 is a block diagram illustrating an example of an overall structure of a visual fatigue level measuring device according to Variation of Embodiment 3.
Figure 51:
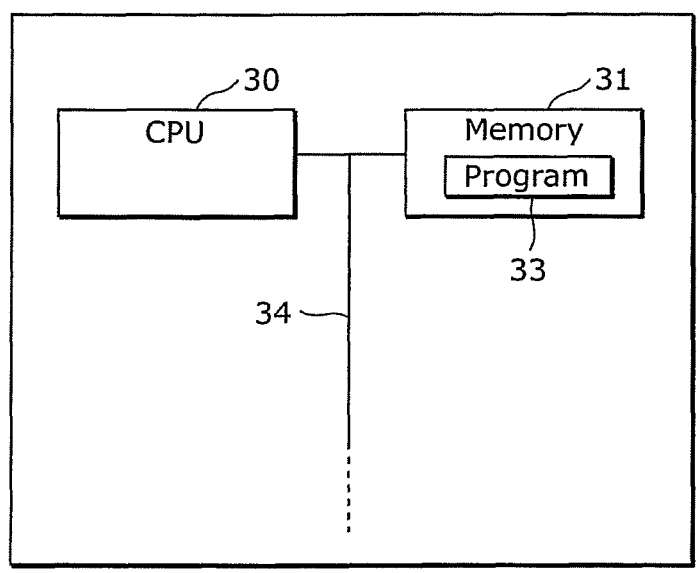
FIG. 51 is a diagram of a structure of a computer system implementing part of structural elements included in the visual fatigue level measuring device according to Embodiment 3.

In the case where the structural elements surrounded by dashed lines in FIG. 46A and FIG. 49 that will be described later are implemented by software, as shown within the square surrounded by the dashed lines, they are typically implemented by a memory 31 storing a program 33 and CPU 30 in a computer system shown in FIG. 51.

In the system having such a structure, the structural elements described in Embodiment 1 performs the same operations.

Figure 46B:
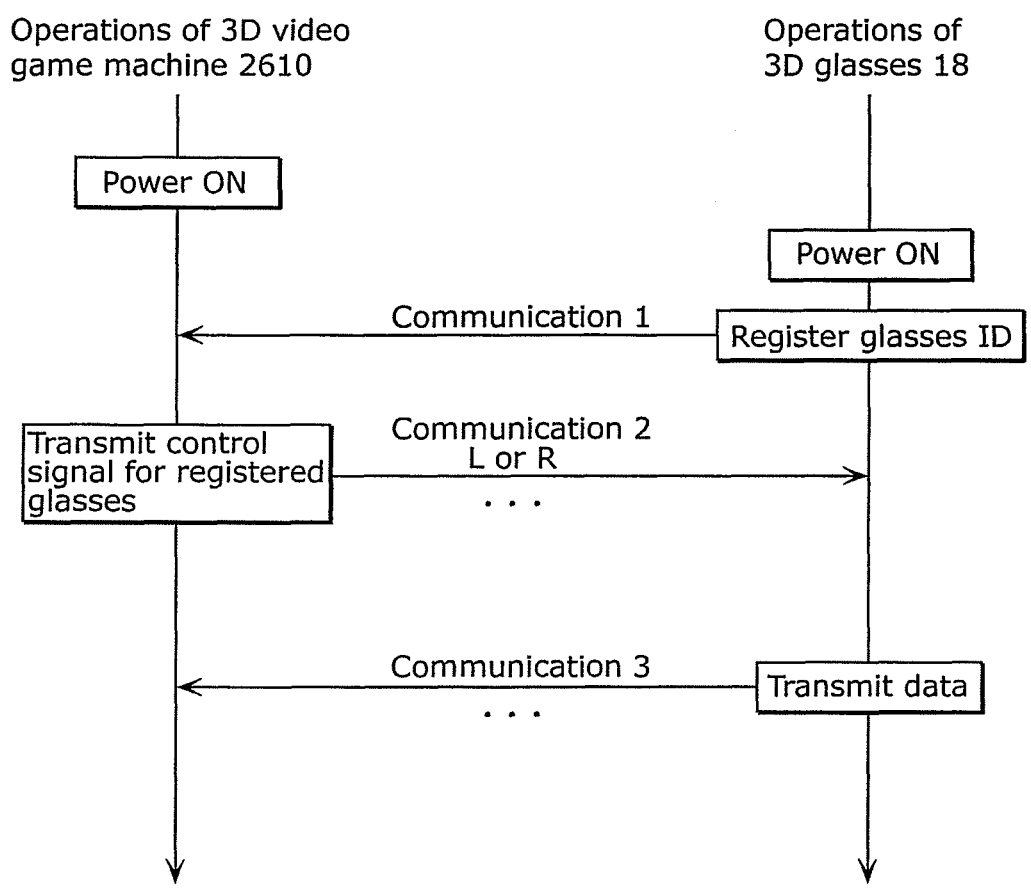
FIG. 46B is a diagram illustrating communication performed between a 3D video game machine and 3D glasses that are included in the visual fatigue level measuring device.

In Embodiment 3, a more detailed description is given of communication performed between the 3D glasses 18 and the 3D video game machine 2610. The communication between the 3D glasses 18 and the 3D video game machine 2610 in this system is assumed to be close-range wireless communication as represented by Bluetooth (registered trademark), ZigBee (registered trademark), wireless LAN or the like. FIG. 46B shows communication performed between the 3D video game machine 2610 and the 3D glasses 18. When the 3D glasses 18 are turned on, the 3D glasses 18 transmits their own ID (communication 1) to notify the 3D video game machine 2610 that the power of the 3D glasses having the ID is turned on.

The 3D video game machine 2610 receives the signal, and the ID of the 3D glasses 18 is registered. After that, a control signal for opening or closing liquid crystal shutters of the 3D glasses 18 is transmitted to the registered 3D glasses 18 (communication 2).

Here, data of eye movements of the player 100 measured by the eye movement obtaining unit 200 is transmitted to the 3D video game machine 2610 at a predetermined timing (communication 3).

Figure 47:
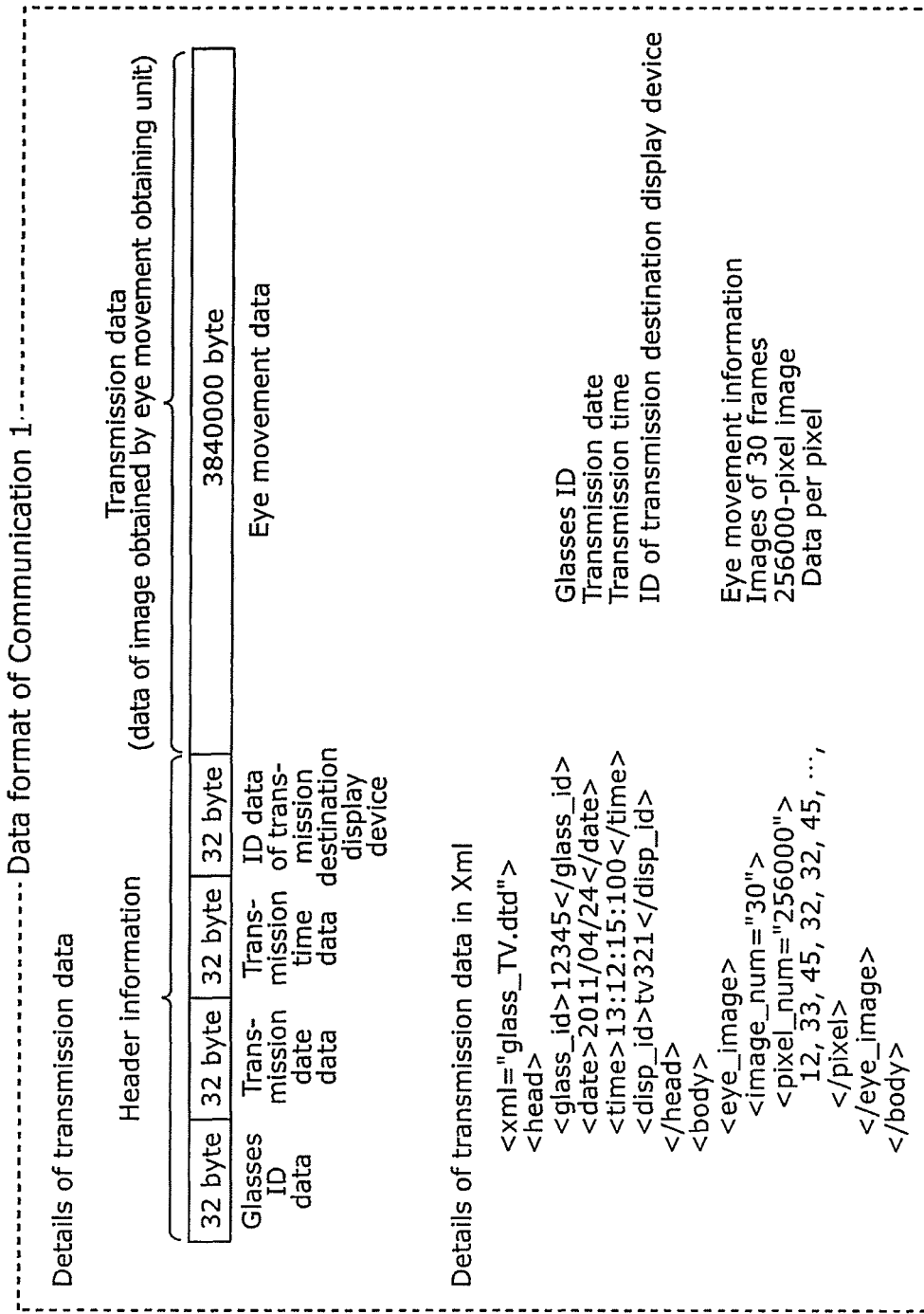
FIG. 47 shows a data format of communication 1 in FIG. 46A and FIG. 46B.

The eye movement transmission information generating unit 2600 generates transmission information which includes a glasses ID, transmission date, transmission time, transmission destination display device ID, and eye movement data, as in the data format of communication 1 shown in FIG. 47.

The eye movement information transmitting unit 2601 transmits, to the 3D video game machine 2610, information shown in FIG. 47 generated by the eye movement transmission information generating unit 2600.

As shown in FIG. 47, data such as binary data, text data, or XML format data are transmitted (communication 3).

The 3D video game machine 2610 transmits a timing signal for synchronously displaying a left-eye image and a right-eye image of the video presenting unit 120, from the synchronization signal transmitting unit 2603 to the 3D glasses 18.

Figure 48:
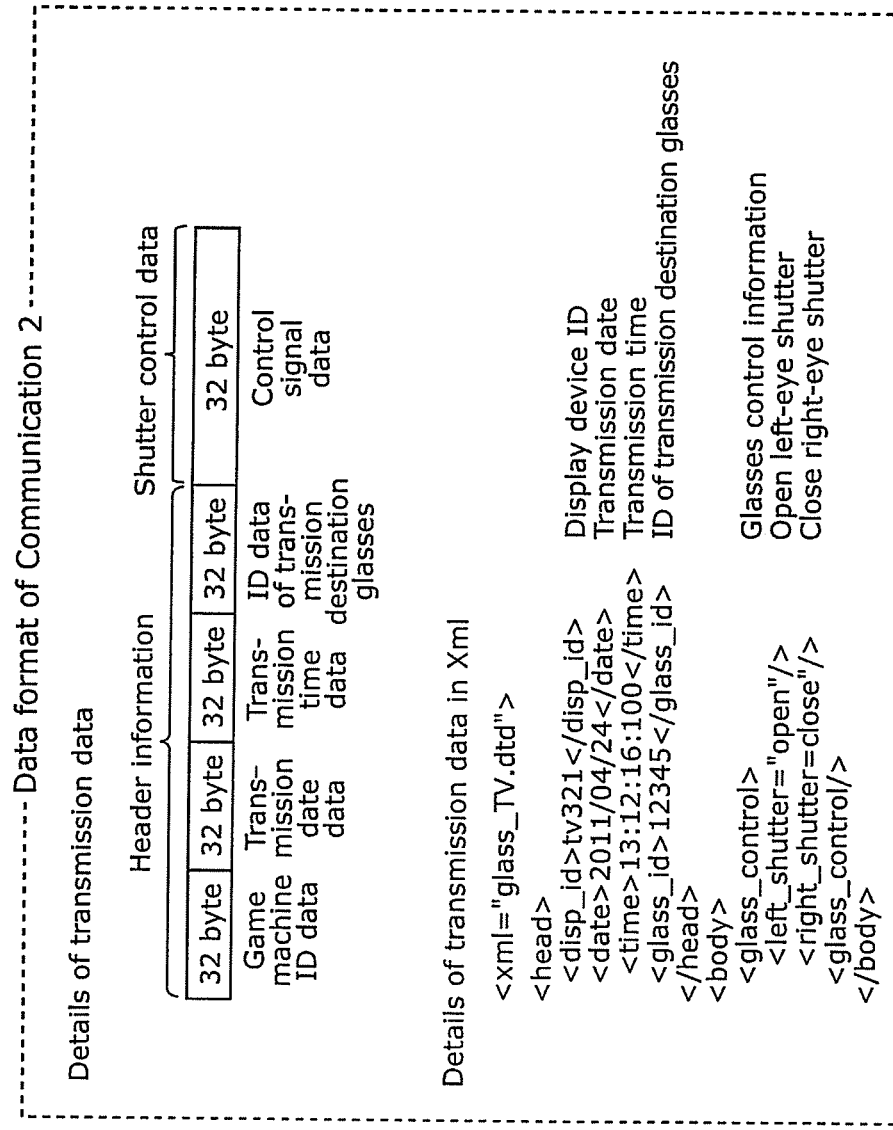
FIG. 48 shows a data format of communication 2 in FIG. 46A and FIG. 46B.

As shown in the data format of the communication 2 in FIG. 48, the signal transmitted from the 3D video game machine 2610 to the 3D glasses 18 includes a transmission source game machine ID, transmission date, transmission time, transmission destination glasses ID, and shutter control signals. As shown in FIG. 48, binary data, text data, or XML format data are transmitted. By using bidirectional wireless communication between the 3D glasses 18 and the 3D video game machine 2610, it is possible to control images of the 3D video game machine 2610 according to information of eye movements of the player 100.

The number of players who play games using the 3D video game machine may not be one. A plurality of players may play games using the 3D video game machine 2610. In such a case, as shown in a variation of Embodiment 3 in FIG. 49, 3D glasses 1 (18b) and 3D glasses 2 (18a) perform bidirectional communication with the 3D video game machine 2610 (communication 11 to 14). Different outputs are performed according to the level of fatigue of each player 100, based on the eye movements of the player 100. However, in cases where a plurality of players are playing a game, and where one player is determined to have fatigue based on the eye movements of the player, giving a warning or the like according to the player results in interrupting the other players.

Figure 50:
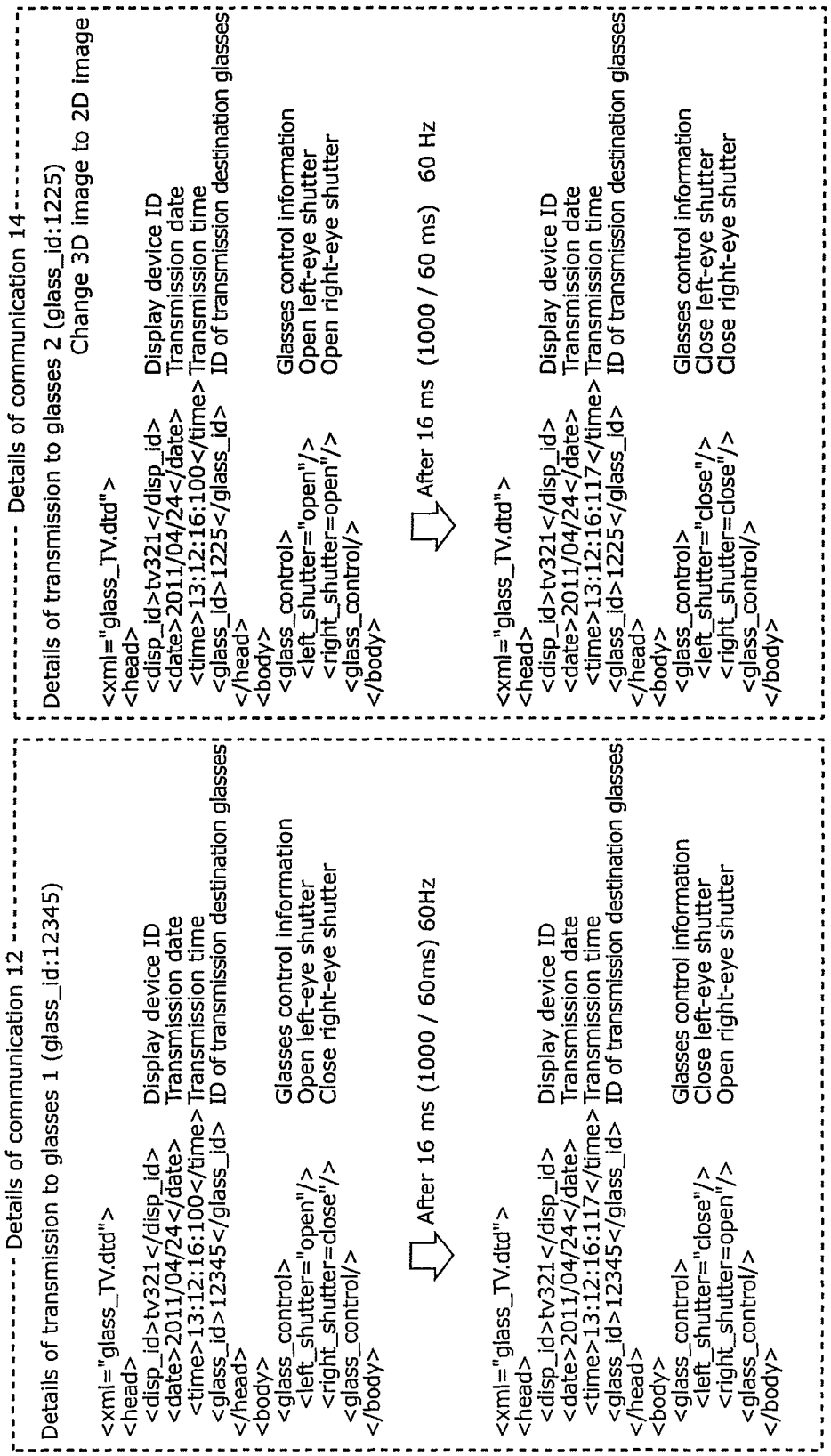
FIG. 50 shows data formats of communication 12 and 14 in FIG. 49.

In Embodiment 3, for example, in cases where fatigue is determined from the eye movement information transmitted from the 3D glasses 2 (18a) (communication 13), 2D video is presented to the 3D glasses 2(18a) by opening the left-eye and right-eye shutters while a left-eye image is being presented, and closing the left-eye and right-eye shutters while a right-eye image is being presented (communication 14). FIG. 50 shows the details of the communication (communication 12 and communication 14) at this time. As shown in FIG. 50, the 3D video game machine 2610 transmits, to the 3D glasses 1 (18b), a signal for alternately opening left and right shutters, and transmits, to the 3D glasses 2 (18*a*), a signal for synchronously opening and closing the left and right shutters. When the approximately same level of fatigue is determined for the 3D glasses 1 (18*b*) and the 3D glasses 2 (18*a*), a warning display or the like is output. In this way, even when a plurality of players are playing a game, different processing can be performed in accordance with the level of fatigue of each player. As described, the visual fatigue level measuring device according to Embodiment 3 is configured as a visual fatigue level measuring system which includes an image display device for displaying 3D video (for example, a 3D video game machine), and 3D glasses for viewing the 3D video. The 3D glasses include: an eye movement obtaining unit which measures eye movements of a user; and the eye movement information transmitting unit which transmits the eye movement information measured by the eye movement obtaining unit to the image display device having a video presenting unit which presents the 3D video. The image display device includes: an image accumulating unit which accumulates images to be presented to the left eye and the right eye of the users; and a fatigue level determining unit which determines the level of visual fatigue of the user based on the eye movement information of the user transmitted from the 3D glasses. The visual fatigue level measuring device according to Embodiment 3 is implemented by such a system having the image display device and the 3D glasses.

In Embodiment 3, the 3D glasses transmit eye movement information to the image display device, and the image display device determines the level of visual fatigue; however, the present disclosure is not limited to this. It may be that information that is necessary for determining the level of visual fatigue and that is obtained by the image display device is transmitted to the 3D glasses so that the 3D glasses determine the level of visual fatigue. In this case, it may be that the 3D glasses are used for viewing 3D video including images to be presented to the left and right eyes and that the 3D glasses include an eye movement obtaining unit which measures eye movements of the user; and a fatigue level determining unit which receives the eye movement information of the user from the eye movement obtaining unit and determines the level of visual fatigue of the user based on the eye movement information of the user. This allows the 3D glasses to calculate the level of visual fatigue.

The herein disclosed subject matter is to be considered descriptive and illustrative only, and the appended Claims are of a scope intended to cover and encompass not only the particular embodiments and variations disclosed, but also equivalent structures, methods, and/or uses.

For example, when a plurality of players 100 play a game in the above embodiments and variations, the level of fatigue may be determined for each player 100.

Furthermore, in Embodiments 1 to 3, the processes from the start to the end of the game have been described; however, it may be that a storing unit is included which stores the states of visual fatigue of respective players 100, and an individual player processing unit is included which studies the states of fatigue in past game plays of each player 100 for performing different processing suited to each player 100. This allows processing with higher accuracy to be performed with respect to changes in fatigue state of each player.

Furthermore, in the above embodiments and variations, fatigue states are quantitatively measured from eye movements. Here, by using the quantitative level of fatigue and the elapsed time, it is possible to predict, for each user, a time period during which the user is capable of playing the game continuously. In particular, when playing a game with a story line, it may be difficult to interrupt the game even if a message concerning fatigue is given by the system. Thus, it may be that by estimating the time point at which interrupting the game is likely to be accepted, based on the degree of progress of the game and the level of fatigue of the eyes of the user, and an advice is given to the user at the time point.

For example, when fatigue symptoms are detected and when it is determined that the user will be in a fatigued state in 30 minutes or so, and if the game has a breakpoint at that moment, the user may continue playing the game for a little while, however, at that point, the system may suggest the user to save the game. As described, it is also possible to suggest, to the user, the time when the game is to be interrupted in view of the degree of progress of the game and the level of fatigue of the user.

The above embodiments and variations have been described with an example of shooting scenes; however, in the case of car or motorbike racing games, eye movements may be compared by identifying visual targets based on controls for avoiding obstacles or the like. In the case of team sports games such as soccer, eye movements may be compared by identifying visual targets based on commands for switching players to be controlled or commands for pass or shoot.

Furthermore, each functional block in the block diagrams (such as FIG. 3 and FIG. 43) may be implemented by a large scale integration (LSI) that is a semiconductor integrated circuit. The LSI may be configured as separate individual chips for each functional block, or may be configured as a single chip including part or all of the functional blocks. The name used here is LSI, but it may also be referred to as IC, system LSI, super LSI, or ultra LSI depending on the degree of integration.

Moreover, ways to achieve integration are not limited to the LSI, and a dedicated circuit or a general purpose processor can also achieve the integration. Field Programmable Gate Array (FPGA) that can be programmed after manufacturing LSIs or a reconfigurable processor that allows re-configuration of the connection or configuration of a circuit cell in an LSI can be used for the same purpose.

Furthermore, as described with reference to FIG. 10, the visual fatigue level measuring device according to each of the embodiments may be implemented by a computer system which includes a microprocessor, a ROM, a RAM, a hard disk unit, a display unit, a keyboard, a mouse, and so on. Here, a computer program is stored in the RAM or the hard disk unit. Each of the visual fatigue level measuring devices achieves its functions by the microprocessor operating according to the computer programs. Here, the computer program is configured by combining a plurality of instruction codes indicating instructions for the computer to achieve a predetermined function.

More specifically, such a program may cause a computer (or a processor) to execute a visual fatigue level measuring method for measuring the level of visual fatigue of a user who is viewing 3D video. The method includes: (a) presenting, to the user, left-eye video and right-eye video that are included in the 3D video; (b) receiving a control by the user with respect to the presented 3D video; (c) determining, when a predetermined control is received in the receiving in (b), that the user was gazing at a visual target in the 3D video presented in the presenting in (a) at a time at which the predetermined control was received, by referring to a target region information storing unit which stores target region information including information for identifying the visual target in the 3D video and information indicating time at which the visual target is presented in the presenting in (a); (d) determining two or more time periods based on a depth change of the visual target determined in the determining in (c), by referring to a target depth information storing unit which stores target depth information indicating a depth of the visual target in the 3D video, each of the two or more time periods being a time period for a test for measuring the level of visual fatigue; (e) obtaining data indicating eye movements of left and right eyes of the user with respect to the 3D video presented in the presenting in (a); (f) accumulating the obtained data indicating the eye movements in an eye movement accumulating unit; (g) extracting, from the data accumulated in the eye movement accumulating unit, data indicating the eye movements in each of the two or more time periods determined in the determining in (d); (h) comparing the eye movements in the two or more time periods based on the data extracted in the extracting in (g); and (i) determining the level of visual fatigue of the user based on a result of the comparison in the comparing in (h).

A part or all of the structural elements included in the visual fatigue level measuring device according to each embodiment may be configured as a removable IC card or as a stand-alone module. The IC card or the module is a computer system configured from a microprocessor, a ROM, a RAM, and so on. The IC card or the module may include the super-multi-function LSI. The IC card or the module achieves its function through the microprocessor's operation according to the computer program. The IC card or the module may also be implemented to be tamper-resistant.

Furthermore, one or more exemplary embodiments disclosed herein may be implemented as a method shown in the flowcharts in the above embodiments. The method may be implemented as a computer program executed by a computer, or as a digital signal including the computer program. Furthermore, the method may also be implanted by a recording medium storing the computer program or the digital signal in a computer readable recording medium such as flexible disc, a hard disk, a CD-ROM, an MO, a DVD, a DVD-ROM, a DVD-RAM, a BD (Blu-ray Disc), and a semiconductor memory.

Furthermore, of course, the computer program or the digital signal may be transmitted via a telecommunication line, a wireless or wired communication line, a network represented by the Internet, a data broadcast and so on.

Furthermore, by transferring the computer program or the digital signal by recording onto the aforementioned recording media, or by transferring the computer program or digital signal via the aforementioned network and the like, the visual fatigue level measuring device or method disclosed herein may be implemented using another independent computer system.

INDUSTRIAL APPLICABILITY

A visual fatigue level measuring device according to one or more exemplary embodiments disclosed herein is widely applicable to measure the level of visual fatigue of users who are viewing 3D video such as games, that is, to cases where viewers perform controls with respect to 3D video, and, in particular, is useful when configuring systems for games. Furthermore, the visual fatigue level measuring device according to one or more exemplary embodiments disclosed herein is also applicable to, for example, remote work, telesurgery, education, and training using systems based on experience in virtual reality.

The invention claimed is:

1. A visual fatigue level measuring device which measures a level of visual fatigue of a user who is viewing three-dimensional (3D) video, the visual fatigue level measuring device comprising:
   a video presenting unit configured to present, to the user, left-eye video and right-eye video that are included in the 3D video;
   a control input unit configured to receive a control by the user with respect to the presented 3D video;
   a gaze target identifying unit configured to, when the control input unit receives a predetermined control, (i) obtain, from a storing unit, target region information including information for identifying a visual target in the 3D video and information indicating time at which the visual target is presented by the video presenting unit, and (ii) determine that the user was gazing at the visual target in the 3D video presented by the video presenting unit at a time at which the control input unit received the predetermined control, by referring to the obtained target region information;
   a test period determining unit configured to (i) obtain, from the storing unit, target depth information indicating a depth of the visual target in the 3D video, and (ii) determine two or more time periods based on a depth change of the visual target identified by the gaze target identifying unit, by referring to the obtained target depth information, each of the two or more time periods being a time period for a test for measuring the level of visual fatigue;
   an eye movement obtaining unit configured to obtain data indicating eye movements of left and right eyes of the user with respect to the 3D video presented by the video presenting unit;
   an eye movement accumulating unit configured to accumulate the obtained data indicating the eye movements;
   an eye movement extracting unit configured to extract, from the data accumulated in the eye movement accumulating unit, data indicating the eye movements in each of the two or more time periods determined by the test period determining unit;
   an eye movement comparing unit configured to compare the eye movements in the two or more time periods based on the data extracted by the eye movement extracting unit; and
   a fatigue level determining unit configured to determine the level of visual fatigue of the user based on a result of the comparison by the eye movement comparing unit.

2. The visual fatigue level measuring device according to claim 1,
   wherein the visual target comprises a plurality of visual targets, and
   when the control input unit receives the predetermined control, the gaze target identifying unit is configured to select one of the visual targets presented by the video presenting unit, and determine that the user was gazing at the selected one of the visual targets.

3. The visual fatigue level measuring device according to claim 2,
   wherein the video presenting unit is configured to present, to the user, left-eye video and right-eye video that are included in a game in which the user aims at the visual target and shoots the visual target,
   the control input unit is configured to receive a control performed by the user to aim at the visual target for shooting, and the gaze target identifying unit is configured to identify the visual target at which the user is gazing based on the control received by the control input unit.

4. The visual fatigue level measuring device according to claim 1,
wherein the test period determining unit is configured to determine, as the time period for the test for measuring the level of visual fatigue, two or more different time periods which have a same depth change among depth changes of the visual target identified by the gaze target identifying unit.

5. The visual fatigue level measuring device according to claim 1,
wherein the fatigue level determining unit is configured to determine that the level of visual fatigue is higher as a difference in the eye movements between the two or more time periods increases.

6. The visual fatigue level measuring device according to claim 1,
wherein the visual target comprises a plurality of visual targets,
the gaze target identifying unit is configured to determine that the user was gazing at the visual targets concurrently presented by the video presenting unit, and
the test period determining unit is configured to identify, as a part of the time period for the test, a time period during which a visual target having a large amount of depth change among the visual targets identified by the gaze target identifying unit is being presented.

7. The visual fatigue level measuring device according to claim 1,
wherein the visual target comprises a plurality of visual targets,
the gaze target identifying unit is configured to determine that the user was gazing at the visual targets concurrently presented by the video presenting unit, and
the test period determining unit is configured to identify, as the time period for the test, a time period during which a visual target having a high speed depth change or a large amount of depth change among the visual targets is being presented.

8. The visual fatigue level measuring device according to claim 1,
wherein the eye movement comparing unit is configured to compare components of the eye movements which follow a depth movement of the visual target, among eye movement components.

9. The visual fatigue level measuring device according to claim 8,
wherein the eye movement comparing unit is configured to compare differences each between a position of a center of a pupil of the left eye and a position of a center of a pupil of the right eye.

10. The visual fatigue level measuring device according to claim 1,
wherein the gaze target identifying unit is further configured to generate information indicating a testable period that is a time period during which the user was gazing at the visual target,
the visual fatigue level measuring device further comprises:
a testable period accumulating unit configured to accumulate information indicating the testable period generated by the gaze target identifying unit; and
a target video information generating unit configured to generate video including the visual target, based on the information indicating the testable period accumulated in the testable period accumulating unit, and
the video presenting unit is further configured to present the video generated by the target video information generating unit.

11. The visual fatigue level measuring device according to claim 10, wherein the target video information generating unit is configured to generate video including a visual target which has a depth change equivalent to a depth change of a visual target in the testable period indicated by the information accumulated in the testable period accumulating unit.

12. The visual fatigue level measuring device according to claim 10, wherein the target video information generating unit is configured to generate video having a contrast equivalent to a contract between the visual target and background video in the testable period indicated by the information accumulated in the testable period accumulating unit.

13. The visual fatigue level measuring device according to claim 10,
wherein the target video information generating unit is configured to generate background video having a line segment which indicates a horizontal plane and which is in an amount equivalent to an amount of a line segment which indicates a horizontal plane in background video and which is contiguous to the visual target in the testable period indicated by the information accumulated in the testable period accumulating unit.

14. A visual fatigue level measuring method for measuring a level of visual fatigue of a user who is viewing 3D video, the visual fatigue level measuring method comprising:
(a) presenting, to the user, left-eye video and right-eye video that are included in the 3D video;
(b) receiving a control by the user with respect to the presented 3D video;
(c) determining, when a predetermined control is received in the receiving in (b), that the user was gazing at a visual target in the 3D video presented in the presenting in (a) at a time at which the predetermined control was received, by referring to a target region information storing unit which stores target region information including information for identifying the visual target in the 3D video and information indicating time at which the visual target is presented in the presenting in (a);
(d) determining two or more time periods based on a depth change of the visual target determined in the determining in (c), by referring to a target depth information storing unit which stores target depth information indicating a depth of the visual target in the 3D video, each of the two or more time periods being a time period for a test for measuring the level of visual fatigue;
(e) obtaining data indicating eye movements of left and right eyes of the user with respect to the 3D video presented in the presenting in (a);
(f) accumulating the obtained data indicating the eye movements in an eye movement accumulating unit;
(g) extracting, from the data accumulated in the eye movement accumulating unit, data indicating the eye movements in each of the two or more time periods determined in the determining in (d);
(h) comparing the eye movements in the two or more time periods based on the data extracted in the extracting in (g); and
(i) determining the level of visual fatigue of the user based on a result of the comparison in the comparing in (h).

15. A non-transitory computer-readable recording medium having recorded thereon a program for use in a visual fatigue level measuring device which measures a level of visual fatigue of a user who is viewing 3D video, the program causing a computer to execute the visual fatigue level measuring method according to claim 14.

\* \* \* \* \*